(12) United States Patent
Awatsuji et al.

(10) Patent No.: US 8,786,755 B2
(45) Date of Patent: Jul. 22, 2014

(54) METHOD AND APPARATUS FOR POLARIZATION IMAGING

(75) Inventors: Yasuhiro Awatsuji, Kyoto (JP); Tatsuki Tahara, Kyoto (JP)

(73) Assignee: National University Corporation Kyoto Institute of Technology, Kyoto (JP)

( * ) Notice: Subject to any disclaimer, the term of this patent is extended or adjusted under 35 U.S.C. 154(b) by 34 days.

(21) Appl. No.: 13/807,117

(22) PCT Filed: Jun. 22, 2011

(86) PCT No.: PCT/JP2011/064228
§ 371 (c)(1),
(2), (4) Date: Dec. 27, 2012

(87) PCT Pub. No.: WO2012/002207
PCT Pub. Date: Jan. 5, 2012

(65) Prior Publication Data
US 2013/0100333 A1    Apr. 25, 2013

(30) Foreign Application Priority Data

Jun. 29, 2010   (JP) ................................. 2010-148030

(51) Int. Cl.
*G01B 9/02* (2006.01)
*G02B 13/16* (2006.01)

(52) U.S. Cl.
USPC ............................ 348/335; 356/495; 356/503

(58) Field of Classification Search
USPC ....................................... 348/51, 57, 58, 335
See application file for complete search history.

(56) References Cited

U.S. PATENT DOCUMENTS 7,009,700 B2    3/2006   Dubois et al.

| | | |
|---|---|---|
| 2004/0156098 A1 | 8/2004 | Dubois et al. |
| 2006/0132799 A1 | 6/2006 | Dubois et al. |
| 2007/0146688 A1* | 6/2007 | Tezuka .......................... 356/124 |
| 2010/0253769 A1* | 10/2010 | Coppeta et al. ................. 348/58 |
| 2011/0273754 A1* | 11/2011 | Shimada et al. ................ 359/11 |
| 2011/0292402 A1 | 12/2011 | Awatsuji et al. |

FOREIGN PATENT DOCUMENTS

| | | |
|---|---|---|
| JP | 2003-148921 | 5/2003 |
| JP | 2004-538451 | 12/2004 |
| JP | 2005-283683 | 10/2005 |
| JP | 2007-033187 | 2/2007 |

(Continued)

OTHER PUBLICATIONS

International Search Report dated Sep. 6, 2011.

(Continued)

*Primary Examiner* — Tuan Ho
*Assistant Examiner* — Selam Gebriel
(74) *Attorney, Agent, or Firm* — Harness, Dickey & Pierce, P.L.C.

(57) ABSTRACT

A polarization imaging apparatus includes a laser light source and an image pickup element. Object light and reference light each include a first polarized-light component polarized in a first direction and a second polarized-light component polarized in a second direction that is different from the first direction. The image pickup element simultaneously captures an image of an interference pattern including (i) a first interference figure, (ii) a second interference figure, (iii) a third interference figure, and (iv) a fourth interference figure. The polarization imaging apparatus includes a reconstructing section generating respective reconstructed images of the object in regard to the first and second polarized-light components, from the first to fourth interference figures, and a polarized-light-image-calculating section obtaining polarized-light images from the reconstructed images.

24 Claims, 54 Drawing Sheets

(56) References Cited

FOREIGN PATENT DOCUMENTS

| | | |
|---|---|---|
| JP | 2007-086720 | 4/2007 |
| JP | 2008-032969 | 2/2008 |
| JP | 2008-122565 | 5/2008 |
| WO | WO 2010/092739 | 8/2010 |

OTHER PUBLICATIONS

International Preliminary Report on Patentability and English translation dated Sep. 10, 2012.

Beghuin, D. et al., "Single acquisition polarization imaging with digital holography," Electronics Letters, vol. 35, No. 23, pp. 2053-2055, Nov. 11, 1999.

Nomura, T. et al., "Polarization imagining of a 3D object by use of on-axis phase-shifting digital holography," Optics Letters, vol. 32, No. 5, pp. 481-483, Mar. 1, 2007.

Meng, X.F. et al., "Two-steph phase-shifting interferometry and its application in image encryption," Optics Letters, vol. 31, No. 10, pp. 1414-1416, May 15, 2006.

Partial English Translation of Sigma Corporation website, searched on Jun. 15, 2010, http://www,sigma-sd.com/SD15/jp/technology-colorsensor.html.

Mertz, L., "Real-time fringe-pattern analysis," Applied Optics, vol. 22, No. 10, pp. 1535-1539, May 15, 1983.

Takahama, Y. et al., "Shingle-shot Digital Holography by Using an arbitrary Phase-Shifting Formula," Proceedings of Optics Photonics Japan 2009, pp. 278-279, 2009.

Kuhn, J. et al., "Real-time dual-wavelength digital holographic microscopy with a single hologram acquisition," Optics Express, vol. 15, No. 12, pp. 7231-7242, May 29, 2007.

Kakue, T. et al., "Optical-Path Length-Shifting Color Digital Holography," Dai 4 Kai Shin Gazo System Joho Photonics Kenkyi Toronkai Abstract, pp. 5-6, Jun. 29, 2010.

Tahara, t. et al., "Parallel Two-Step Phase-Shifting Digital Holography System," Dai 4 Kai Shin Gazo System Joho Photonics Kenkyi Toronkai Abstract, pp. 53-54, Jun. 29, 2010.

* cited by examiner (a) Amplitude Distribution (P1)
(c) Phase Distribution (P1)
(b) Amplitude Distribution (P2)
(d) Phase Distribution (P2)

Phase Shift Method Using Three Types Of Phase Shift Amounts

FIG. 36
(a)
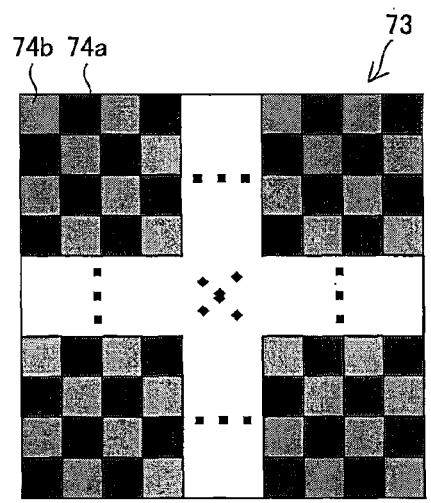
Filter 74a Transmitting Light Of λ1 And λ4
Filter 74b Transmitting Light Of λ2 And λ3
Structural Example Of Wavelength-Selection-Filter Array
(b)
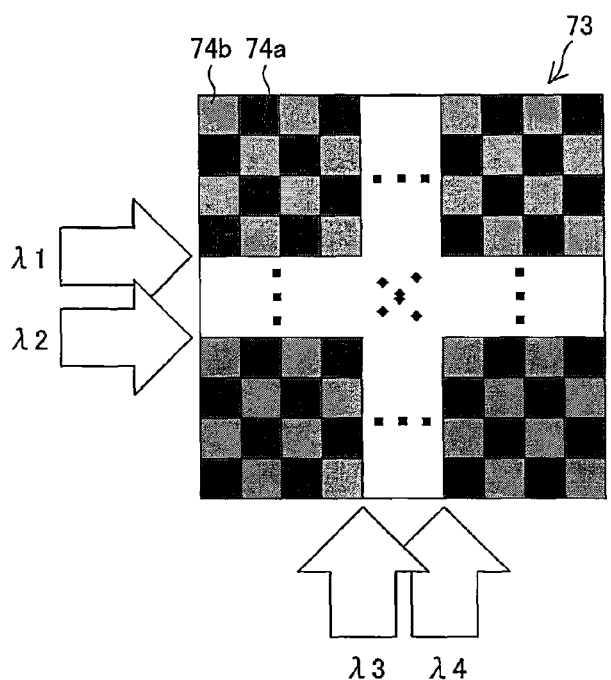
Cause Reference Light Of λ1 And λ4 To Enter Filter 74a From Different Directions
Cause Reference Light Of λ2 And λ3 To Enter Filter 74b From Different Directions Sensor Transmitting Light Of $\lambda 1$ And $\lambda 4$ Sensor Transmitting Light Of $\lambda 2$ And $\lambda 3$ Hologram Recording

METHOD AND APPARATUS FOR POLARIZATION IMAGING

TECHNICAL FIELD

The present invention relates to a polarization imaging apparatus and a polarization imaging method each of which is for performing polarization imaging of an object.

BACKGROUND ART

In the following descriptions, radian is used as a unit for phases. In recent years, there has been developed a polarization imaging camera that simultaneously obtains information on polarization in a plurality of directions. As a result, proposals are made for a polarization imaging apparatus for visualizing a polarized-light distribution of an object (Patent Literature 1) and a polarization microscope for visualizing a polarized-light distribution of an object (Patent Literature 2). Possible applications of polarization imaging are wide-ranging. Examples of such possible applications encompass (i) measurement of a structure of and/or a distortion of a material such as film or glass, which is used as a window material, a shop window, a display or the like, (ii) measurement of a film pressure of and a distortion of a thin film of a solar cell. Examples of possible applications of a polarization microscope encompass (a) characteristic evaluation of a crystal structure or a molecular structure, (b) identification of a rock forming mineral, (c) visualization of an internal structure of a living body (cell) without staining, and (d) visualization of a distribution of protein, collagen, or the like in a living cell.

A polarization imaging technique has been improved according to industrial requirements. However, the above-mentioned polarization imaging techniques cannot realize imaging of an instantaneous three-dimensional structure because of, for example, the following reasons. Specifically, a polarization microscope needs to raise a magnifying power of an objective lens, for observation of an object in a microscopic area. Accordingly, a photographable area extending in a depth direction becomes extremely narrow. Therefore, (i) it takes long to complete a product inspection because images should be taken multiple times, (ii) it is very difficult to observe how chemical structures change over time at different depth positions, and (iii) it is very difficult to observe, via a motion picture, how metabolite or the like behaves that is three-dimensionally spread in a living body (cell).

In order to solve the above-mentioned problems, some digital holography techniques for polarization imaging have been recently proposed. For example, Non-Patent Literature 1 discloses a technique for polarization imaging in which off-axis type digital holography is employed. According to such off-axis type digital holography, object light and reference light enter an image pickup element at different angles. It is therefore possible to obtain only a desired object image while a hologram is being reconstructed. This is because zero-order diffracted light, a conjugate image (minus first-order diffracted light), and an object image (first-order diffracted light) do not overlap each other. According to the configuration disclosed in Non-Patent Literature 1, it is possible to realize imaging of (i) an instantaneous three-dimensional structure and (ii) an instantaneous polarized-light distribution of an object. That is, it is possible to concurrently obtain distributions of polarized light of an object image at respective different positions in a depth direction.

FIG. 53 is a view illustrating a structure of a configuration of a conventional polarization imaging apparatus described in Non-patent Literature 1. FIG. 54 is a view illustrating a relation of reference light R1 and R2 and object light that enter an image pickup device provided in the polarization imaging apparatus shown in FIG. 53. This conventional polarization imaging apparatus (i) causes the reference light R1 and R2 to enter at different angles (for convenience, expressed in $\theta_1$ and $\theta_2$) from different directions with respect to the object light, respectively, which reference light R1 and R2 has respective components P1 and P2 in different polarization directions, and (ii) obtains a single-sheet interference figure (hologram).

FIG. 55 is a view illustrating a procedure in which an image is reconstructed from a hologram that is recorded by the polarization imaging apparatus. An obtained interference figure is subject to Fourier transform, and then a spatial spectrum distribution is obtained by calculation. Pieces of spatial spectrum information on an object in the respective polarization directions P1 and P2 are extracted. Subsequently, the pieces of information of the object in the respective polarization directions are subjected to (i) phase corrections, only by amounts relating to the respective angles $\theta_1$ and $\theta_2$, (ii) reverse Fourier transform, and (iii) image reconstruction by a diffraction calculation. After the image reconstruction, polarization imaging is performed while using complex amplitude distributions of the object in the respective polarization directions P1 and P2.

Non-Patent Literature 2 discloses a polarization imaging technique while using in-line type or on-axis type digital holography. According to the in-line type digital holography, object light and reference light enter an imaging element at identical angles. While a hologram is being reconstructed, (i) a zero-order diffracted light and a conjugate image (minus first-order diffracted light) which are noise components and (ii) an object image (first-order diffracted light) overlap each other. In order to obtain only a desired object image, it is therefore necessary to (i) sequentially photograph a plurality of holograms having respective different phases, respective different optical path lengths, or the like and (ii) make a calculation for extracting only the object image by use of a method such as a phase shift method or an optical-path-length shift method.

CITATION LIST

Patent Literatures

[Patent Literature 1]
Japanese Patent Application Publication, Tokukai, No. 2007-086720 (Publication Date: Apr. 5, 2007)
[Patent Literature 2]
Japanese Patent Application Publication, Tokukai, No. 2008-032969 (Publication Date: Feb. 14, 2008)

Non-Patent Literatures

[Non-Patent Literature 1]
D. Beghuin, et. al., "Single acquisition polarisation imaging with digital holography", ELECTRONICS LETTERS, 11 Nov. 1999, vol. 35, No. 23, pp. 2053-2055
[Non-Patent Literature 2]
Takanori Nomura, "Polarization imaging of a 3D object by use of on-axis phase-shifting digital holography", OPTICS LETTERS, Mar. 1, 2007, vol. 32, No. 5, pp. 481-483
[Non-Patent Literature 3]
M. F. Meng, et. al., "Two-step phase-shifting interferometry and its application in image encryption", OPTICS LETTERS, May 15, 2006, Vol. 31, No. 10, pp. 1414-1416

[Non-Patent Literature 4]

Sigma Corporation Site, [online], Searched on Jun. 15, 2010, on the Internet <URL: http://www.sigma-sd.com/SD15/jp/technology-colorsensor.html>

[Non-Patent Literature 5]

L. Mertz, "Real-time fringe-pattern analysis," Appl. Opt. 22, 1 535-1539 (1983).

[Non-Patent Literature 6]

Yushi Takahama and Kyoji Matsushima, "Shingle-shot Digital Holography By Using An Arbitrary Phase-Shifting Formula", Proceed ings of Optics Photonics Japan 2009, 278-279 (2009).

[Non-Patent Literature 7]

J. Kuhn, et. al., "Real-time dual-wavelength digital holographic microscopy with a single hologram acquisition", OPTICS EXPRESS, May 29 2007, vol. 15, No. 12, pp. 7231-7242

SUMMARY OF INVENTION

Technical Problem

However, according to the configuration employing the off-axis type digital holography technique disclosed in Non-Patent Literature 1, the following three problems (a) through (c) arise: (a) a photographable area (field of view) is narrow (the field of view is approximately ¼, as compared with a case where an in-line type digital holography is employed in which an image is recorded on a hologram which is spatially subjected to 4-division multiplex) because the off-axis type digital holography is employed; (b) a resolution of an image reconstructed from the hologram is low because an image quality of the image reconstructed from the hologram is low; and (c) in a case where an imaging optical system of the hologram is incorporated into a single device, such a single device becomes complex and upsized because an optical system is complex.

According to the configuration disclosed in Non-Patent Literature 1, a further problem arises that it is necessary to make adjustments with extremely-high accuracy with respect to (i) incident angles $\theta_1$ and $\theta_2$ of the reference light and (ii) hardware and/or software for "phase correction." Therefore, the inventors of the present application have found that there exists a problem that an accuracy of polarization imaging easily becomes low due to a slight change in position of and angle of an optical element.

According to the configuration disclosed in Non-Patent Literature 1, polarization imaging is realized by using pieces of amplitude information of and pieces of phase difference information of an object in respective different polarization directions P1 and P2. However, since the pieces of phase difference information are subjected to phase modulations in accordance with the respective incident angles $\theta_1$ and $\theta_2$ of the reference light, the phase modulations need to be removed to achieve polarization imaging with accuracy. For removing the phase modulations, respective incident angles of the reference light are first physically adjusted, and then subject to respective highly-accurate measurements. Then, phase corrections of the object light in respective polarization directions must be made by comparing amounts of correction found from recorded interference figures with respective physically-measured values.

When the phase corrections are actually made on a computer, the values of the respective angles $\theta_1$ and $\theta_2$ are required to be accurate up to three decimal places, four decimal places, or more than four decimal places. For physical adjustment of the angles, an extremely high accuracy up to approximately 0.006 [°] (≈0.0001 [rad]) is required with respect to an object that is 300 mm apart from the polarization imaging apparatus. Because such a high accuracy is required in the adjustment of the angles, the polarization imaging apparatus is sensitive to deviation in angle of object light relative to each reference light. Accordingly, a slight change in angle and/or position of an optical element (e.g., each BS (beam splitter element), each M (mirror), etc. in FIG. 53) makes it impossible to obtain accurate phase difference information. This easily deteriorates accuracy in polarization imaging. This configuration described in Non-Patent Literature 1 is demonstrated for a two-dimensional weak-scattering object, such as a wave plate, that has dependency on polarization. However, the configuration has not been demonstrated for a three-dimensional strong-scattering object. Actual application of the configuration to a three-dimensional strong-scattering object is exceptionally difficult.

FIG. 56 is a view illustrating a problem of the polarization imaging apparatus disclosed in Non-Patent literature 1. According to the configuration disclosed in Non-Patent literature 1, a problem arises that a photographable area becomes narrow. This is because, in a case where a large object is to be measured, the object and an unnecessary image component overlap each other in a spatial spectrum, unnecessary images are superimposed on a reconstructed image.

Apart from the illustration of FIG. 56, in the configuration disclosed in Non-Patent Literature 1, an unnecessary image component overlaps on a reconstructed image when information on a detailed structure of an object is to be recorded. In a case where this overlap is avoided, a resolution of the reconstructed image deteriorates. Meanwhile, in a case where a resolution is forcibly increased, an unnecessary image overlaps. This means that in application of the configuration as described in Non-Patent Literature 1 to a microscope with a high magnifying power, resolution cannot be enhanced. This consequently causes a problem in that sharp imaging of a microscopic structure is extremely difficult.

On the other hand, according to the configuration disclosed in Non-Patent Literature 2, the in-line type digital holography is employed. Accordingly, a photographable area is wider and image quality of the reconstructed image is higher as compared with the configuration disclosed in Non-Patent literature 1. Furthermore, according to the configuration disclosed in Non-Patent Literature 2, an optical system is simpler, as compared with that disclosed in Non-Patent Literature 1. Accordingly, in a case where an imaging optical system of a hologram is incorporated into a single device, it is easy to downsize such a single device.

However, in the configuration disclosed in Non-Patent Literature 2, it is necessary, for obtaining an object image, to successively capture images of intensity distributions information of object light on a plane of an image pickup element in a plurality of polarization directions. Further, for polarization imaging, it is necessary to capture images of holograms sequentially in a plurality of polarization directions, for example, by rotating a ½ wave plate provided in an optical system. This requires plural image-capturing operations. This makes it impossible to perform imaging of (i) an instantaneous three-dimensional structure and (ii) an instantaneous polarized-light distribution of a dynamically-changing object.

As is clear from the description above, no technique has been disclosed and reported in which polarization imaging can be realized with a high image quality, by simultaneously acquiring (i) instantaneous information on a three-dimensional structure, (ii) instantaneous information on a polarized-light distribution, and (iii) instantaneous spectral characteristics of a dynamically-changing object.

The present invention is attained in view of the above problems. An object of the present invention is to provide a high-image-quality polarization imaging apparatus that can simultaneously acquire, by one image pickup, (i) wide-area and detailed three-dimensional information on an object, (ii) a polarized-light distribution of the object, and (iii) spectral characteristics of the object. The three-dimensional information includes information on a three-dimensional shape, position, or distribution of an object.

Solution to Problem

A polarization imaging apparatus of the present invention includes: at least one light source for supplying reference light and object light; an image pickup section capturing images of interference figures each formed from the reference light and the object light that reaches the image pickup section through an object; a reconstructed-image-producing section producing reconstructed images; and a polarized-light-image-calculating section obtaining polarized-light images, wherein: the object light and the reference light each include a first polarized-light component polarized in a first direction and a second polarized-light component polarized in a second direction that is different from the first direction, both of which object light and reference light enter the image pickup section; the image pickup section simultaneously captures an image of an interference pattern including (i) a first interference figure formed by interference between the object light and the reference light which has the first polarized-light component and a first phase, (ii) a second interference figure formed by interference between the object light and the reference light which has the first polarized-light component and a second phase, (iii) a third interference figure formed by interference between the object light and the reference light which has the second polarized-light component and the first phase, and (iv) a fourth interference figure formed by interference between the object light and the reference light which has the second polarized-light component and the second phase; the reconstructed-image-producing section (I) produces a first reconstructed image of the object in regard to the first polarized-light component, after (a) extraction of pixels corresponding to the first interference figure and the second interference figure from the interference pattern and (b) pixel interpolation and (II) produces a second reconstructed image of the object in regard to the second polarized-light component, after (a) extraction of pixels corresponding to the third interference figure and the fourth interference figure from the interference pattern and (b) pixel interpolation; and the polarized-light-image-calculating section obtains the polarized-light images from the first reconstructed image and the second reconstructed image, the polarized-light images corresponding to respective positions in each of the reconstructed images of the object.

For example in the simplest example case that involves two types of polarized light and two phase levels and employs one light source, a polarization imaging apparatus includes: a light source supplying reference light and object light; an image pickup section capturing images of interference figures each formed from the reference light and the object light that reaches the image pickup section through an object; a reconstructed-image-producing section producing reconstructed images; and a polarized-light-image-calculating section obtaining polarized-light images, wherein: the object light and the reference light each include a first polarized-light component polarized in a first direction and a second polarized-light component polarized in a second direction that is different from the first direction, both of which object light and reference light enter the image pickup section; the image pickup section simultaneously captures an image of an interference pattern including four types of interference images in total, the four types of interference images being (i) first and second interference figures each formed by interference between the object light and the reference light with one of two different phases, in regard to the first polarized-light component, and (ii) third and fourth interference figures each formed by interference between the object light and the reference light with one of the two different phases, in regard to the second polarized-light component; the reconstructed-image-producing section (I) produces a first reconstructed image of the object in regard to the first polarized-light component, after (a) extraction of pixels corresponding to the first and second interference figures from the interference pattern and (b) pixel interpolation and (II) produces a second reconstructed image of the object in regard to the second polarized-light component, after (a) extraction of pixels corresponding to the third and fourth interference figures from the interference pattern and (b) pixel interpolation; and the polarized-light-image-calculating section obtains the polarized-light images from the first reconstructed image and the second reconstructed image, the polarized-light images corresponding to respective positions in each of the reconstructed images of the object.

A method of the present invention for polarization imaging in which a polarization state of object light is obtained by capturing images of interference figures each formed by reference light and the object light that reaches through an object, the method includes the steps of: capturing, simultaneously, an image of an interference pattern including first to fourth interference figures formed from the object light and the reference light, the object light and the reference light each including a first polarized-light component polarized in a first direction and a second polarized-light component polarized in a second direction that is different from the first direction, the first interference figure being formed by interference between the object light and the reference light which has the first polarized-light component and a first phase, the second interference figure being formed by interference between the object light and the reference light which has the first polarized-light component and a second phase, the third interference figure being formed by interference between the object light and the reference light which has the second polarized-light component and the first phase, and the fourth interference figure being formed by interference between the object light and the reference light which has the second polarized-light component and the second phase; producing (I) a first reconstructed image of the object in regard to the first polarized-light component, after (a) extraction of pixels corresponding to the first interference figure and the second interference figure from the interference pattern and (b) pixel interpolation and (II) a second reconstructed image of the object in regard to the second polarized-light component, after (a) extraction of pixels corresponding to the third interference figure and the fourth interference figure from the interference pattern and (b) pixel interpolation; and obtaining polarized-light images from the first reconstructed image and the second reconstructed image, the polarized-light images corresponding to respective positions in each of the reconstructed images of the object.

For example in the simplest example case that involves two types of polarized light and two phase levels and employs one light source, a method for polarization imaging in which a polarization state of object light is obtained by capturing images of interference figures each formed by reference light and the object light that reaches through an object, the method includes the steps of: capturing, simultaneously, an image of an interference pattern including first to fourth interference figures formed from the object light and the reference light, the object light and the reference light each including a first polarized-light component polarized in a first direction and a second polarized-light component polarized in a second direction that is different from the first direction, (i) the first and second interference figures each being formed by interference between the object light and the reference light with one of two different phases, in regard to the first polarized-light component, (ii) the third and fourth interference figures each being formed by interference between the object light and the reference light with one of the two different phases, in regard to the second polarized-light component; producing (I) a first reconstructed image of the object in regard to the first polarized-light component, after (a) extraction of pixels corresponding to the first and second interference figures from the interference pattern and (b) pixel interpolation and (II) a second reconstructed image of the object in regard to the second polarized-light component, after (a) extraction of pixels corresponding to the third and fourth interference figures from the interference pattern and (b) pixel interpolation; and obtaining polarized-light images from the first and second reconstructed images, the polarized-light images corresponding to respective positions in each of the reconstructed images of the object.

In the above configuration, it is possible to (i) simultaneously obtain m×n types of interference figures (m is the number of different phase levels, n is the number of different polarization directions, and there are 4 types of interference figures when m=2 and n=2, for example) for reference light having different phases and different polarization directions, and (ii) obtain a reconstructed image for each polarization direction by a phase shift method. From the reconstructed image, a polarization state of the object light at each position of the reconstructed image of the object is obtained. This makes it possible to eliminate the need for capturing images multiple times and to obtain detailed three-dimensional information and polarized light distributions of a large area of the object by one image pickup. Therefore, the above configuration allows for imaging of an instantaneous three-dimensional structure and instantaneous polarized light distributions of a dynamically-changing object.

That is, the minimum number of two polarization directions is two, the minimum number of phase levels of the reference light is two, and correspondingly, the minimum number of types of interference figures simultaneously captured is four. Even when the respective numbers of the polarization directions, the phase levels, and the types of interference figures are greater than the above minimum numbers, imaging of an instantaneous three-dimensional structure and polarized-light distributions can be similarly performed. By using a plurality of light sources, spectral characteristics can also be obtained.

A polarization imaging apparatus of the present invention includes: a light source for supplying reference light and object light; an image pickup section capturing images of interference figures each formed from the reference light and the object light that reaches the image pickup section through an object; a reconstructed-image-producing section producing reconstructed images; and a polarized-light-image-calculating section obtaining polarized-light images, wherein: the light source supplies light of at least one wavelength type; the object light and the reference light each include a first polarized-light component polarized in a first direction and a second polarized-light component polarized in a second direction that is different from the first direction, both of which object light and reference light enter the image pickup section; the image pickup section simultaneously captures an image of an interference pattern including (i) a first interference figure formed by interference between the object light and the reference light which has the first polarized-light component and a first optical path length, (ii) a second interference figure formed by interference between the object light and the reference light which has the first polarized-light component and a second optical path length, (iii) a third interference figure formed by interference between the object light and the reference light which has the second polarized-light component and the first optical path length, and (iv) a fourth interference figure formed by interference between the object light and the reference light which has the second polarized-light component and the second optical path length; the reconstructed-image-producing section (I) produces a first reconstructed image of the object in regard to the first polarized-light component, after (a) extraction of pixels corresponding to the first interference figure and the second interference figure from the interference pattern and (b) pixel interpolation and (II) produces a second reconstructed image of the object in regard to the second polarized-light component, after (a) extraction of pixels corresponding to the third interference figure and the fourth interference figure from the interference pattern and (b) pixel interpolation; and the polarized-light-image-calculating section obtains the polarized-light images from the first reconstructed image and the second reconstructed image, the polarized-light images corresponding to respective positions in each of the reconstructed images of the object.

For example in the simplest example case that involves two types of polarized light and two phase levels and employs one light source, a polarization imaging apparatus includes: a light source for supplying reference light and object light; an image pickup section capturing images of interference figures each formed from the reference light and the object light that reaches the image pickup section through an object; a reconstructed-image-producing section producing reconstructed images; and a polarized-light-image-calculating section obtaining polarized-light images, wherein: the light source supplies light of at least one wavelength type; the object light and the reference light each include a first polarized-light component polarized in a first direction and a second polarized-light component polarized in a second direction that is different from the first direction, both of which object light and reference light enter the image pickup section; the image pickup section simultaneously captures an interference pattern including (i) first and second interference figures each having a different optical path length from the object, in regard to the first polarized-light component, and (ii) third and fourth interference figures each having a different optical path length from the object, in regard to the second polarized-light component; the reconstructed-image-producing section (I) produces a first reconstructed image of the object in regard to the first polarized-light component, after (a) extraction of pixels corresponding to the first interference figure and the second interference figure from the interference pattern and (b) pixel interpolation and (II) produces a second reconstructed image of the object in regard to the second polarized-light component, after (a) extraction of pixels corresponding to the third interference figure and the fourth interference figure from the interference pattern and (b) pixel interpolation; and the polarized-light-image-calculating section obtains the polarized-light images from the first reconstructed image and the second reconstructed image, the polarized-light images corresponding to respective positions in each of the reconstructed images of the object.

A method of the present invention for polarization imaging in which a polarization state of object light is obtained by capturing images of interference figures each formed by reference light and the object light that reaches through an object, the method includes the steps of: capturing, simultaneously, an image of an interference pattern including first to fourth interference figures formed from the object light and the reference light, the object light and the reference light each including a first polarized-light component polarized in a first direction and a second polarized-light component polarized in a second direction that is different from the first direction, the first interference figure being formed by interference between the object light and the reference light which has the first polarized-light component and a first optical path length, the second interference figure being formed by interference between the object light and the reference light which has the first polarized-light component and a second optical path length, the third interference figure being formed by interference between the object light and the reference light which has the second polarized-light component and the first optical path length, and the fourth interference figure being formed by interference between the object light and the reference light which has the second polarized-light component and the second optical path length; producing (I) a first reconstructed image of the object in regard to the first polarized-light component, after (a) extraction of pixels corresponding to the first interference figure and the second interference figure from the interference pattern and (b) pixel interpolation and (II) a second reconstructed image of the object in regard to the second polarized-light component, after (a) extraction of pixels corresponding to the third interference figure and the fourth interference figure from the interference pattern and (b) pixel interpolation; and obtaining a polarization state from the first reconstructed image and the second reconstructed image, the polarization state corresponding to each position in each of the reconstructed images of the object.

For example in the simplest example case that involves two types of polarized light and two phase levels and employs one light source, a method of the present invention for polarization imaging in which a polarization state of object light is obtained by capturing images of interference figures each formed by reference light and the object light that reaches through an object, the method includes the steps of: capturing, simultaneously, an image of an interference pattern including first to fourth interference figures formed from the object light and the reference light, the object light and the reference light each including a first polarized-light component polarized in a first direction and a second polarized-light component polarized in a second direction that is different from the first direction, the first and second interference figures each having a different optical path length from the object, in regard to the first polarized-light component, the third and fourth interference figures each having a different optical path length from the object, in regard to the second polarized-light component; producing (I) a first reconstructed image of the object in regard to the first polarized-light component, after (a) extraction of pixels corresponding to the first interference figure and the second interference figure from the interference pattern and (b) pixel interpolation and (II) a second reconstructed image of the object in regard to the second polarized-light component, after (a) extraction of pixels corresponding to the third interference figure and the fourth interference figure from the interference pattern and (b) pixel interpolation; and obtaining a polarization state from the first reconstructed image and the second reconstructed image, the polarization state corresponding to each position in each of the reconstructed images of the object.

In the above configuration, it is possible to (i) simultaneously obtain m'×n' types of interference figures (m' is the number of different optical path lengths of the reference light, n' is the number of different polarization directions, and there are 4 types of interference figures when m'=2 and n'=2, for example) for the different optical path lengths and the different polarization directions, and (ii) to obtain a reconstructed image for each polarization direction by an optical-path-length shift method. From the reconstructed image, a polarization state of the object light at each position of the reconstructed image of the object is obtained. This makes it possible to eliminate the need for capturing images multiple times and to obtain detailed three-dimensional information and polarized light distributions of a large area of the object by one image pickup. Therefore, the above configuration allows for imaging of an instantaneous three-dimensional structure and instantaneous polarized light distributions of a dynamically-changing object.

That is, the minimum number of two polarization directions is two, the minimum number of phase levels of the reference light is two, and correspondingly, the minimum number of types of interference figures simultaneously captured is four. Even when the respective numbers of the polarization directions, the phase levels, and the types of interference figures are greater than the above minimum numbers, imaging of an instantaneous three-dimensional structure and polarized-light distributions can be similarly performed. By using a plurality of light sources, spectral characteristics can also be obtained.

Advantageous Effects of Invention

A polarization imaging apparatus of the present invention includes: at least one light source for supplying reference light and object light; an image pickup section capturing images of interference figures each formed from the reference light and the object light that reaches the image pickup section through an object; a reconstructed-image-producing section producing reconstructed images; and a polarized-light-image-calculating section obtaining polarized-light images, wherein: the object light and the reference light each include a first polarized-light component polarized in a first direction and a second polarized-light component polarized in a second direction that is different from the first direction, both of which object light and reference light enter the image pickup section; the image pickup section simultaneously captures an image of an interference pattern including (i) a first interference figure formed by interference between the object light and the reference light which has the first polarized-light component and a first phase, (ii) a second interference figure formed by interference between the object light and the reference light which has the first polarized-light component and a second phase, (iii) a third interference figure formed by interference between the object light and the reference light which has the second polarized-light component and the first phase, and (iv) a fourth interference figure formed by interference between the object light and the reference light which has the second polarized-light component and the second phase; the reconstructed-image-producing section (I) produces a first reconstructed image of the object in regard to the first polarized-light component, after (a) extraction of pixels corresponding to the first interference figure and the second interference figure from the interference pattern and (b) pixel interpolation and (II) produces a second reconstructed image of the object in regard to the second polarized-light component, after (a) extraction of pixels corresponding to the third interference figure and the fourth interference figure from the interference pattern and (b) pixel interpolation; and the polarized-light-image-calculating section obtains the polarized-light images from the first reconstructed image and the second reconstructed image, the polarized-light images corresponding to respective positions in each of the reconstructed images of the object.

For example in the simplest example case that involves two types of polarized light and two phase levels and employs one light source, a polarization imaging apparatus includes: a light source supplying reference light and object light; an image pickup section capturing images of interference figures each formed from the reference light and the object light that reaches the image pickup section through an object; a reconstructed-image-producing section producing reconstructed images; and a polarized-light-image-calculating section obtaining polarized-light images, wherein: the object light and the reference light each include a first polarized-light component polarized in a first direction and a second polarized-light component polarized in a second direction that is different from the first direction, both of which object light and reference light enter the image pickup section; the image pickup section simultaneously captures an image of an interference pattern including four types of interference images in total, the four types of interference images being (i) first and second interference figures each formed by interference between the object light and the reference light with one of two different phases, in regard to the first polarized-light component, and (ii) third and fourth interference figures each formed by interference between the object light and the reference light with one of the two different phases, in regard to the second polarized-light component; the reconstructed-image-producing section (I) produces a first reconstructed image of the object in regard to the first polarized-light component, after (a) extraction of pixels corresponding to the first and second interference figures from the interference pattern and (b) pixel interpolation and (II) produces a second reconstructed image of the object in regard to the second polarized-light component, after (a) extraction of pixels corresponding to the third and fourth interference figures from the interference pattern and (b) pixel interpolation; and the polarized-light-image-calculating section obtains the polarized-light images from the first reconstructed image and the second reconstructed image, the polarized-light images corresponding to respective positions in each of the reconstructed images of the object.

Accordingly, it is possible to (i) simultaneously obtain four types of interference figures for different optical path lengths or reference light that has different phases and different polarization directions, and to (ii) obtain a reconstructed image for each polarization direction by an optical-path-length shift method or a phase shift method. From the reconstructed image, a polarization state of the object light at each position of the reconstructed image of the object can be obtained. This makes it possible to eliminate the need for capturing images multiple times and to obtain detailed three-dimensional information and polarized light distributions of a large area of the object by one image pickup.

The above explanatory case involves two polarization directions and two types of optical path lengths, that is, phase differences. For this combination, the minimum number of types of interference figures simultaneously captured is four. Even when four or more types of interference figures are simultaneously captured for a combination of two or more types of polarization directions and two or more types of optical path lengths, that is, phase differences phases, imaging of an instantaneous three-dimensional structure and polarized-light distributions of an object can be similarly performed. By using two or more light sources, imaging of an instantaneous three-dimensional structure, and polarized-light distributions, and spectral characteristics of an object can be performed.

Figure 2:
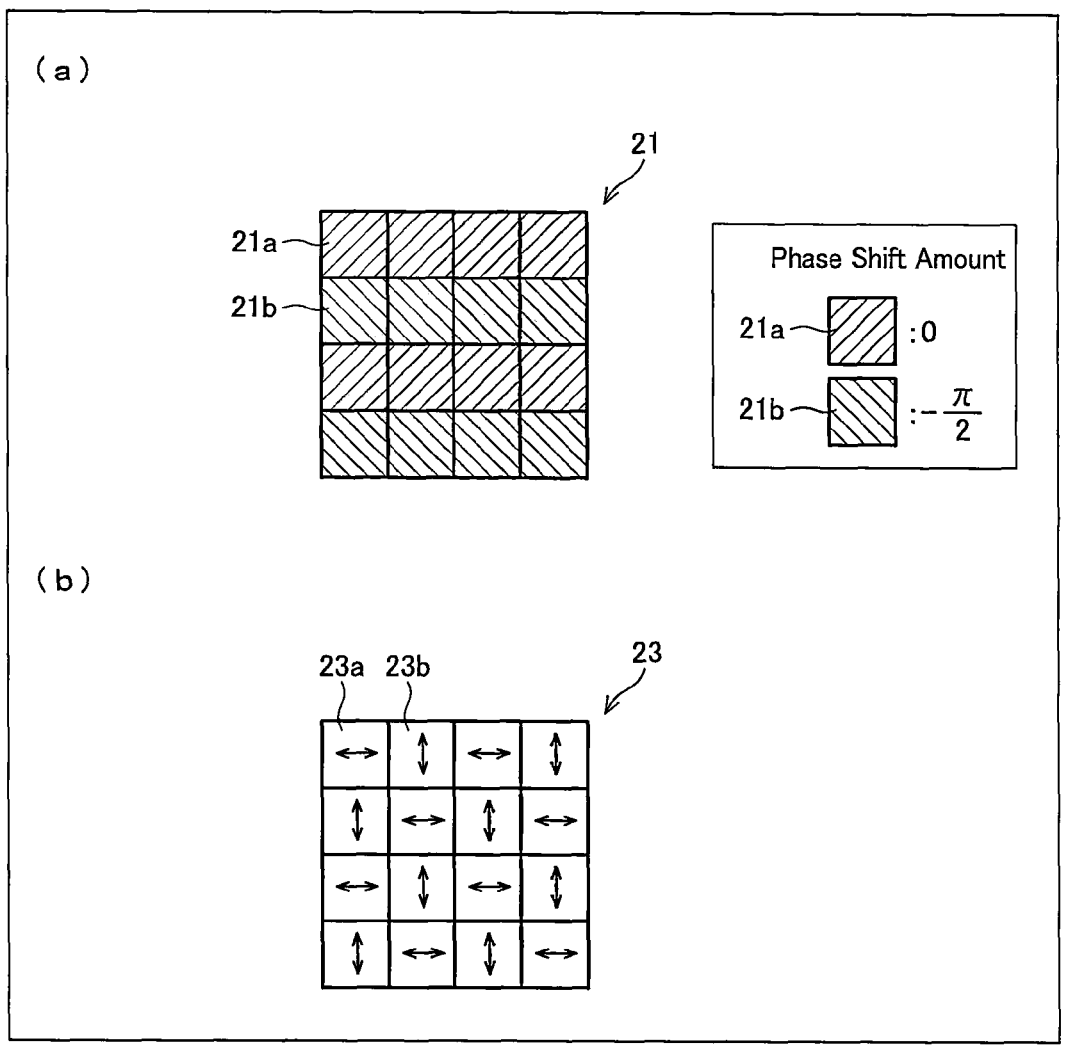
FIG. 2

(a) of FIG. 2 is a plan view schematically illustrating a part of a phase-shift-array device; and (b) of FIG. 2 is a plan view schematically illustrating a part of a polarizer-array device.

Figure 3:
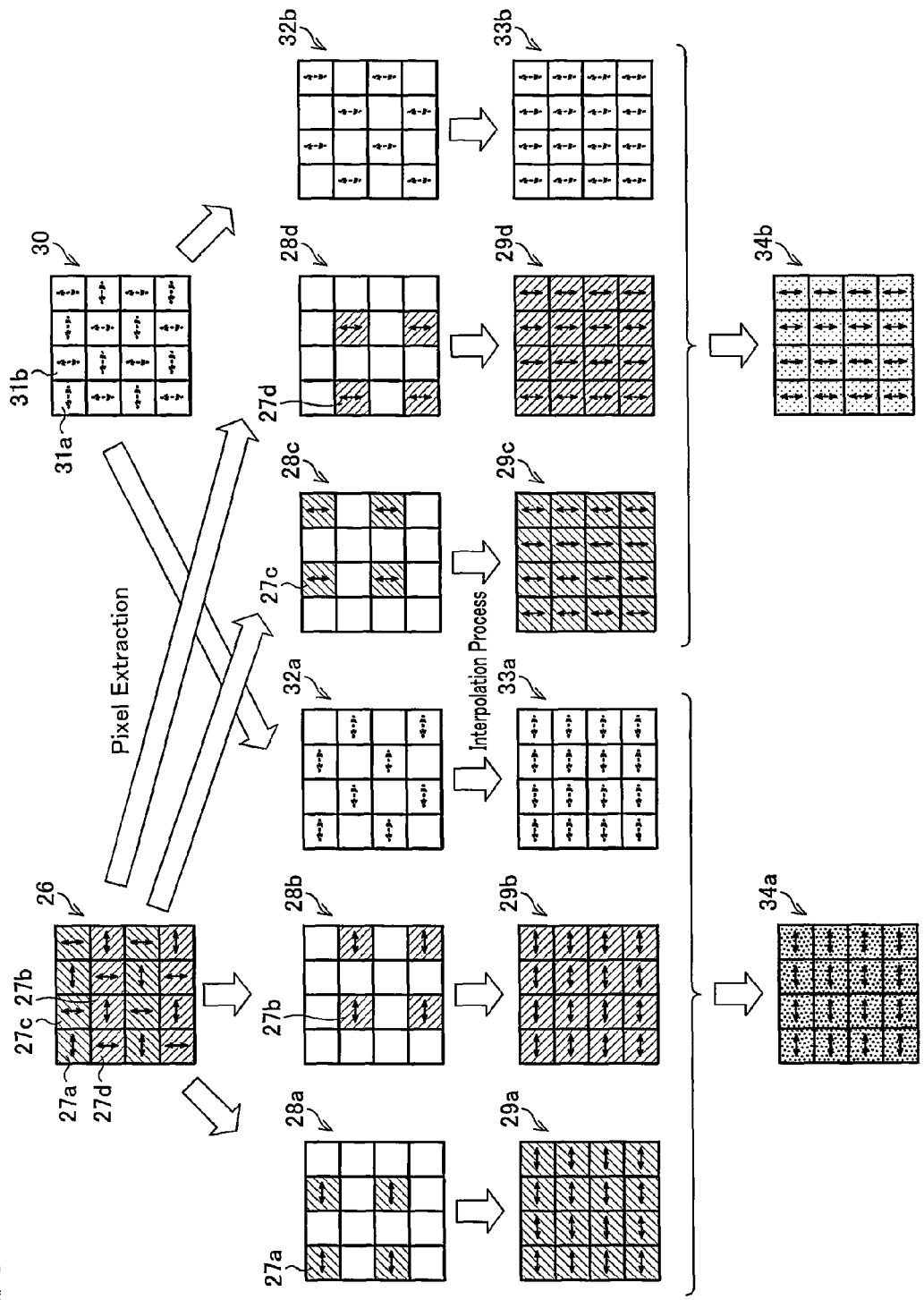

FIG. 3 illustrates an image reconstruction algorithm in a reconstructing section.

FIG. 4

Figure 4:
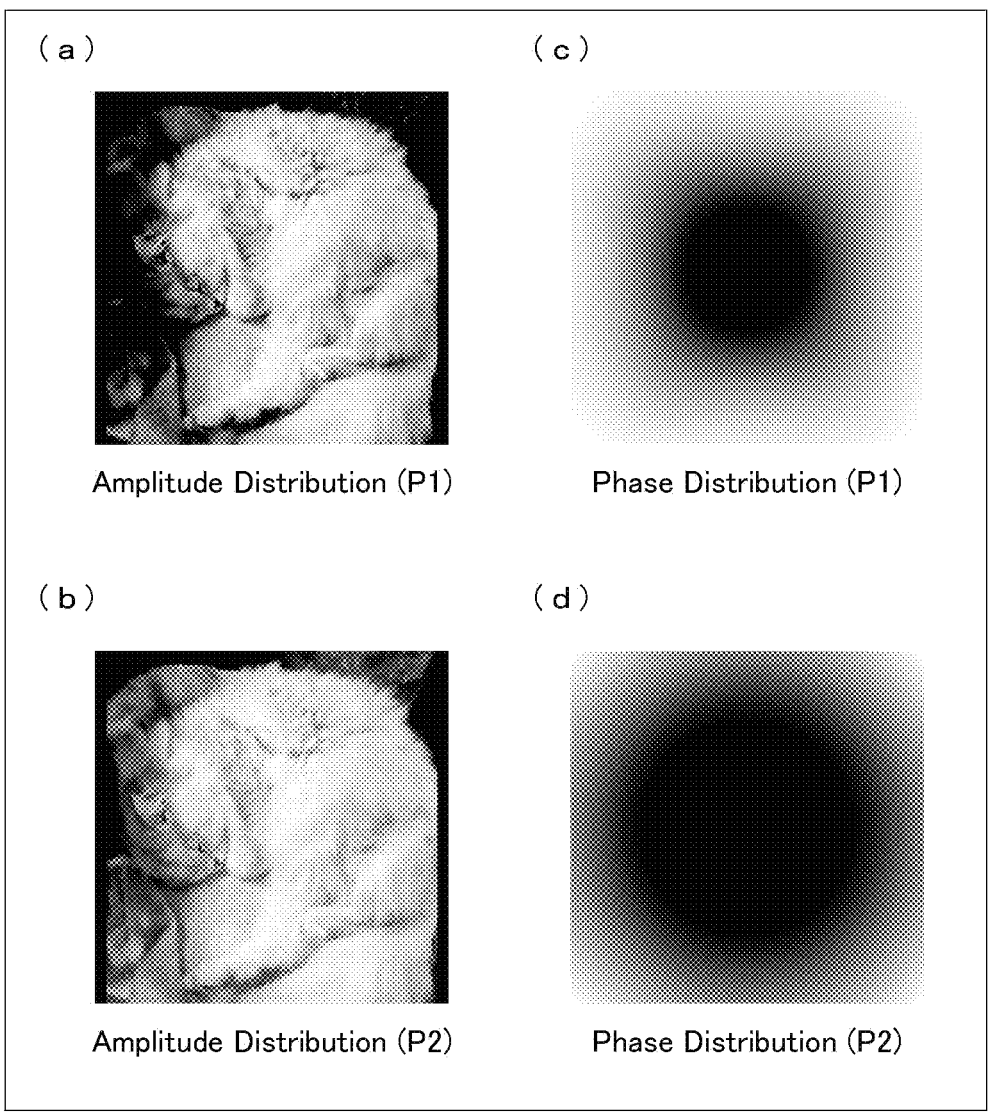

(a) of FIG. 4 shows an image of an amplitude distribution of a light component polarized in a horizontal direction (P1); (b) of FIG. 4 shows an image of an amplitude distribution of a light component polarized in a vertical direction (P2); (c) of FIG. 4 shows an image of a phase distribution in a case where laser light polarized in the horizontal direction (P1) passes through an object; and (d) of FIG. 4 shows an image of a phase distribution in a case where a laser light polarized in a vertical direction (P2) passes through the object.

Figure 5:
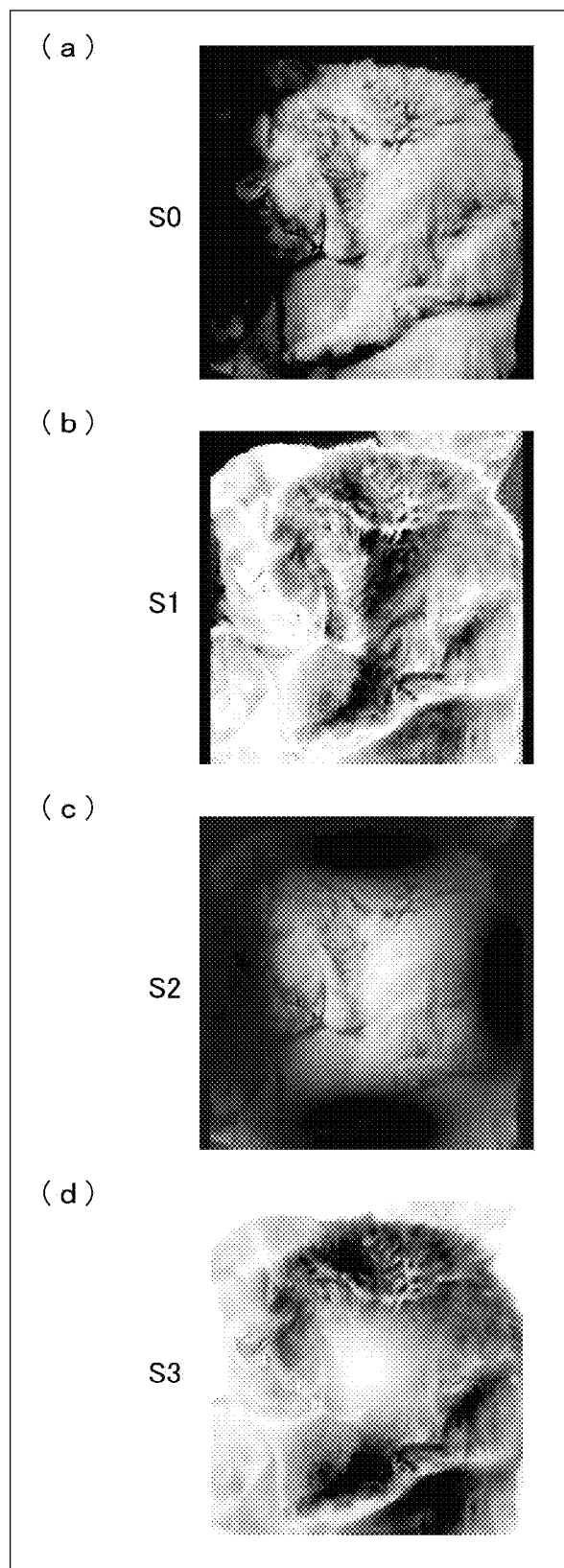

FIG. 5 shows images respectively illustrating Stokes parameters S0 to S3 of object light.

Figure 6:
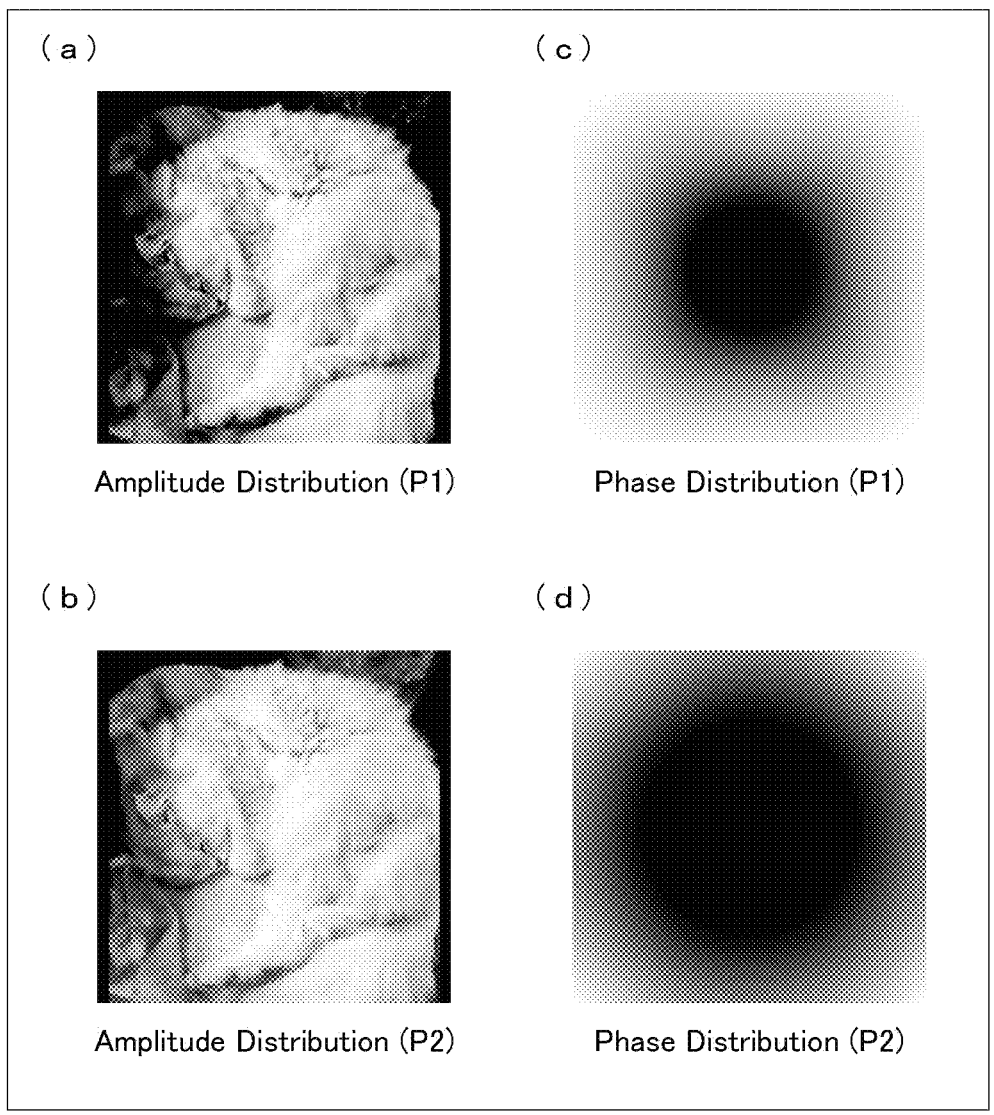

FIG. 6 shows images illustrating a result of simulation that is performed in accordance with one embodiment, in regard to reconstructed images of an object.

Figure 7:
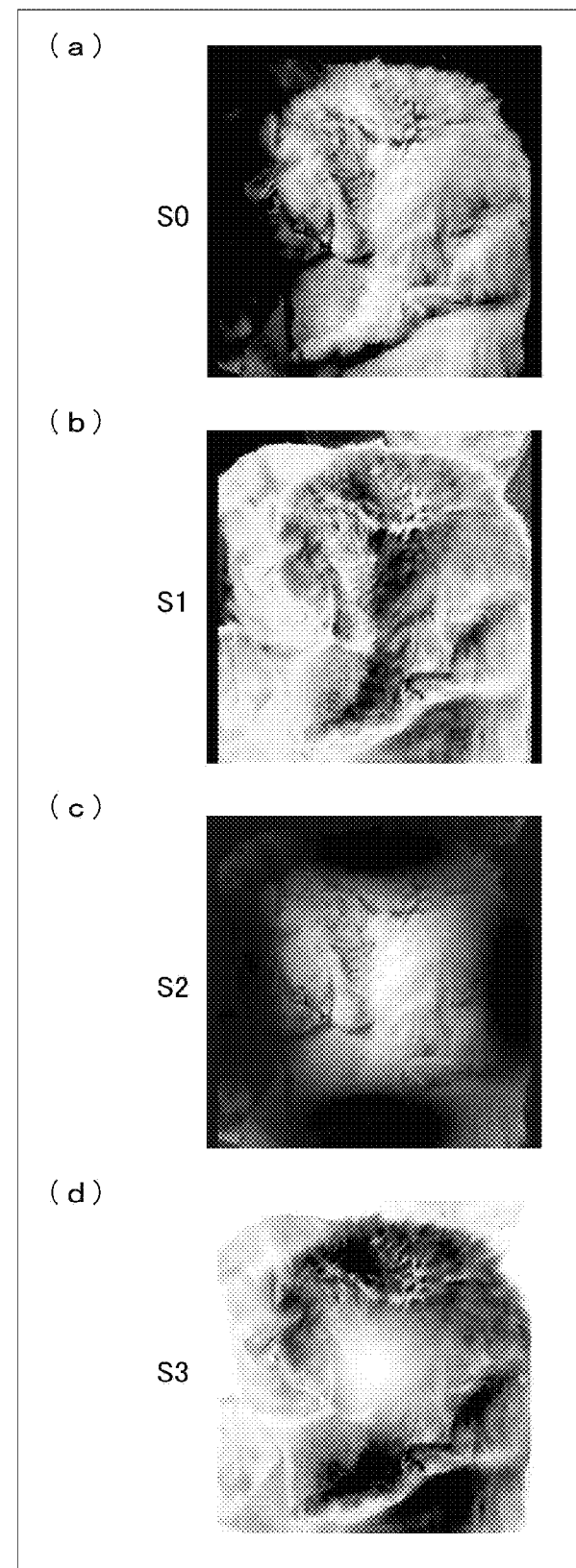

FIG. 7 shows images respectively illustrating Stokes parameters obtained from phase distributions and the reconstructed images that result from the simulation.

Figure 8:
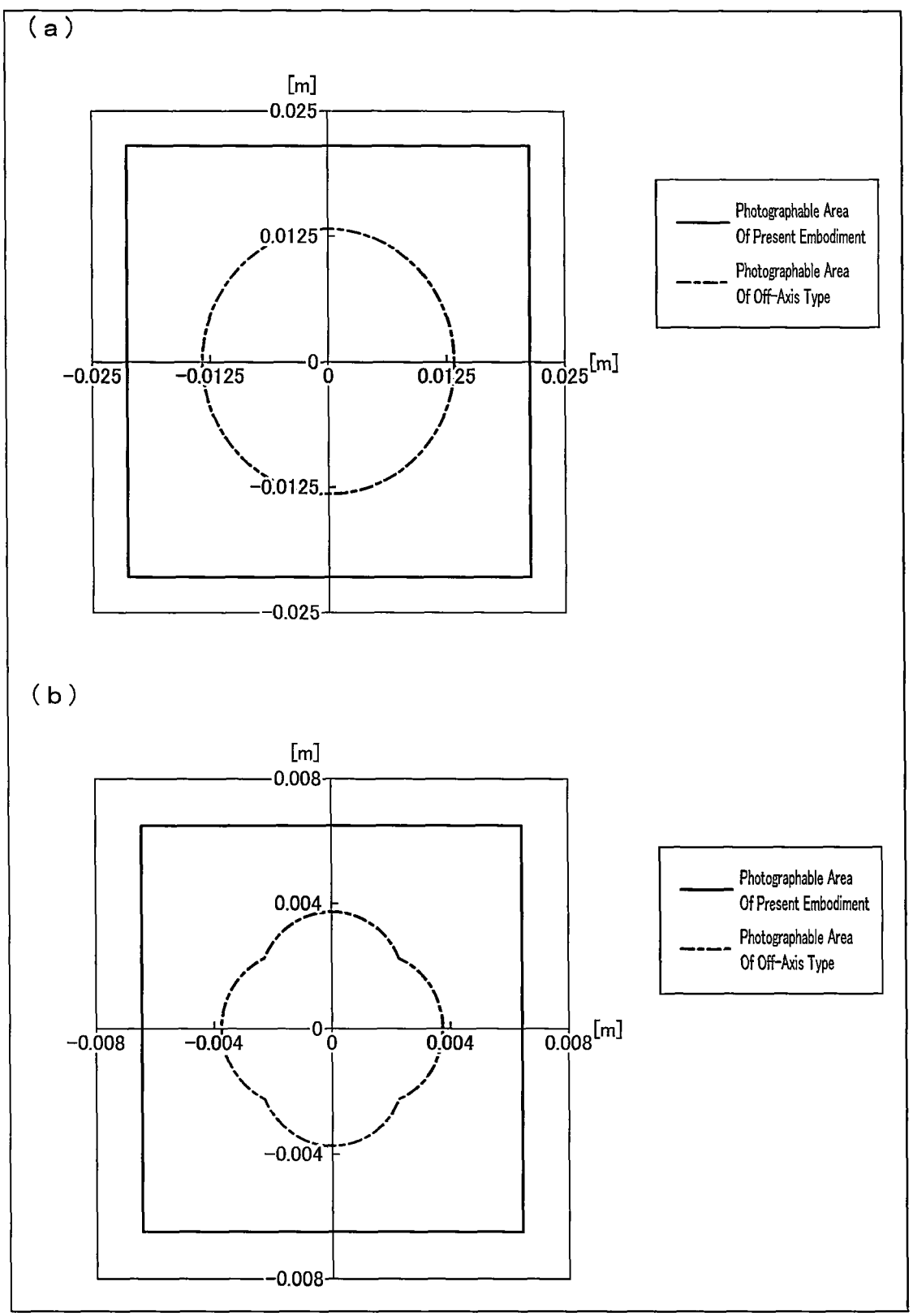

FIG. 8 shows a photographable area of a polarization imaging apparatus according to one embodiment of the present invention and a photographable area of an off-axis type polarization imaging apparatus.

Figure 9:
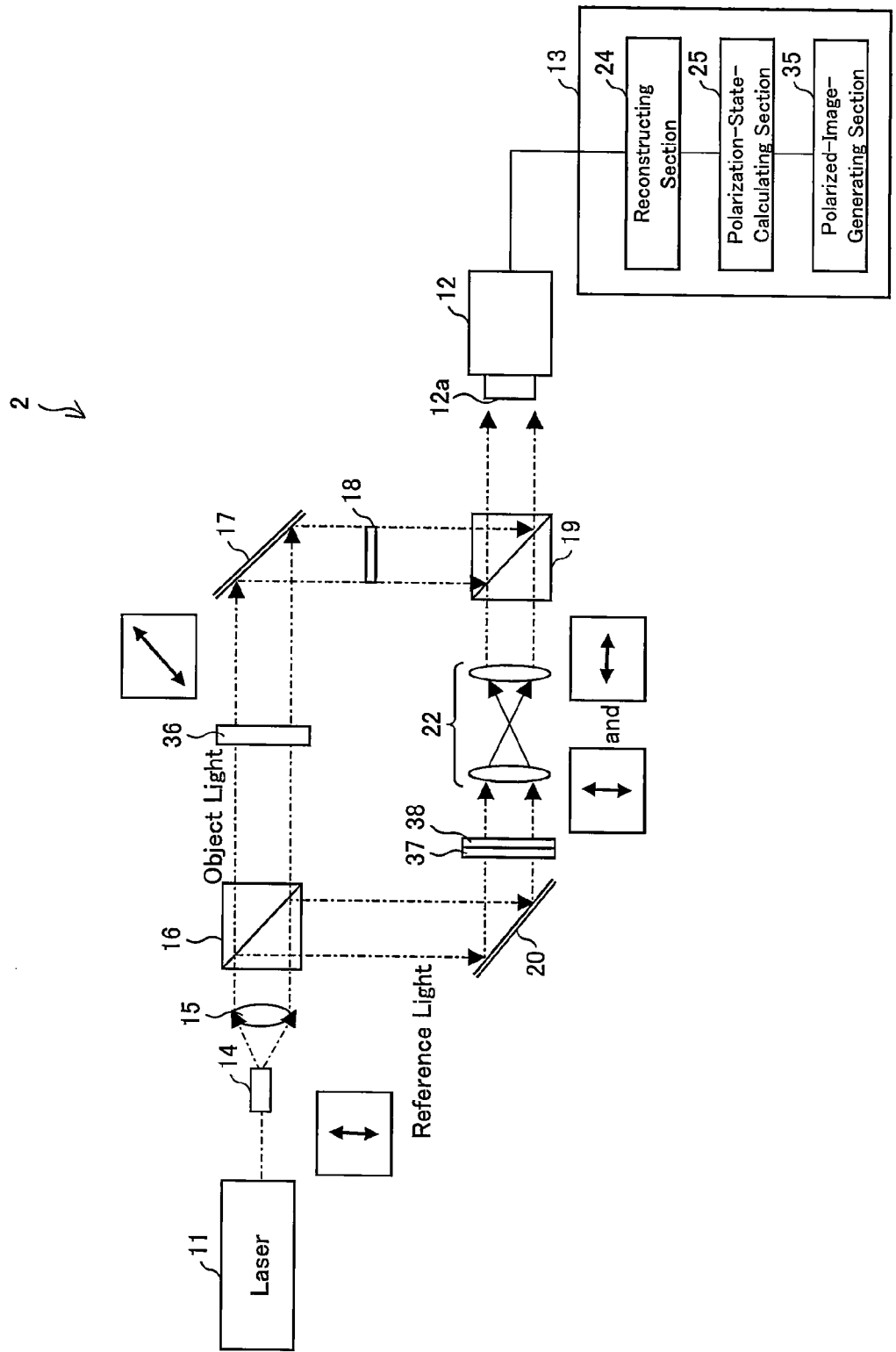

FIG. 9 is a view schematically illustrating a polarization imaging apparatus according to Embodiment 2 of the present invention.

FIG. 10

Figure 10:
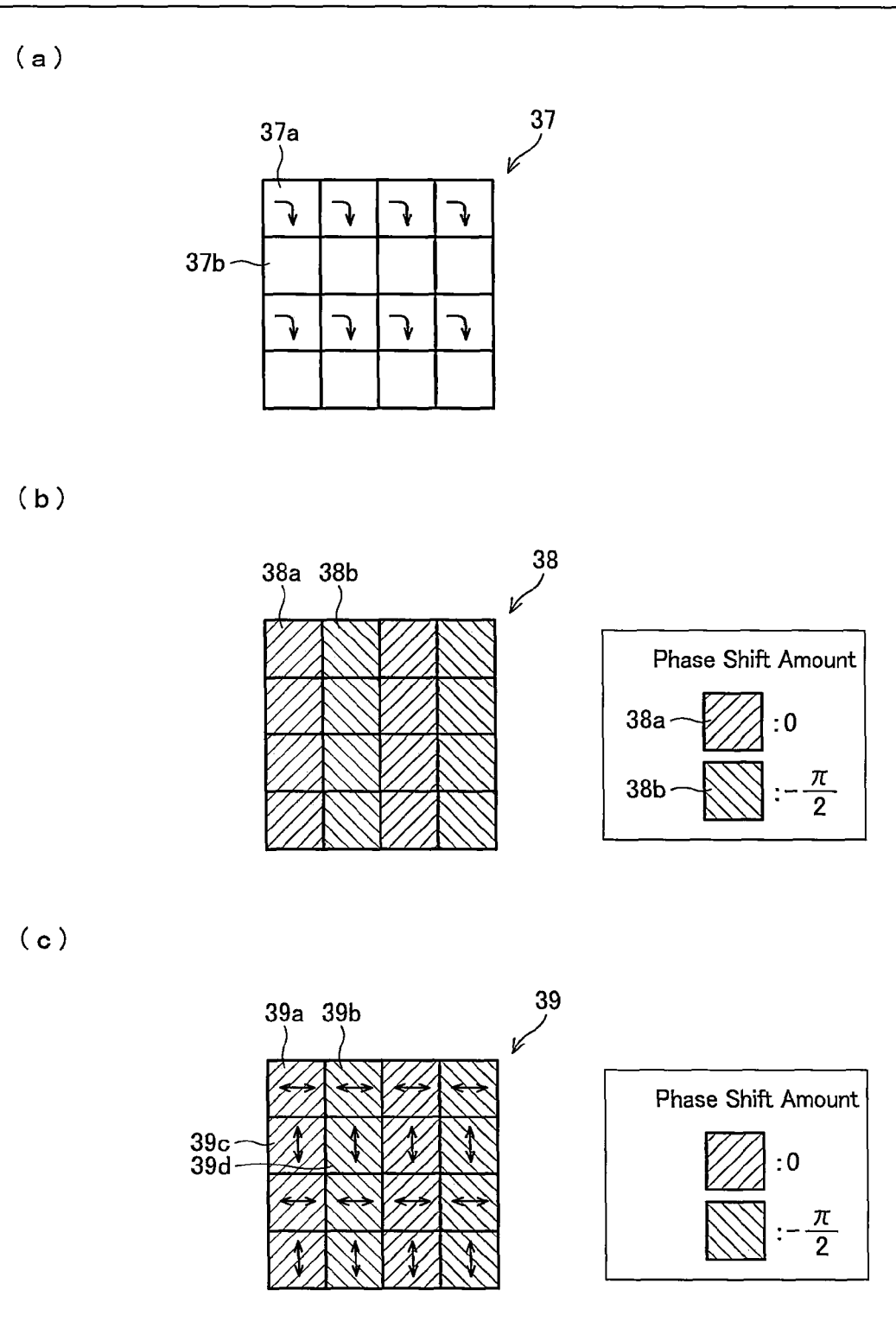

(a) of FIG. 10 is a plan view schematically illustrating a part of a first modulator; (b) of FIG. 10 is a plan view schematically illustrating a part of a second modulator; and (c) of FIG. 10 is a view schematically illustrating a state of a part of reference light that has just passed through the second modulator.

Figure 11:
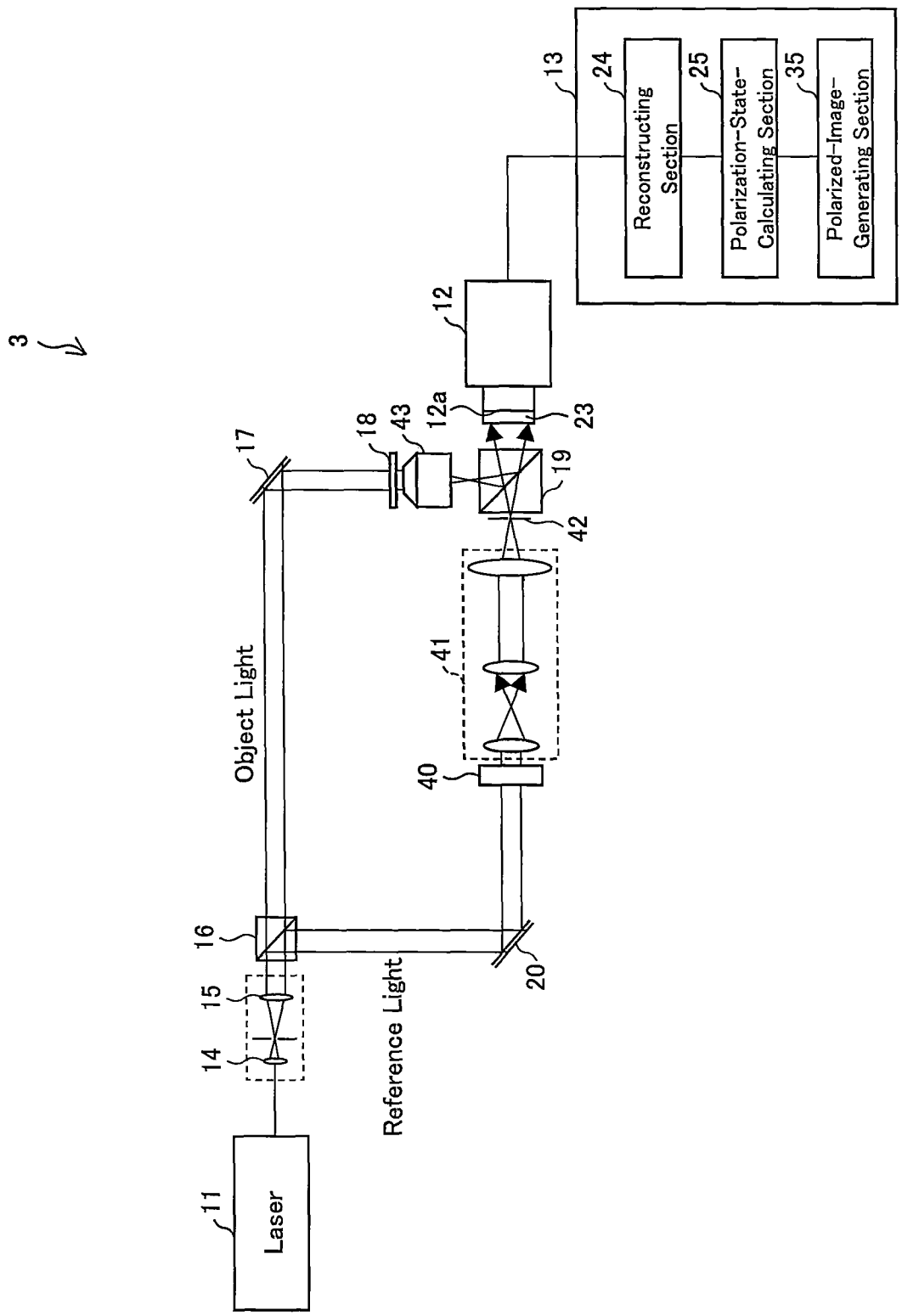

FIG. 11 is a view schematically illustrating a configuration of a polarization imaging apparatus of Embodiment 3 of the present invention.

Figure 12:
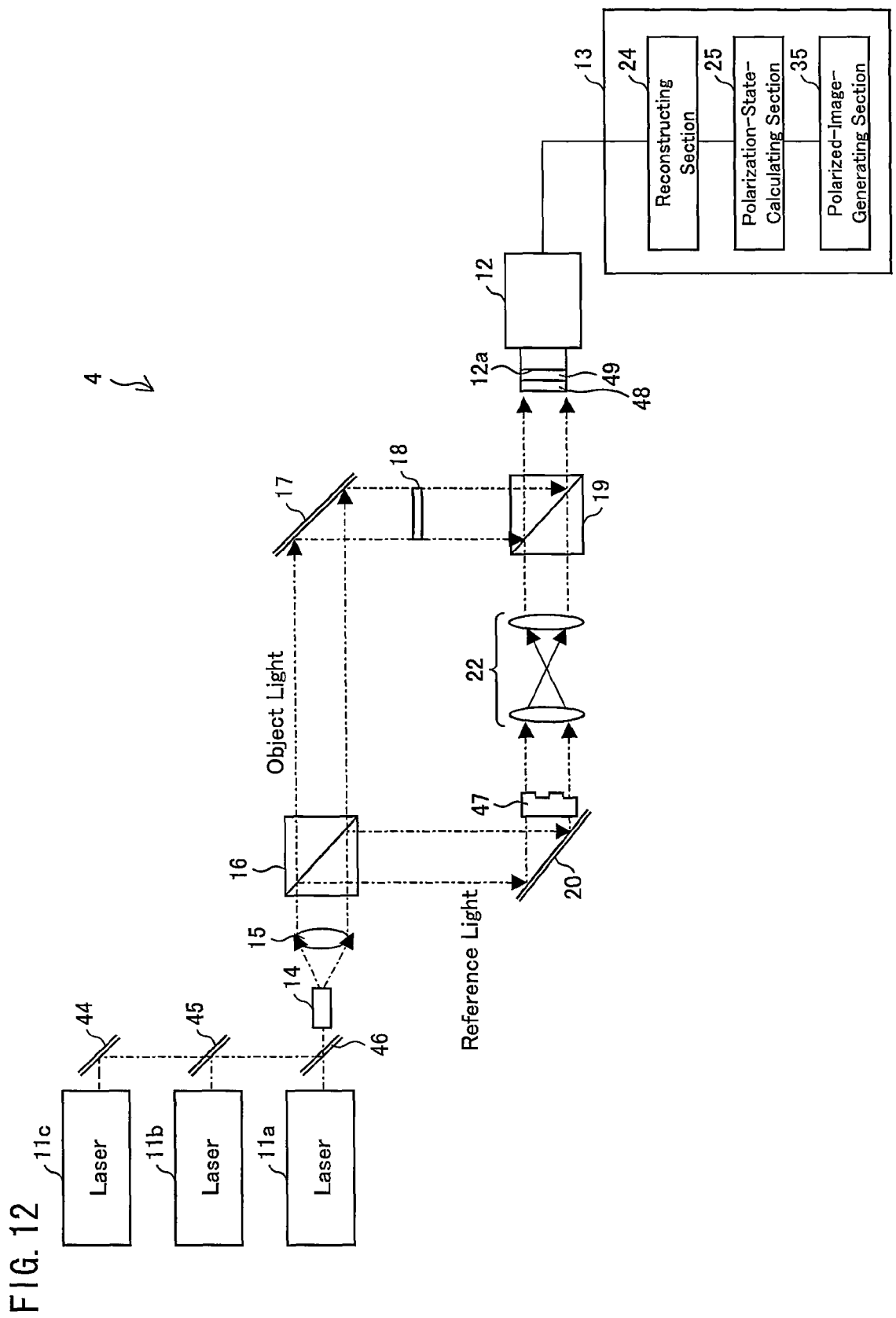

FIG. 12 is a view schematically illustrating a configuration of a polarization imaging apparatus of Embodiment 4 of the present invention.

Figure 13:
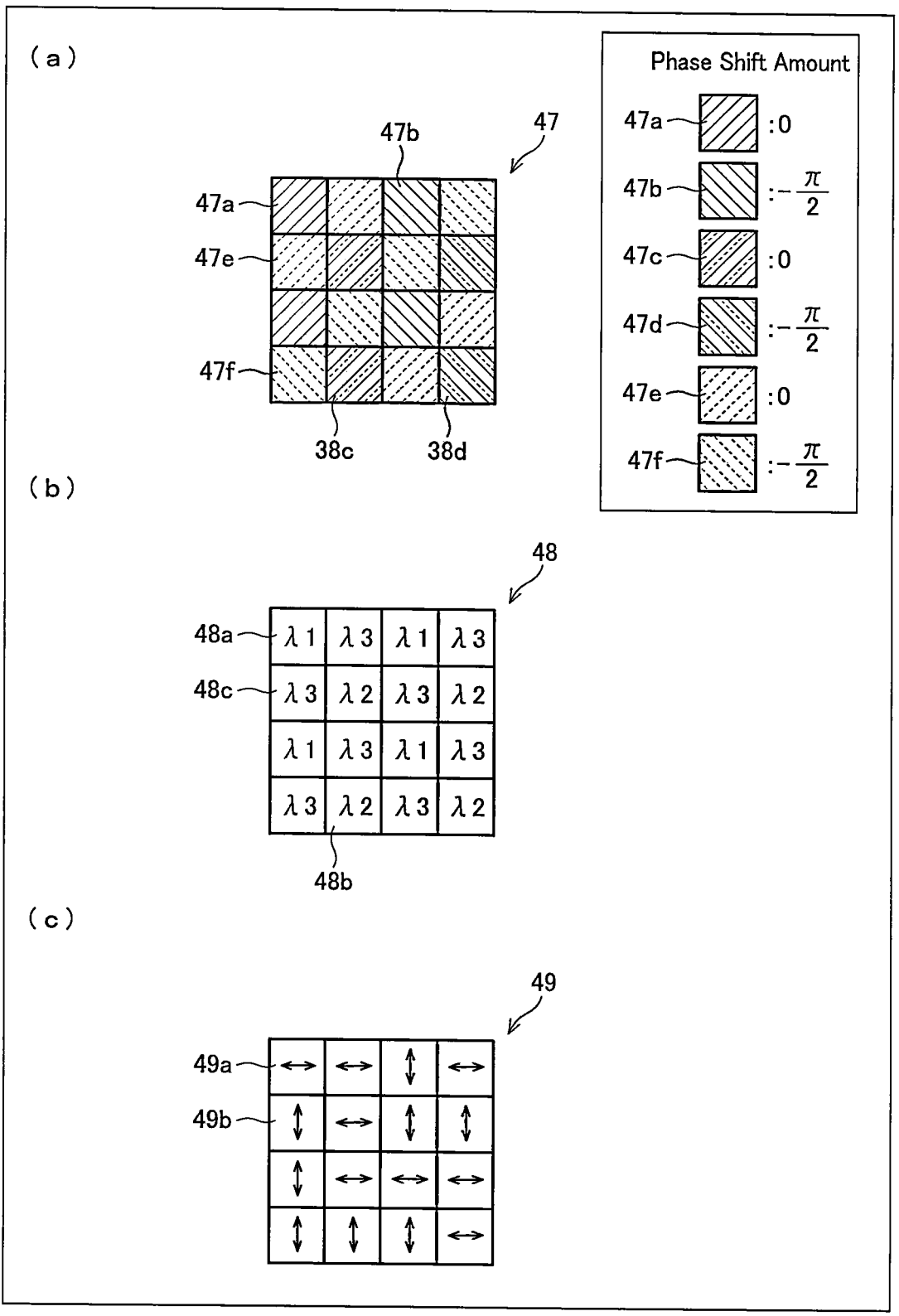

(a) of FIG. 13 is a view schematically illustrating a part of a phase-shift-array device; (b) of FIG. 13 is a view schematically illustrating a part of a wavelength selection filter; and (c) of FIG. 13 is a view schematically illustrating a part of a polarizer-array device.

Figure 14:
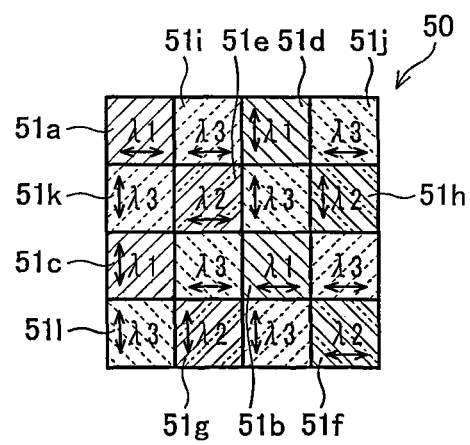

FIG. 14 illustrates a part of an interference pattern obtained by the polarization imaging apparatus.

FIG. 15

Figure 15:
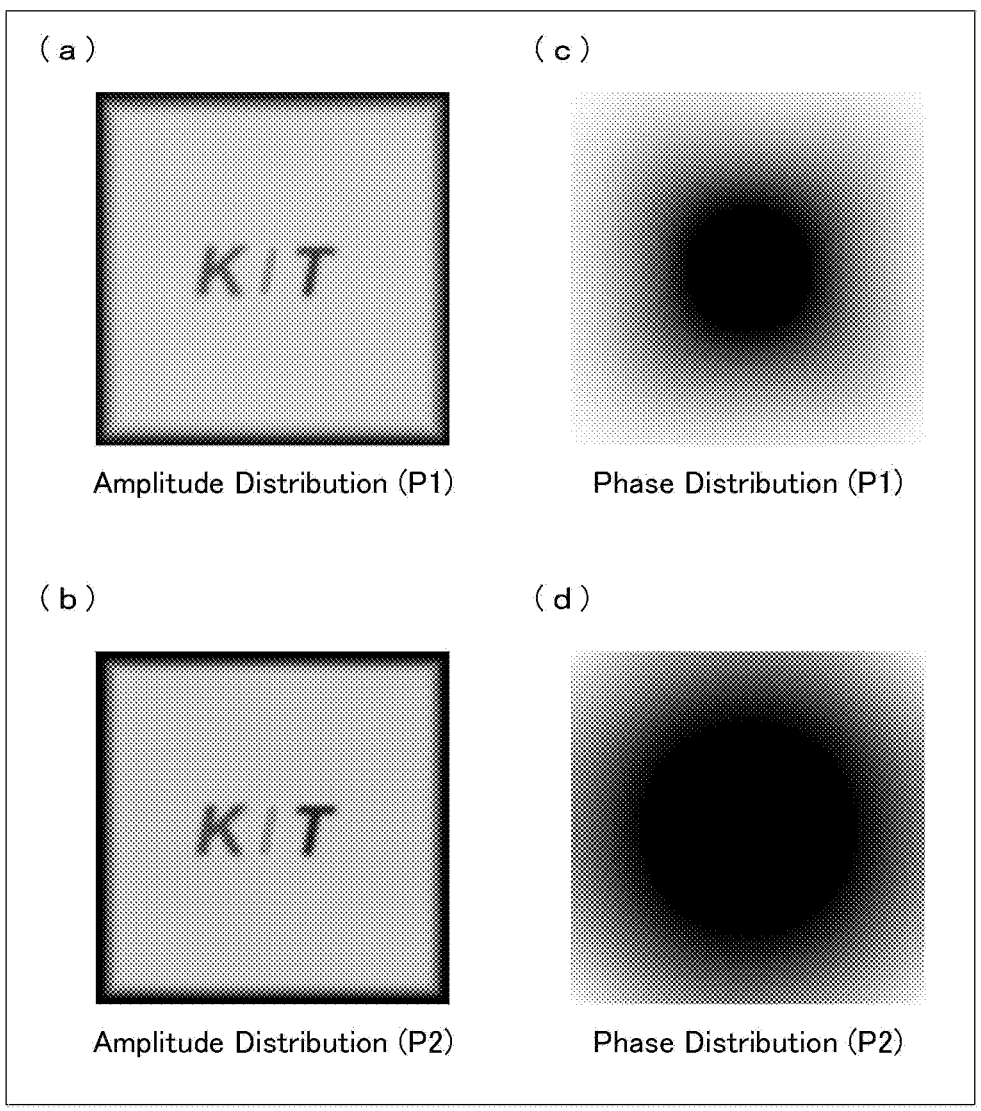

(a) of FIG. 15 shows an image of an amplitude distribution of a light component polarized in a horizontal direction (P1); (b) of FIG. 15 shows an image of an amplitude distribution of a light component polarized in a vertical direction (P2); (c) of FIG. 15 shows an image of a phase distribution in a case where a laser light polarized in the horizontal direction (P1) passes through an object; and (d) of FIG. 15 shows an image of a phase distribution in a case where a laser light polarized in the vertical direction (P2) passes through an object.

Figure 16:
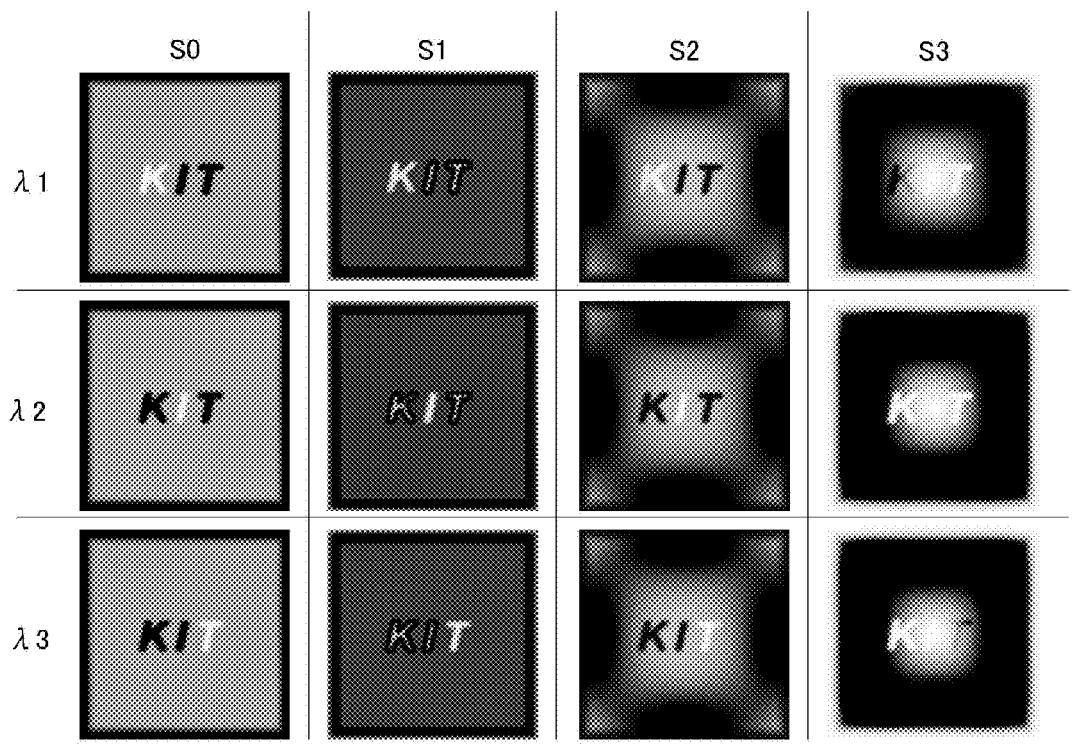

FIG. 16 shows images respectively illustrating Stokes parameters S0 to S3 for each of object light beams respectively having wavelengths λ1 to λ3.

Figure 17:
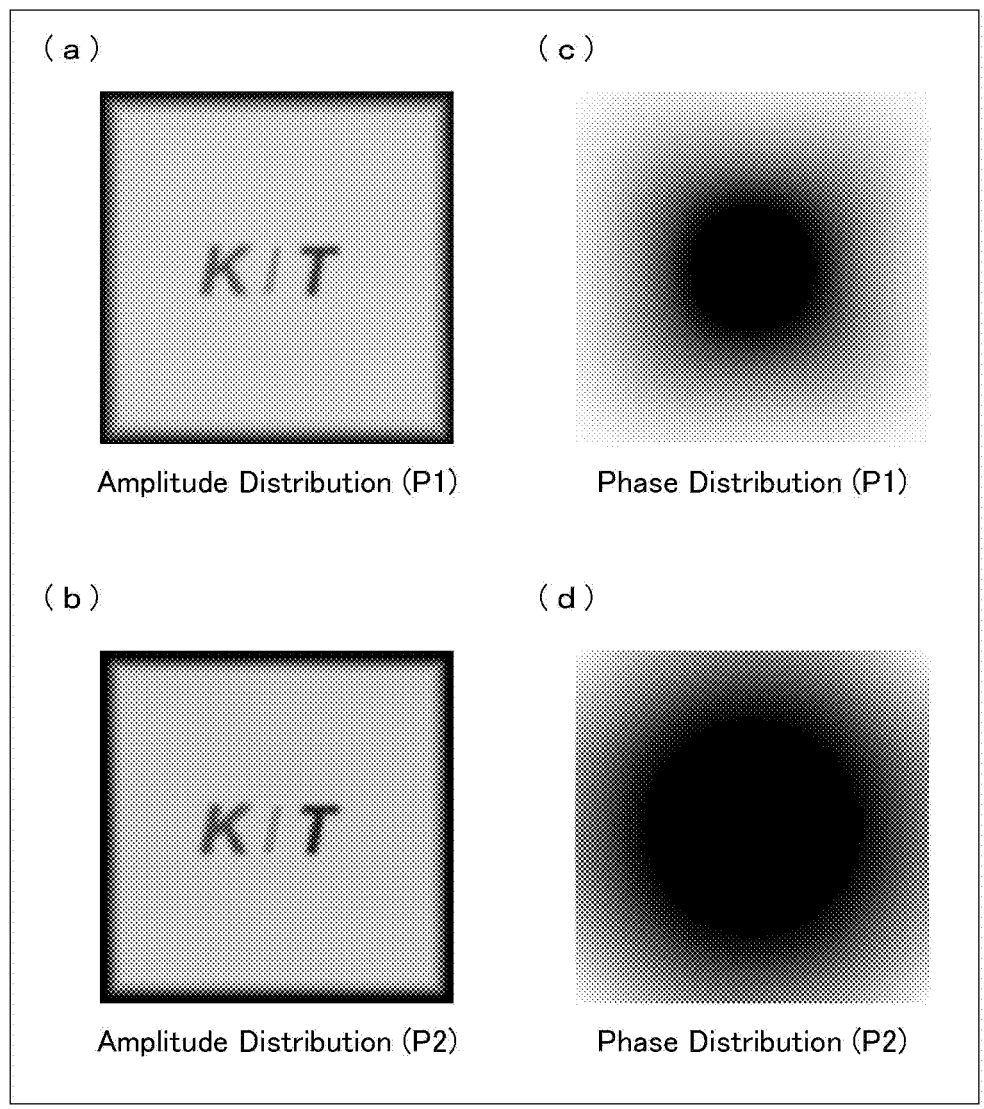

FIG. 17 shows images illustrating a result of simulation in accordance with a still another embodiment of the present invention, in regard to reconstructed images of an object.

Figure 18:
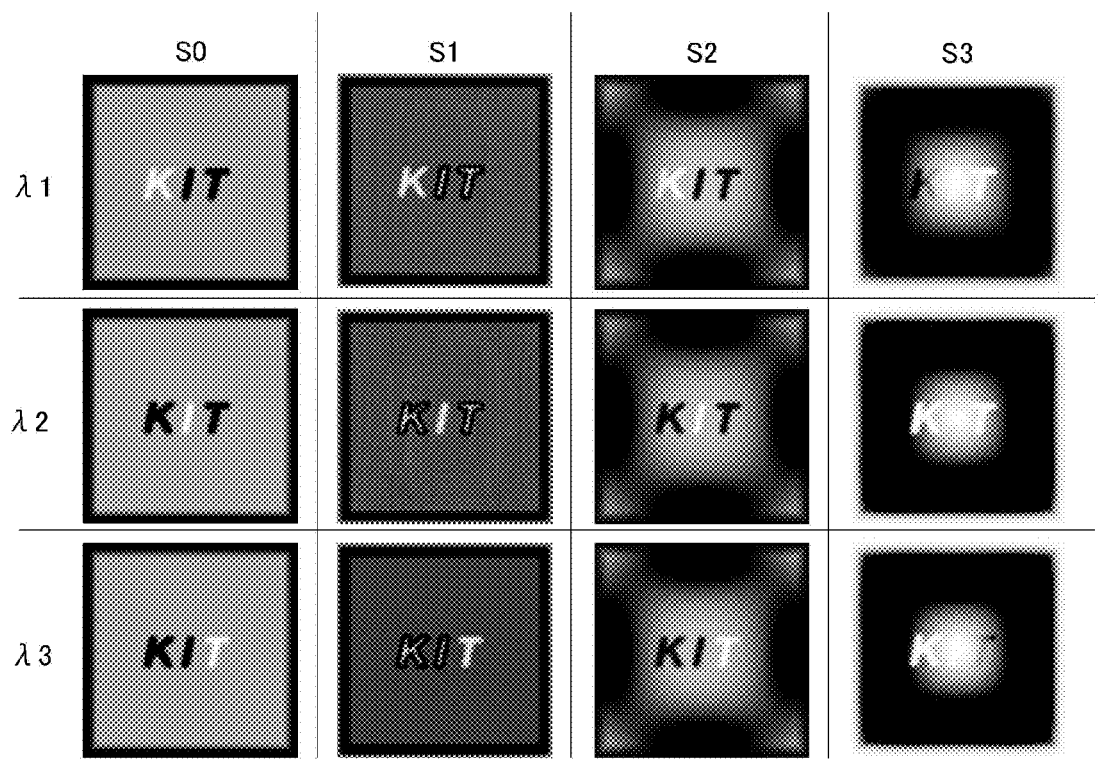

FIG. 18 shows images respectively illustrating Stokes parameters S0 to S3 for each of object light beams respectively having wavelengths λ1 to λ3 which Stokes parameters are obtained from phase distributions and the reconstructed images that result from the simulation.

Figure 19:
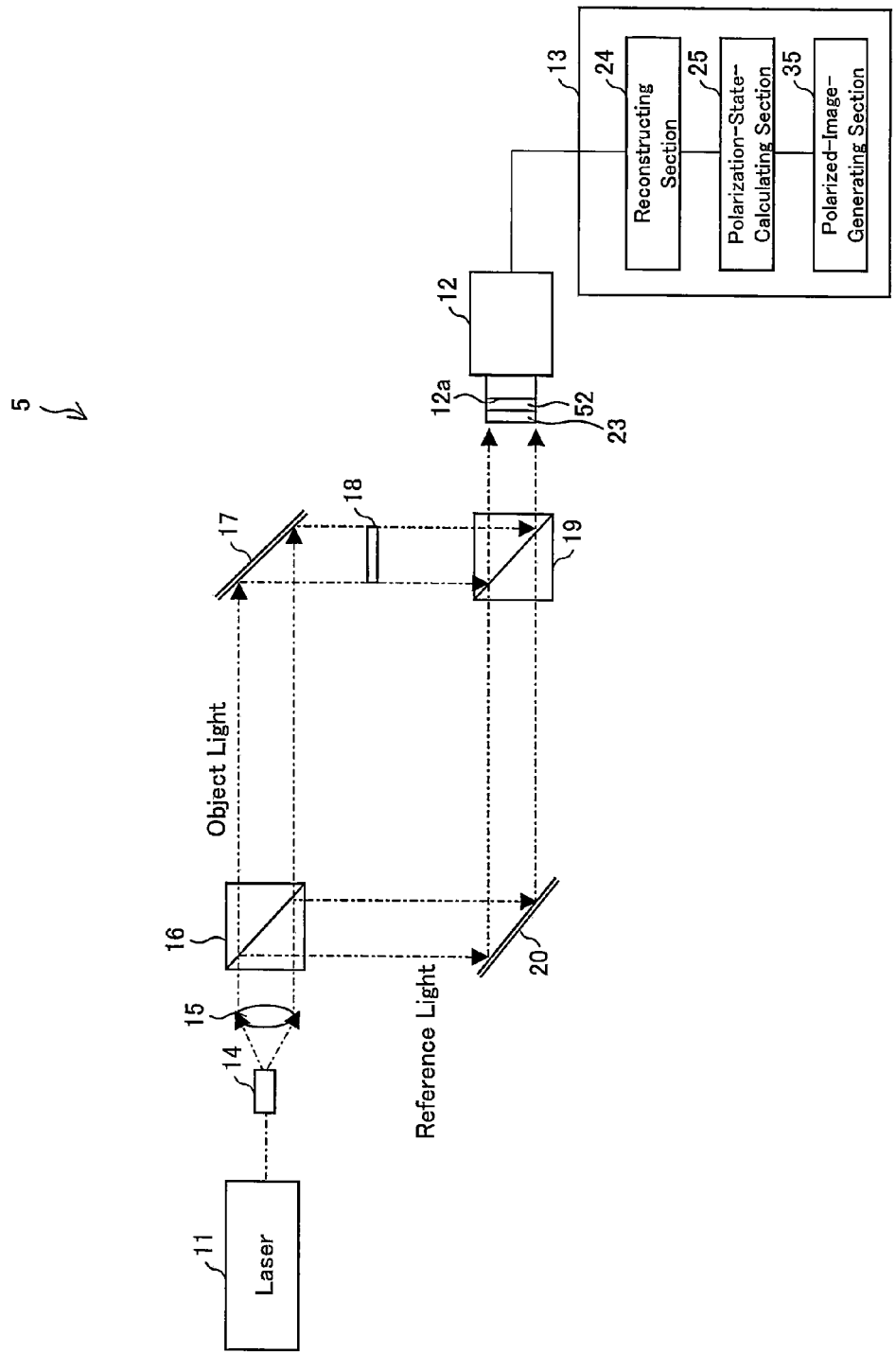

FIG. 19 is a view schematically illustrating a configuration of a polarization imaging apparatus according to Embodiment 5 of the present invention.

Figure 20:
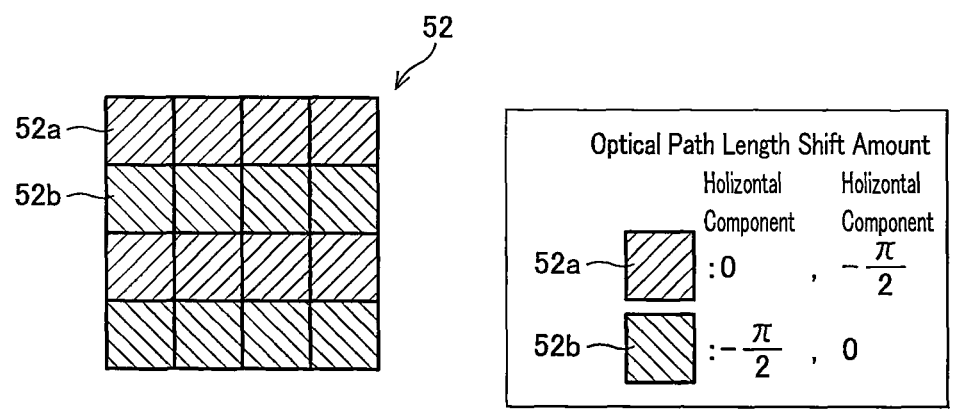

FIG. 20 is a view schematically illustrating part of an optical-path-length shift array.

Figure 21:
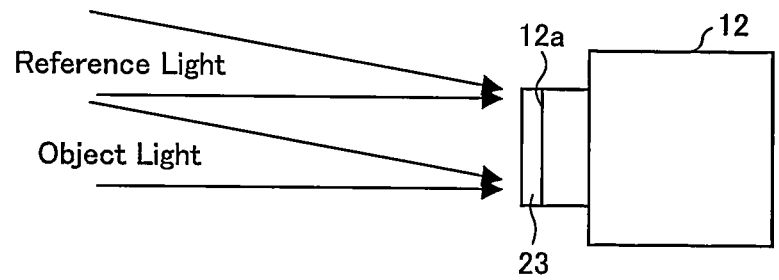

FIG. 21 is a view schematically illustrating a basic configuration of a polarization imaging apparatus according to Embodiment 6 of the present invention.

Figure 22:
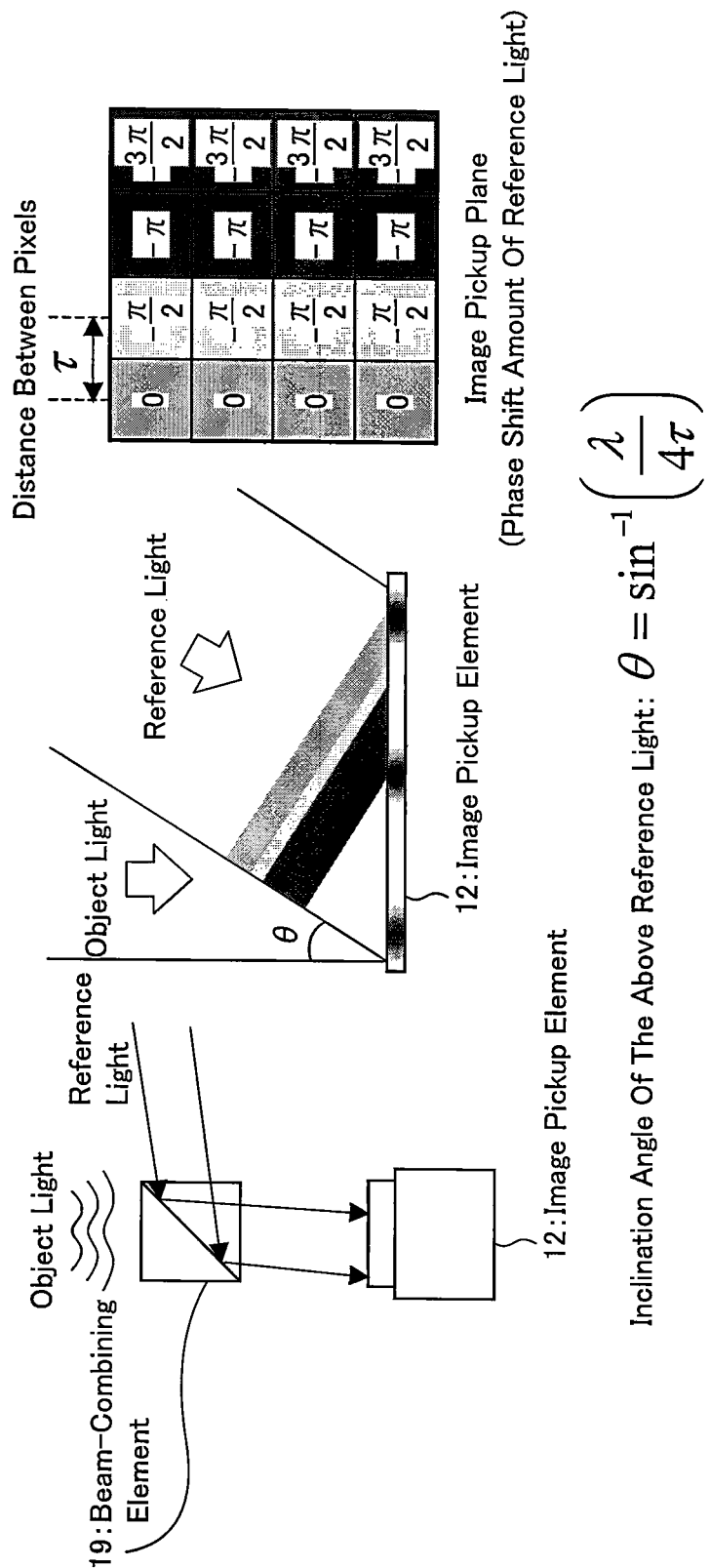

FIG. 22 illustrates an operating principle of the polarization imaging apparatus.

Figure 23:
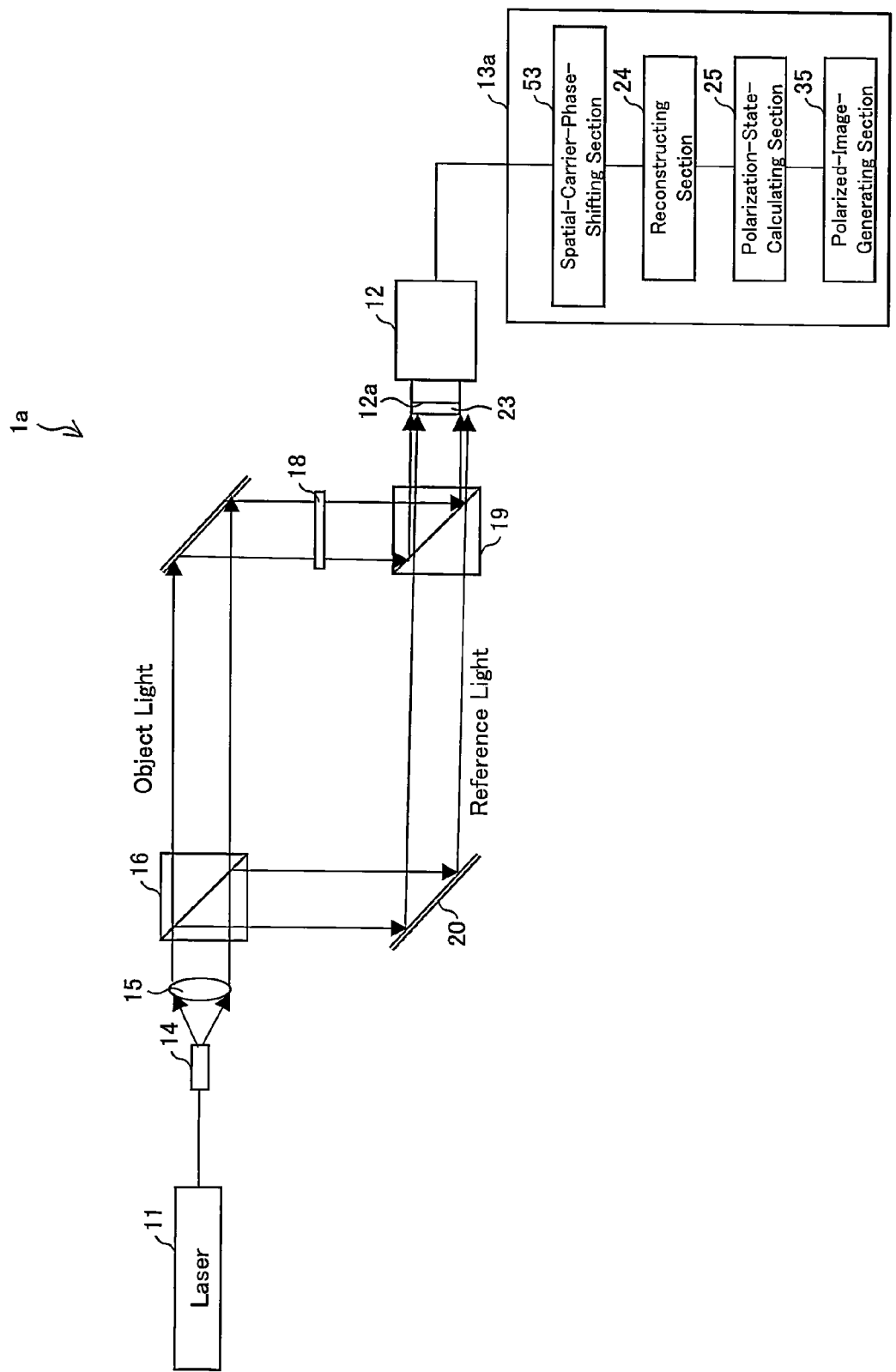

FIG. 23 is a view schematically illustrating a configuration of the polarization imaging apparatus.

Figure 24:
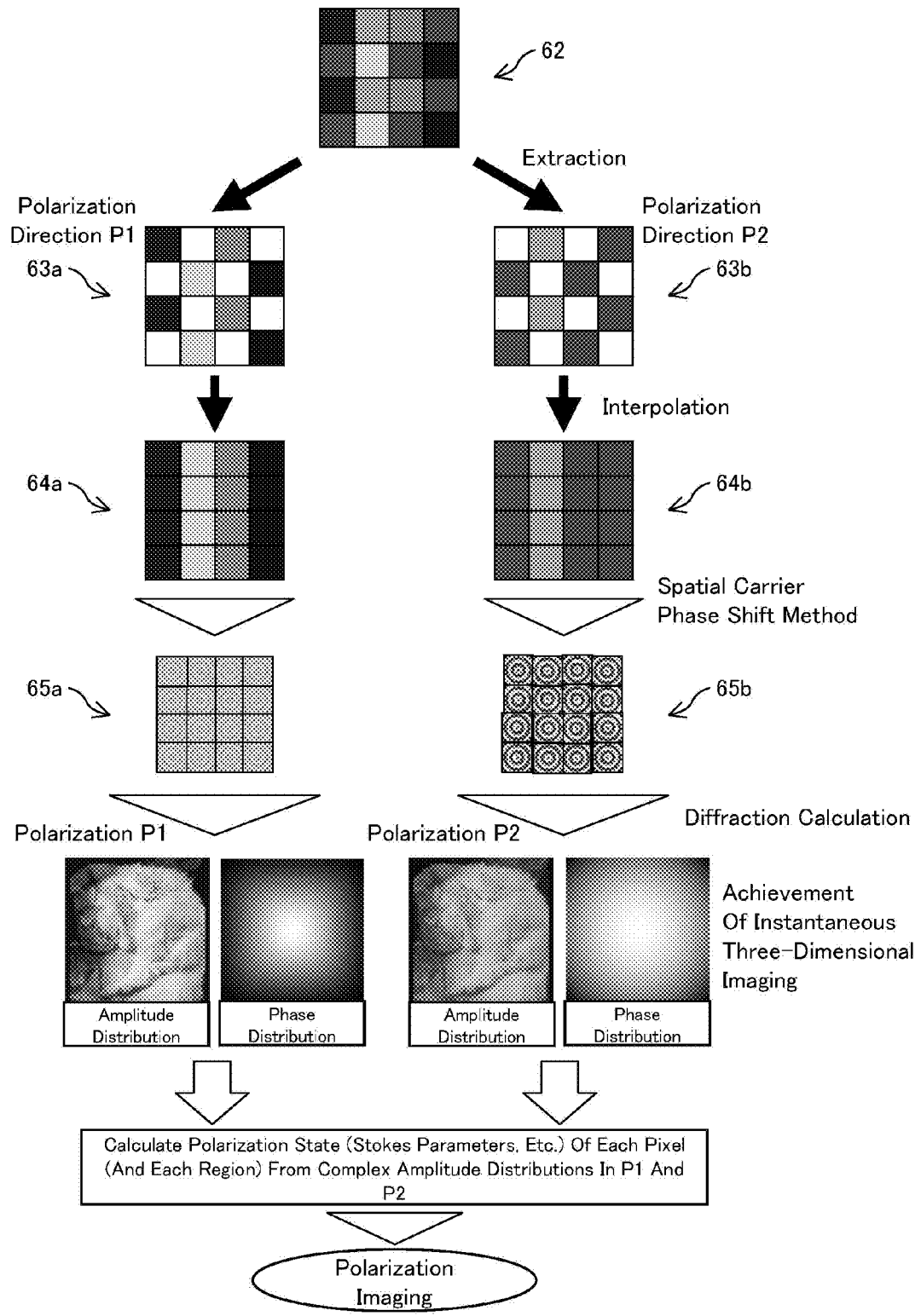

FIG. 24 illustrates an algorithm for operations of the polarization imaging apparatus.

Figure 25:
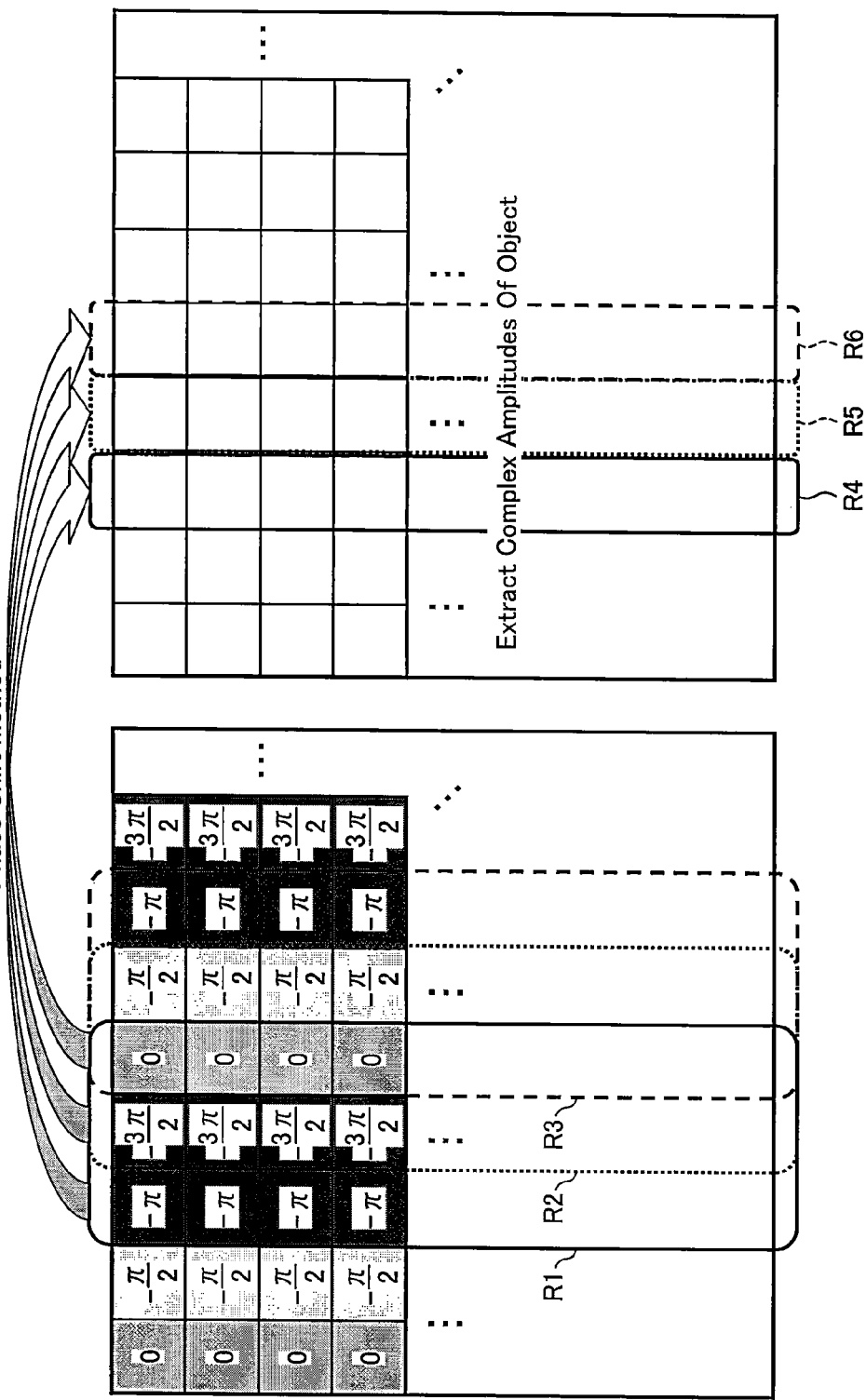

FIG. 25 illustrates a spatial carrier phase shift method based on the algorism.

Figure 26:
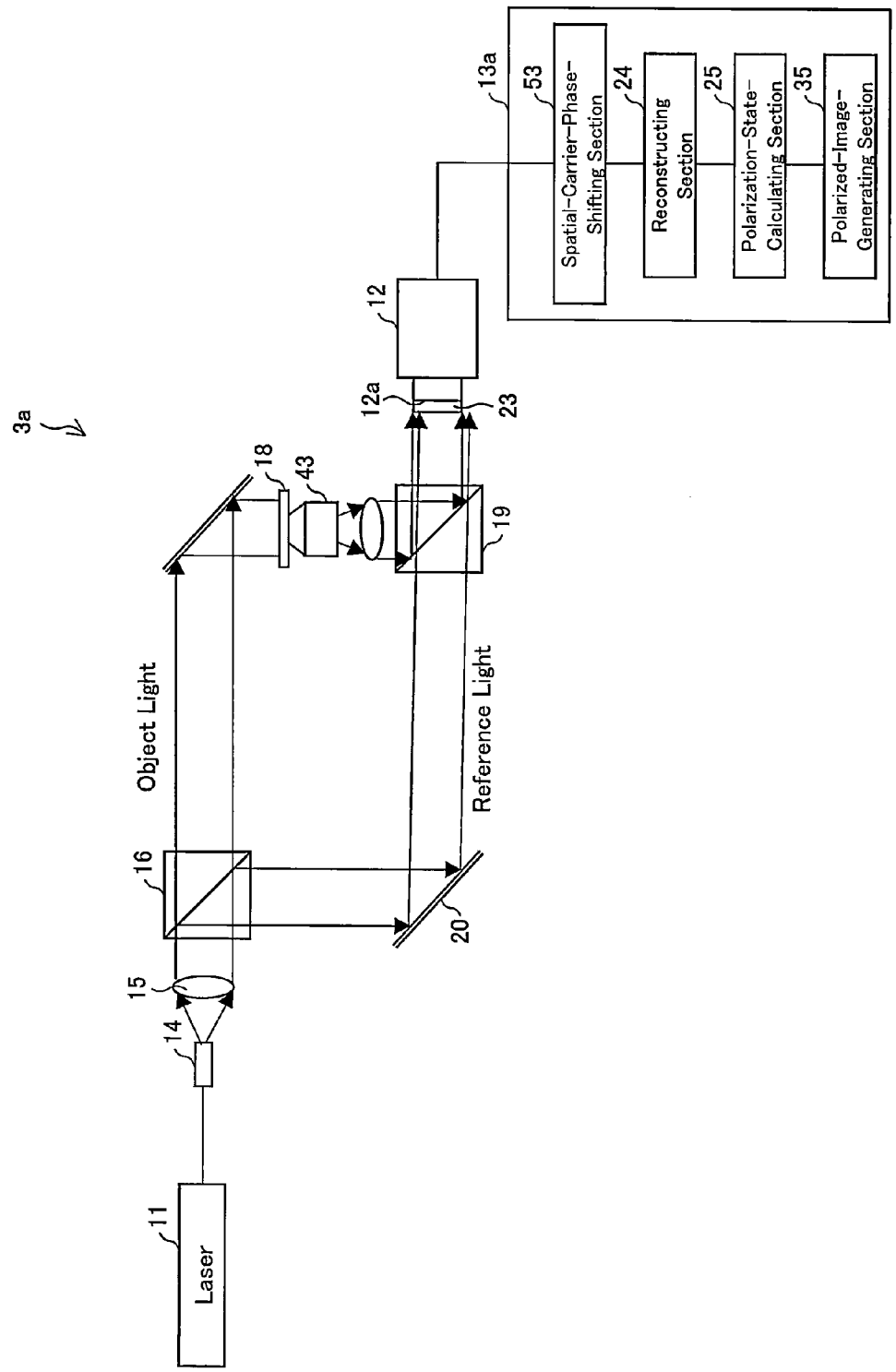

FIG. 26 is a view schematically illustrating another polarization imaging apparatus according to Embodiment 6.

Figure 27:
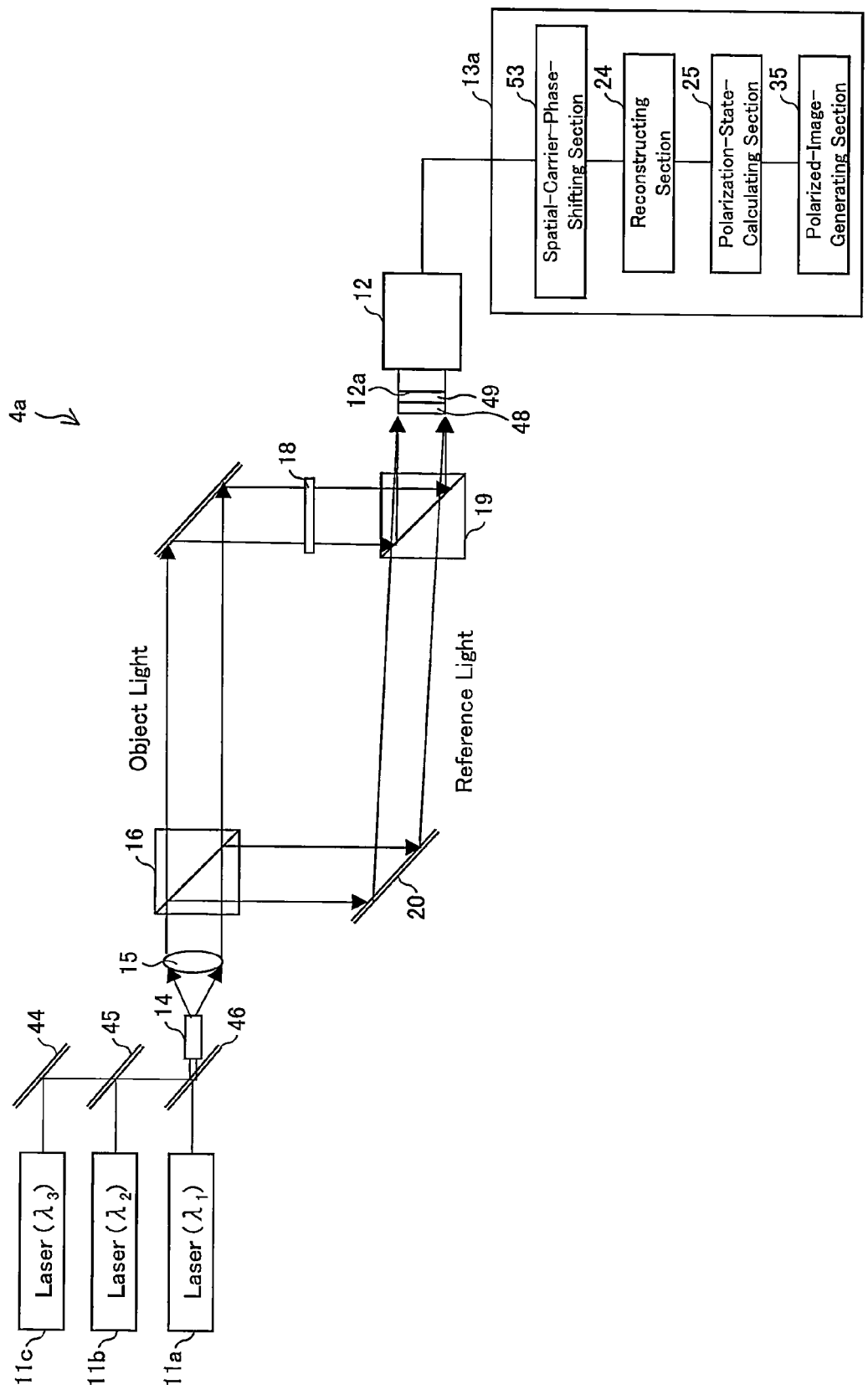

FIG. 27 is a view schematically illustrating still another polarization imaging apparatus according to Embodiment 6.

Figure 28:
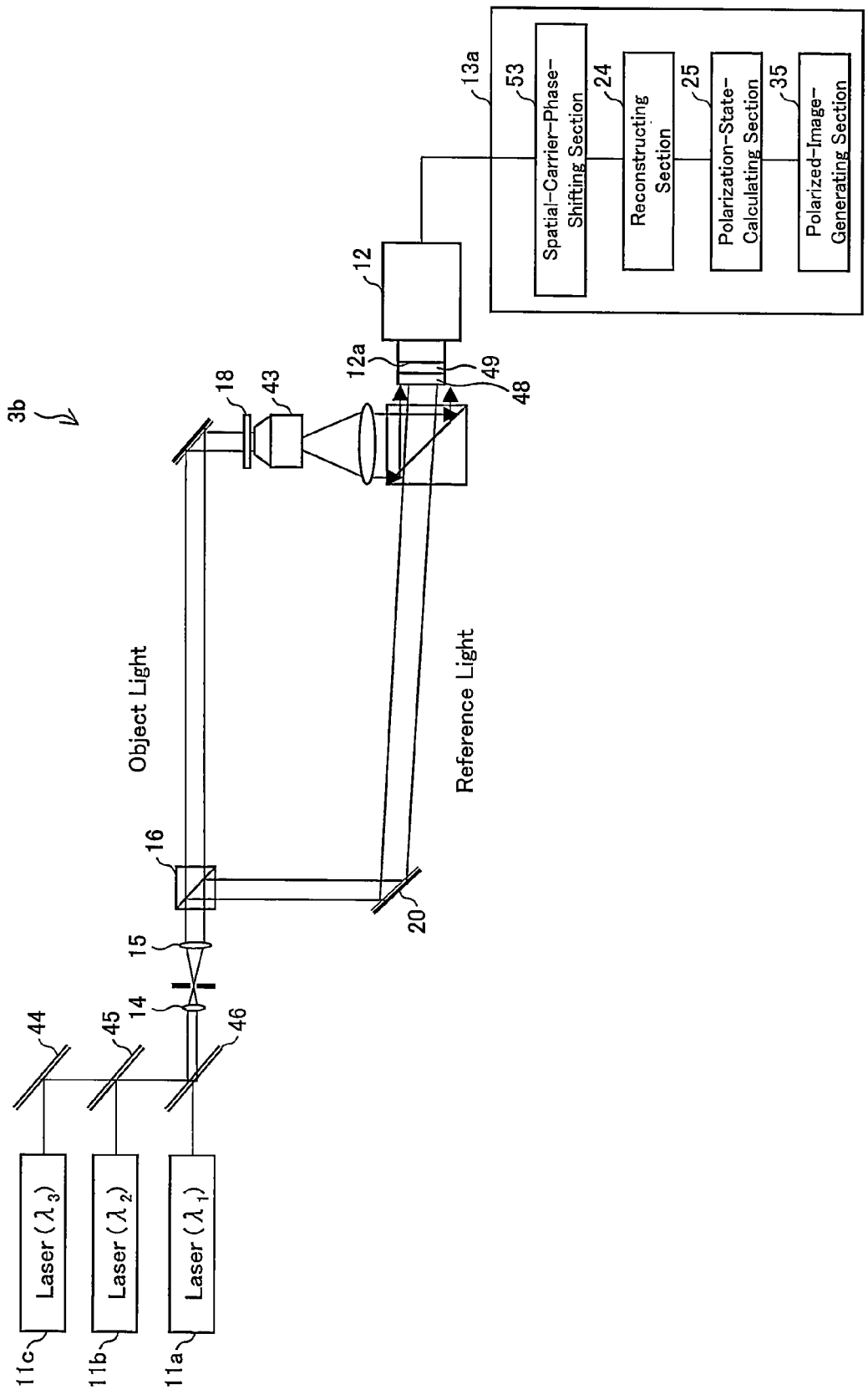

FIG. 28 is a view schematically illustrating yet another polarization imaging apparatus according to Embodiment 6.

FIG. 29

Figure 29:
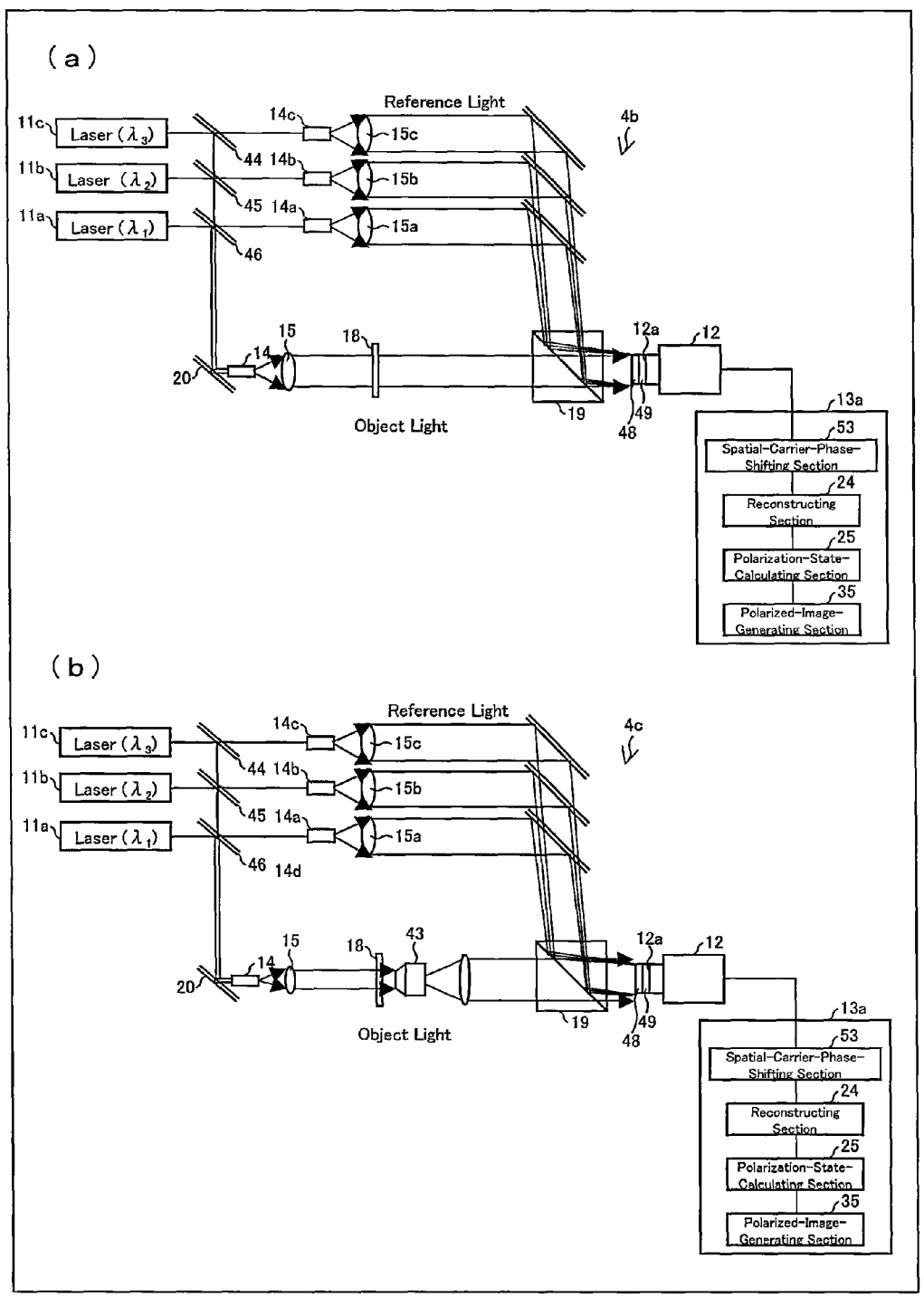

(a) and (b) of FIG. 29 are views schematically illustrating a still further polarization imaging apparatuses according to Embodiment 6.

FIG. 30

Figure 30:
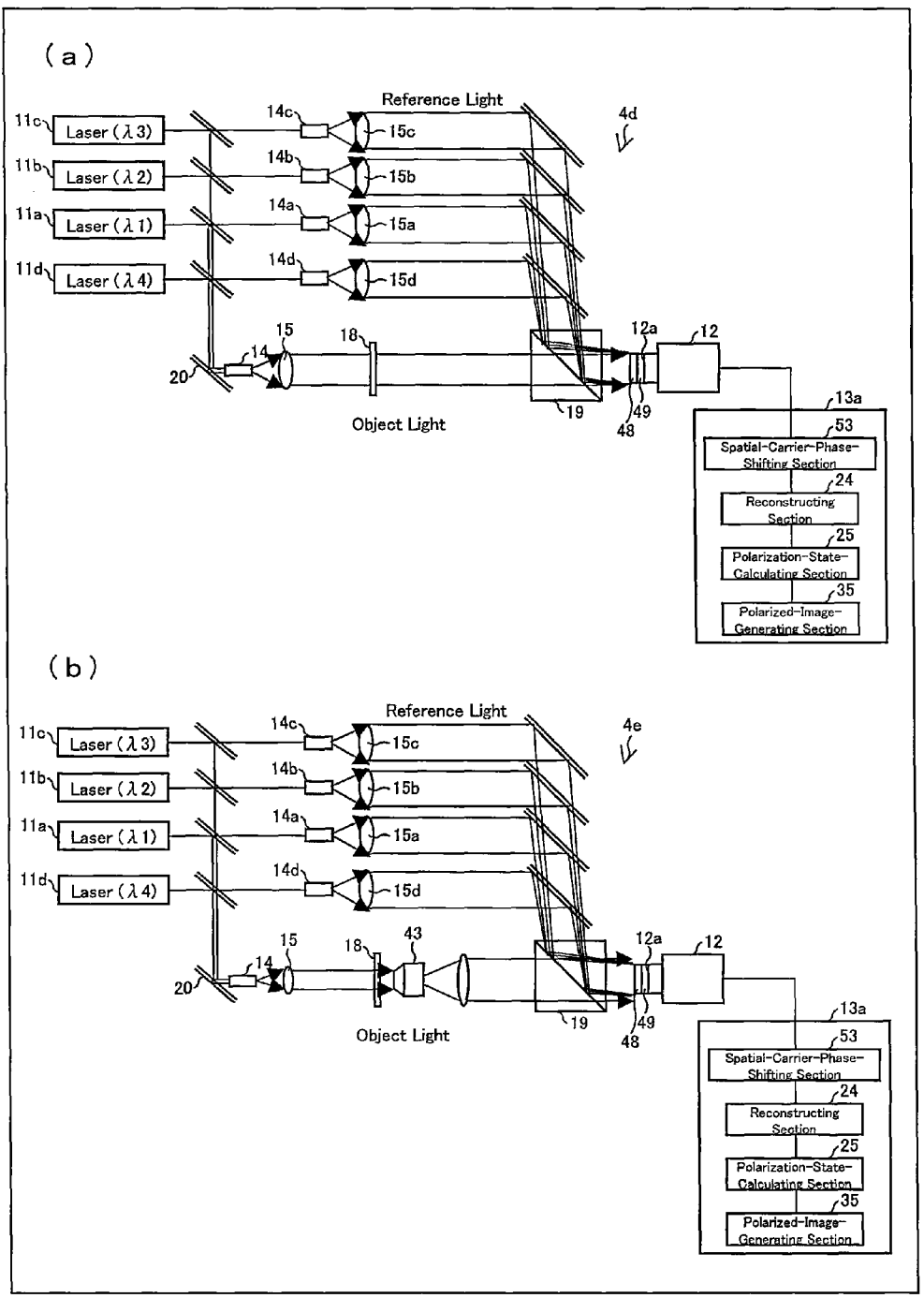

(a) and (b) of FIG. 30 are views schematically illustrating a yet further polarization imaging apparatuses according to Embodiment 6.

Figure 31:
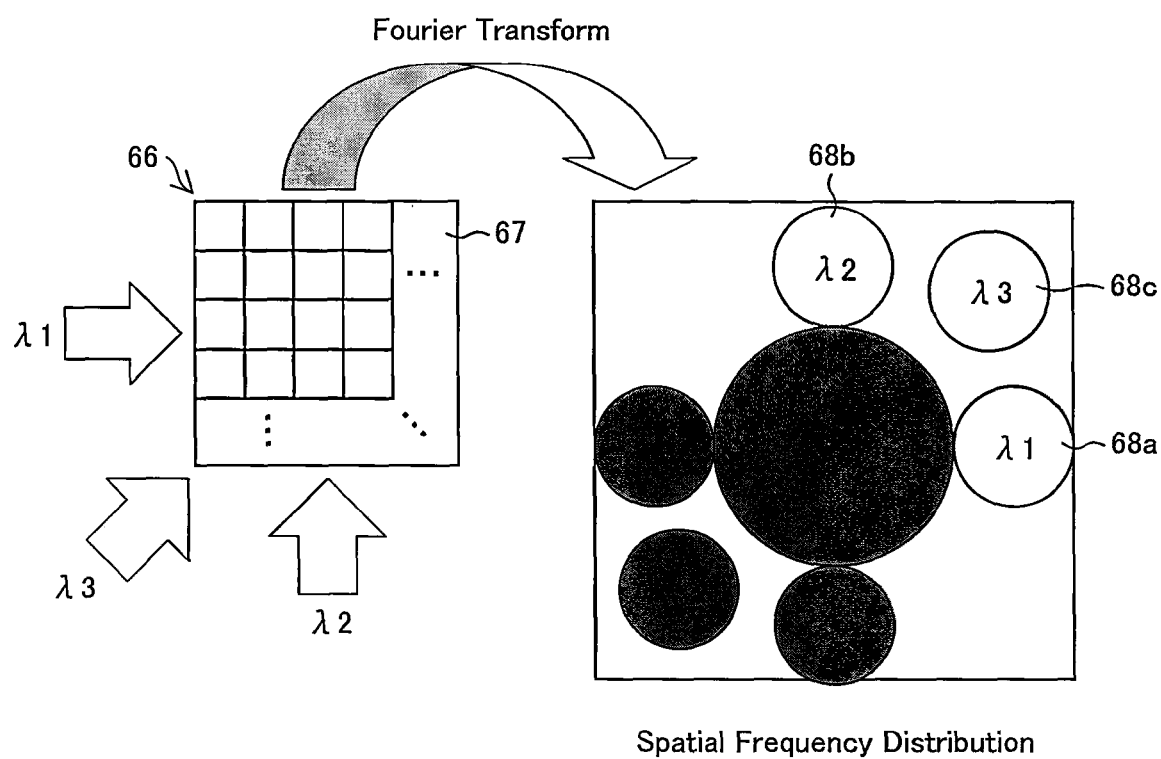

FIG. 31 illustrates a method for obtaining plural pieces of wavelength information with use of a single-type image sensor.

Figure 32:
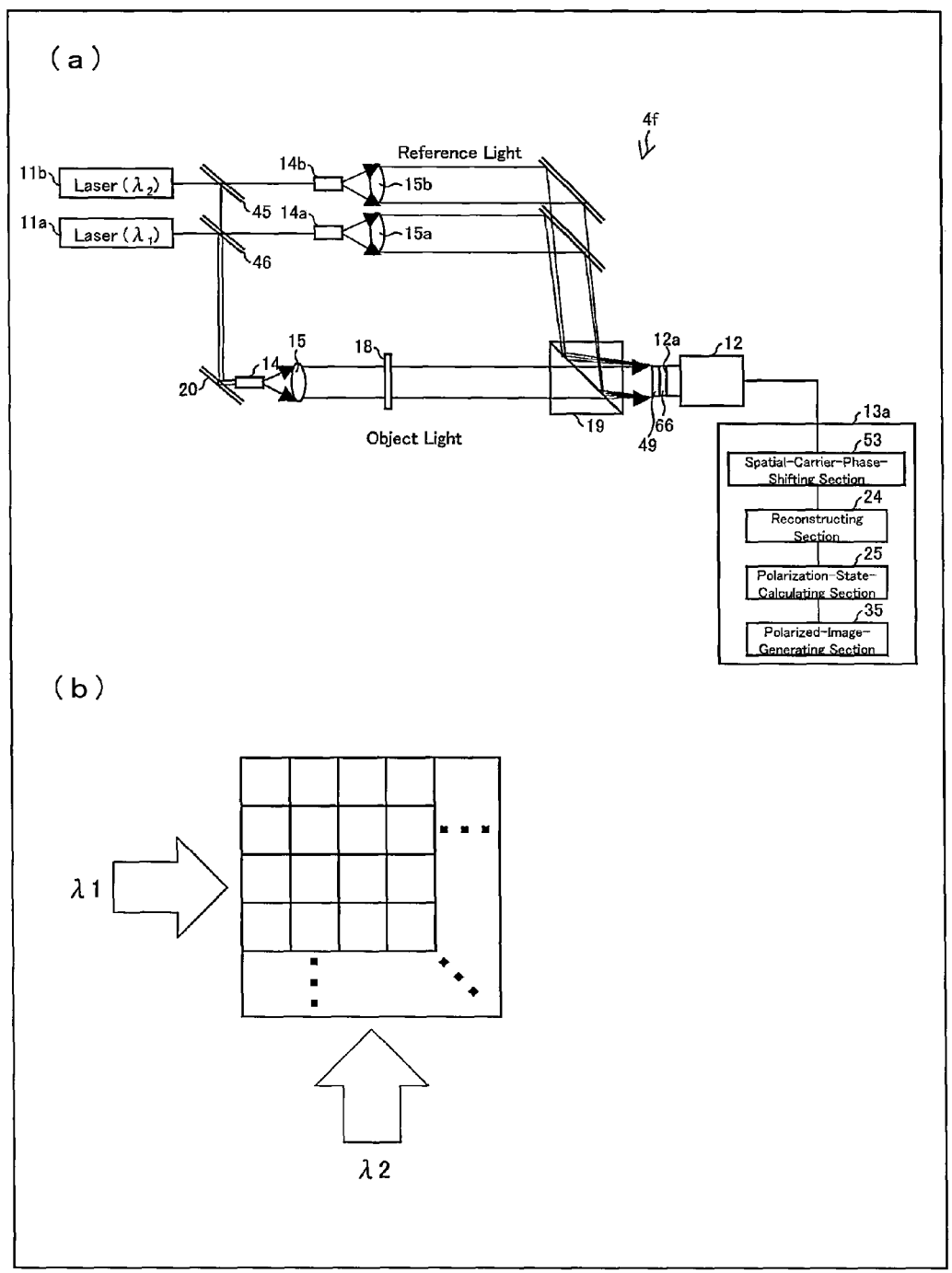

(a) of FIG. 32 is a view schematically illustrating the configuration of another polarization imaging apparatus according to Embodiment 6; and (b) of FIG. 32 illustrates a method for obtaining three-dimensional information, polarization information, and plural pieces of wavelength information with use of a single-type image sensor.

Figure 33:
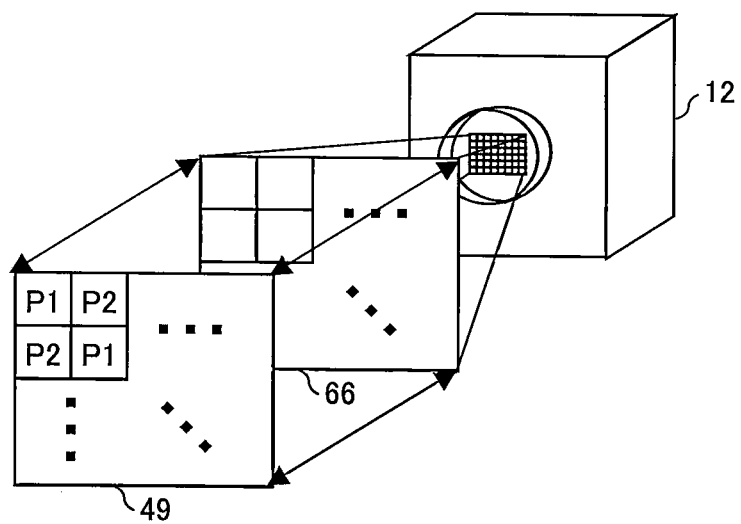

FIG. 33 is an oblique view illustrating a configuration of an image pickup element for obtaining three-dimensional information, polarization information, and plural pieces of wavelength information with use of a single-type image sensor.

Figure 34:
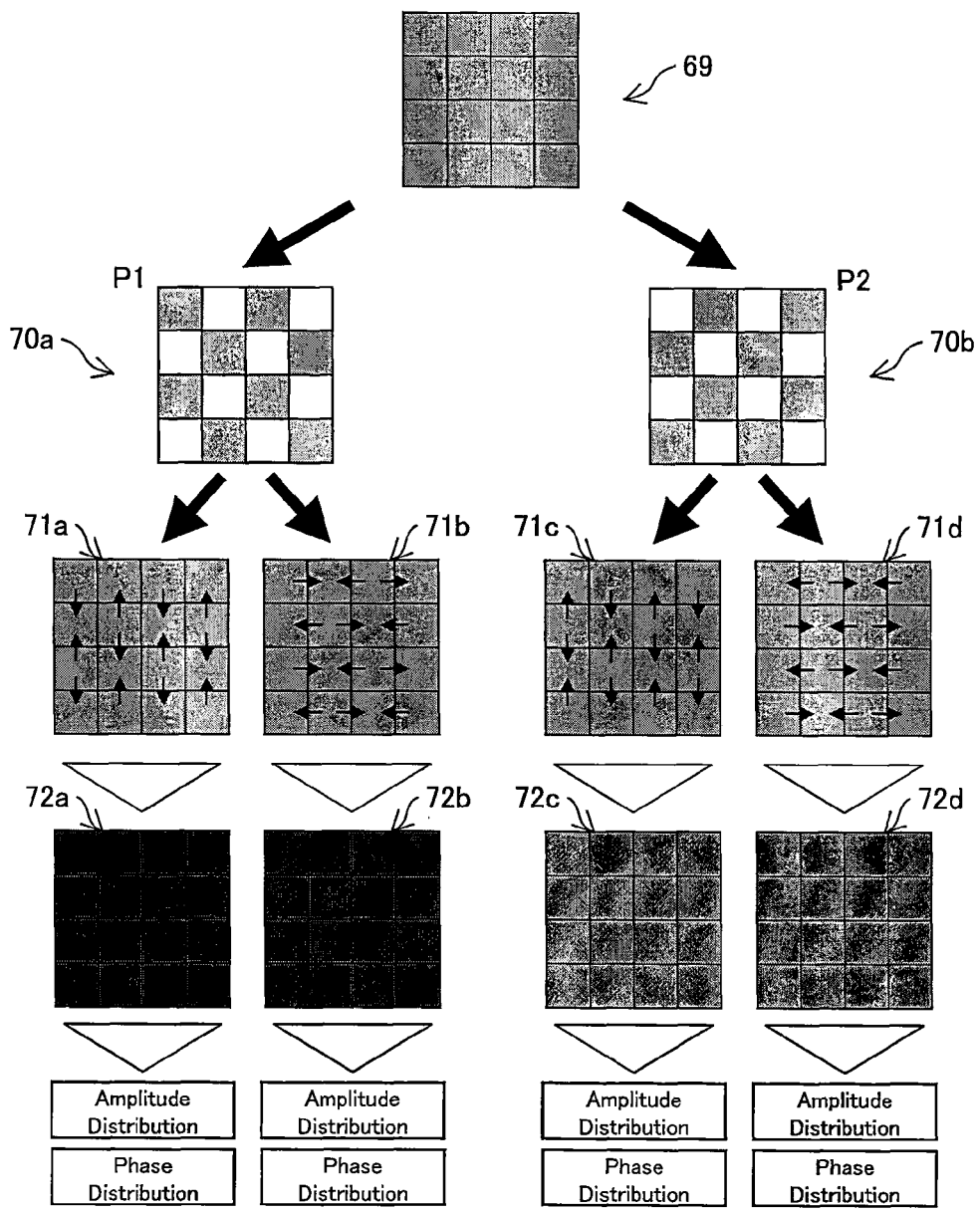

FIG. 34 is a view illustrating a flow for obtaining three-dimensional images of an object corresponding to varying combinations of a plurality of polarizations and a plurality of wavelengths from a recorded hologram.

Figure 35:
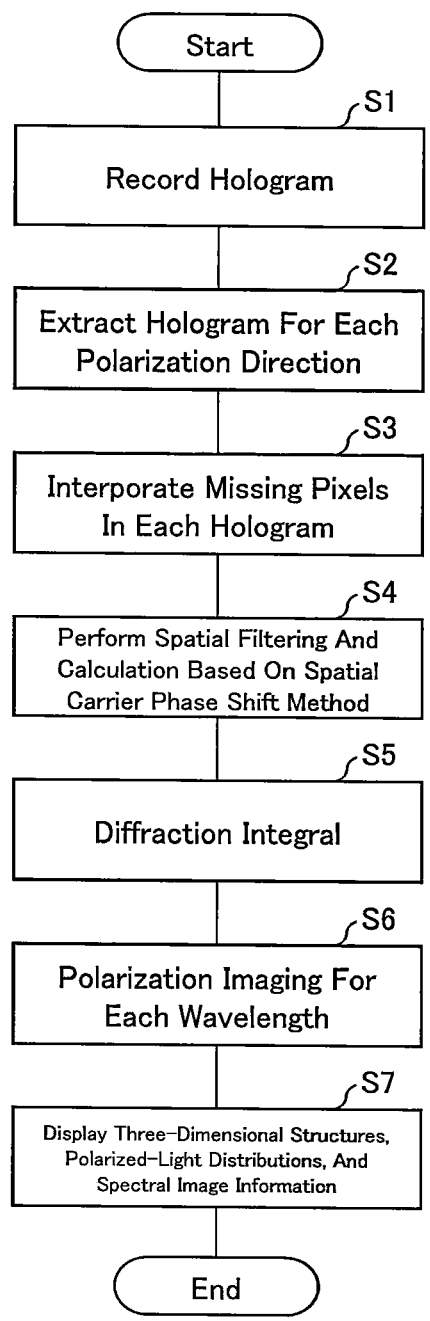

FIG. 35 is a flow chart illustrating a flow for reconstructing three-dimensional structures, polarized-light distributions, and spectral images of an object from a recorded hologram.

FIG. 36

(a) of FIG. 36 is a view illustrating a configuration of a wavelength-selection-filter array including two types of filters; and (b) of FIG. 36 illustrates an operation of the wavelength-selection-filter array.

FIG. 37

Figure 37:
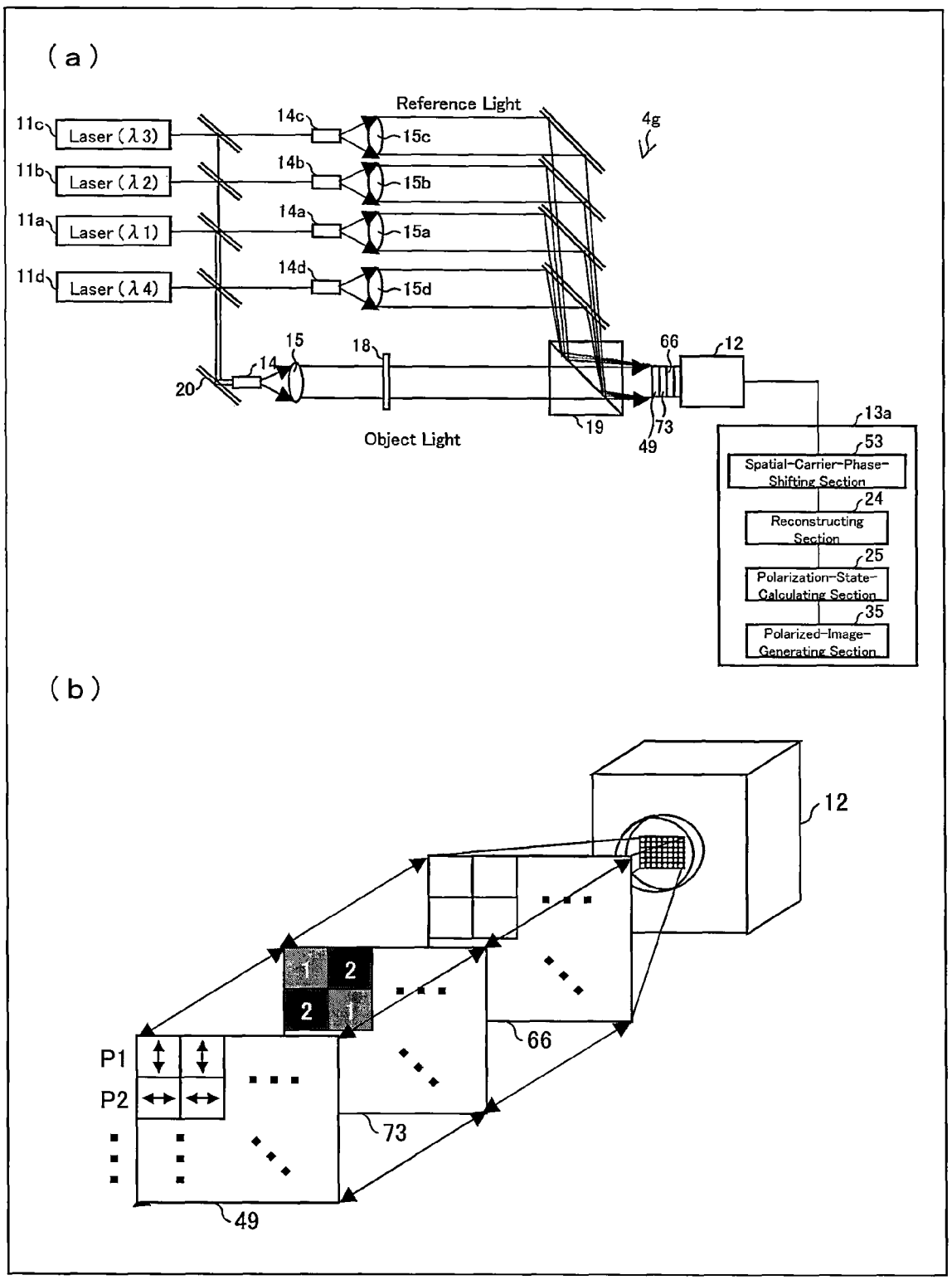

(a) of FIG. 37 is a view schematically illustrating a configuration of still another polarization imaging apparatus according to Embodiment 6; and (b) of FIG. 37 is an oblique view illustrating a configuration of an image pickup element provided in the still another polarization imaging apparatus.

Figure 38:
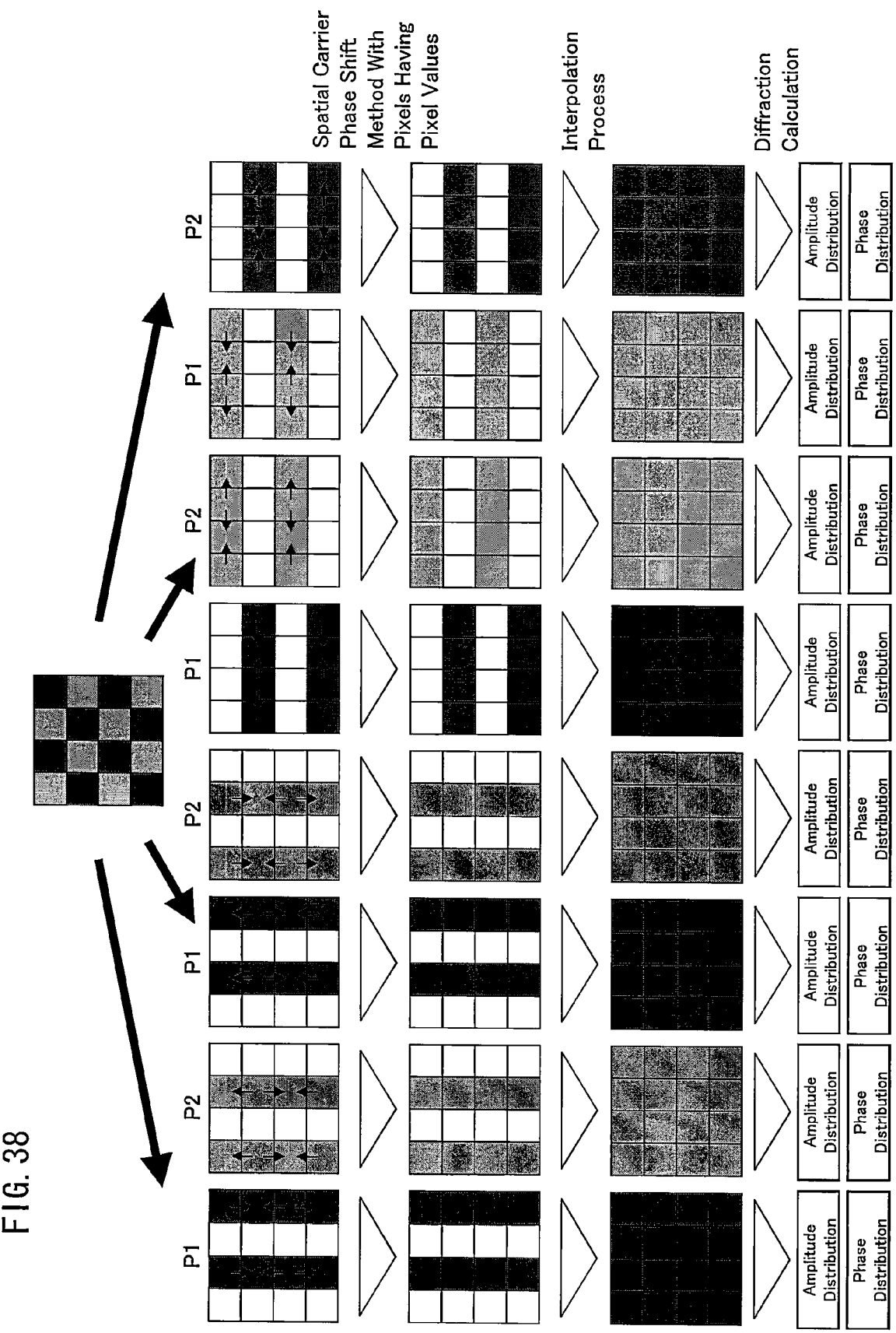

FIG. 38 is a view illustrating a flow for obtaining three-dimensional images corresponding to varying combinations of polarizations and wavelengths from a hologram having been recorded by the image pickup element.

Figure 39:
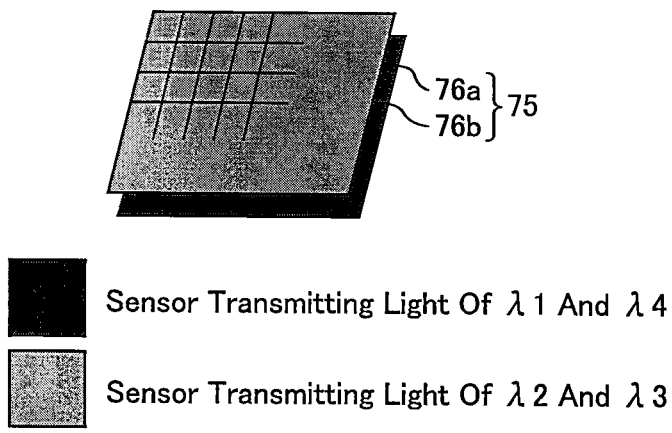

FIG. 39 is a view illustrating a configuration of a multilayered image sensor according to Embodiment 6.

Figure 40:
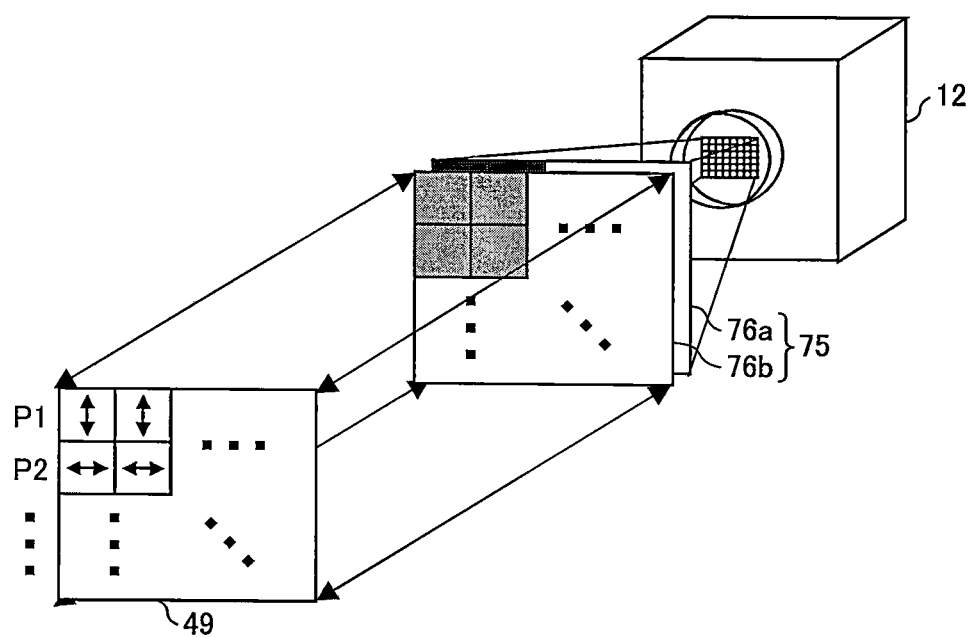

FIG. 40 is an oblique view illustrating a configuration of an image pickup element using the multilayered image sensor.

Figure 41:
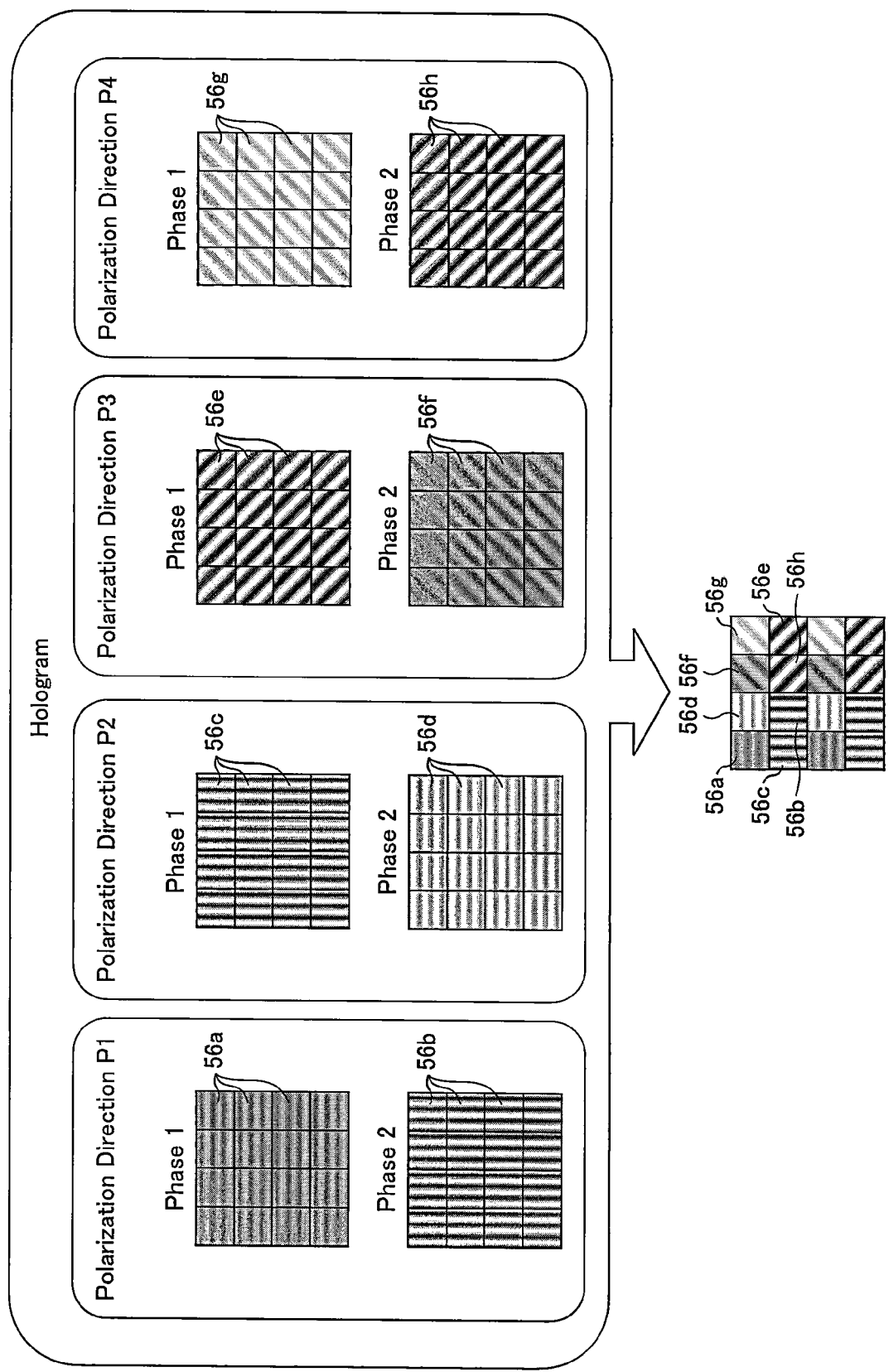

FIG. 41 illustrates a configuration of a hologram formed by an image pickup section which is provided in a polarization imaging apparatus according to Embodiment 7.

Figure 42:
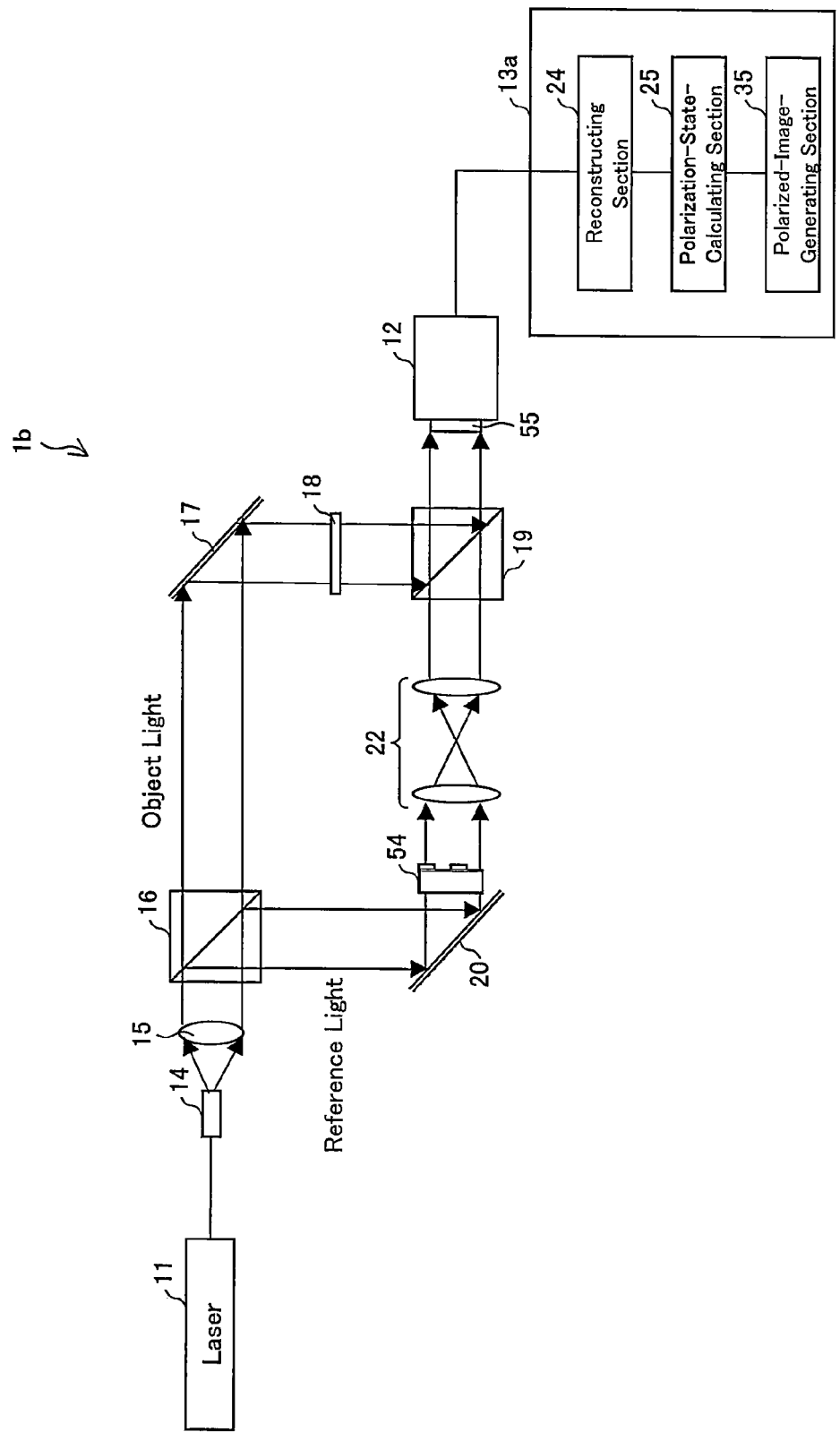

FIG. 42 is a view illustrating a configuration of the above polarization imaging apparatus.

Figure 43:
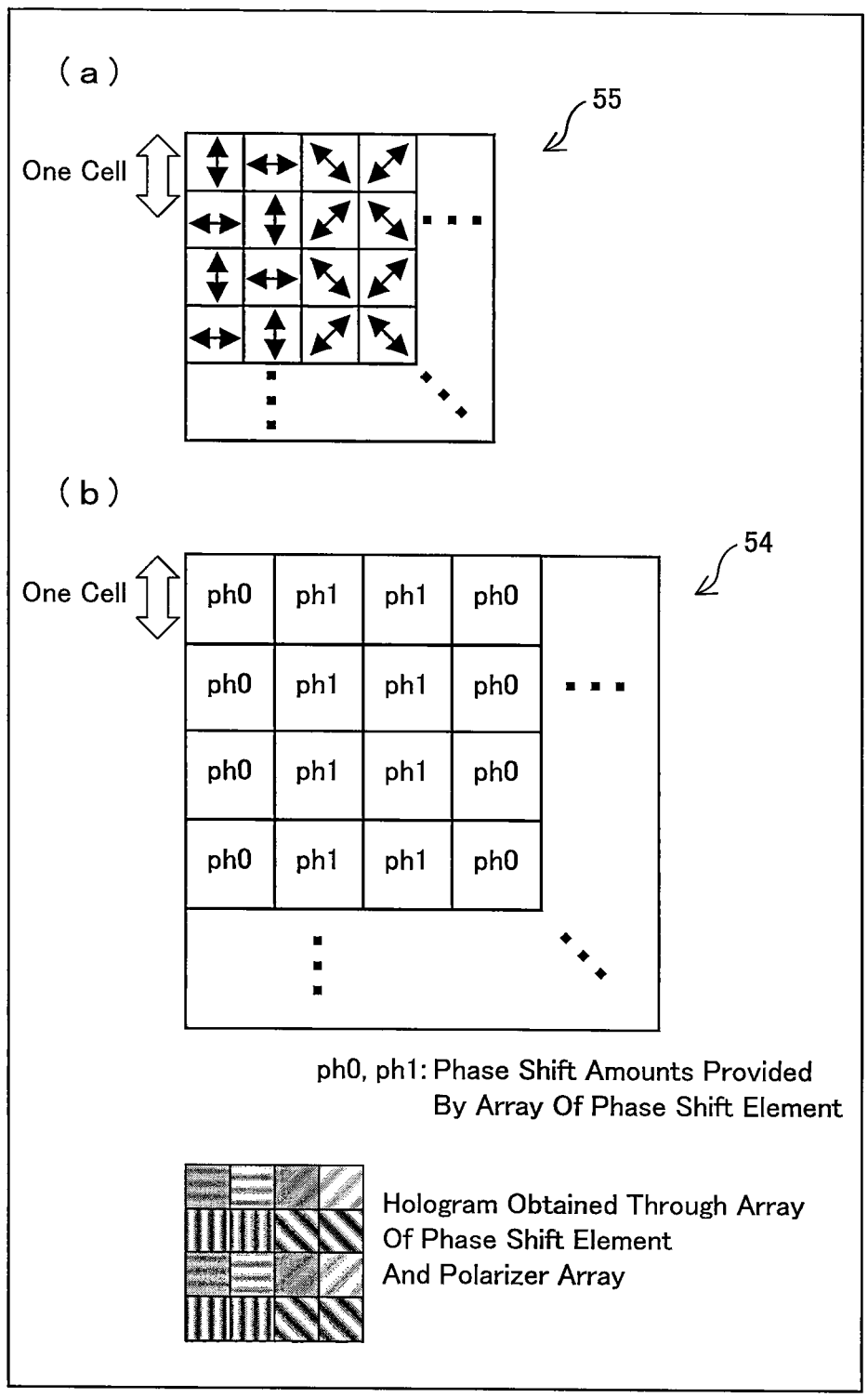

FIG. 43 is a view illustrating a configuration of the polarization imaging apparatus, where (a) is a view illustrating a configuration of a polarizer-array device, and (b) is a view illustrating a configuration of a phase-shift-array device.

Figure 44:
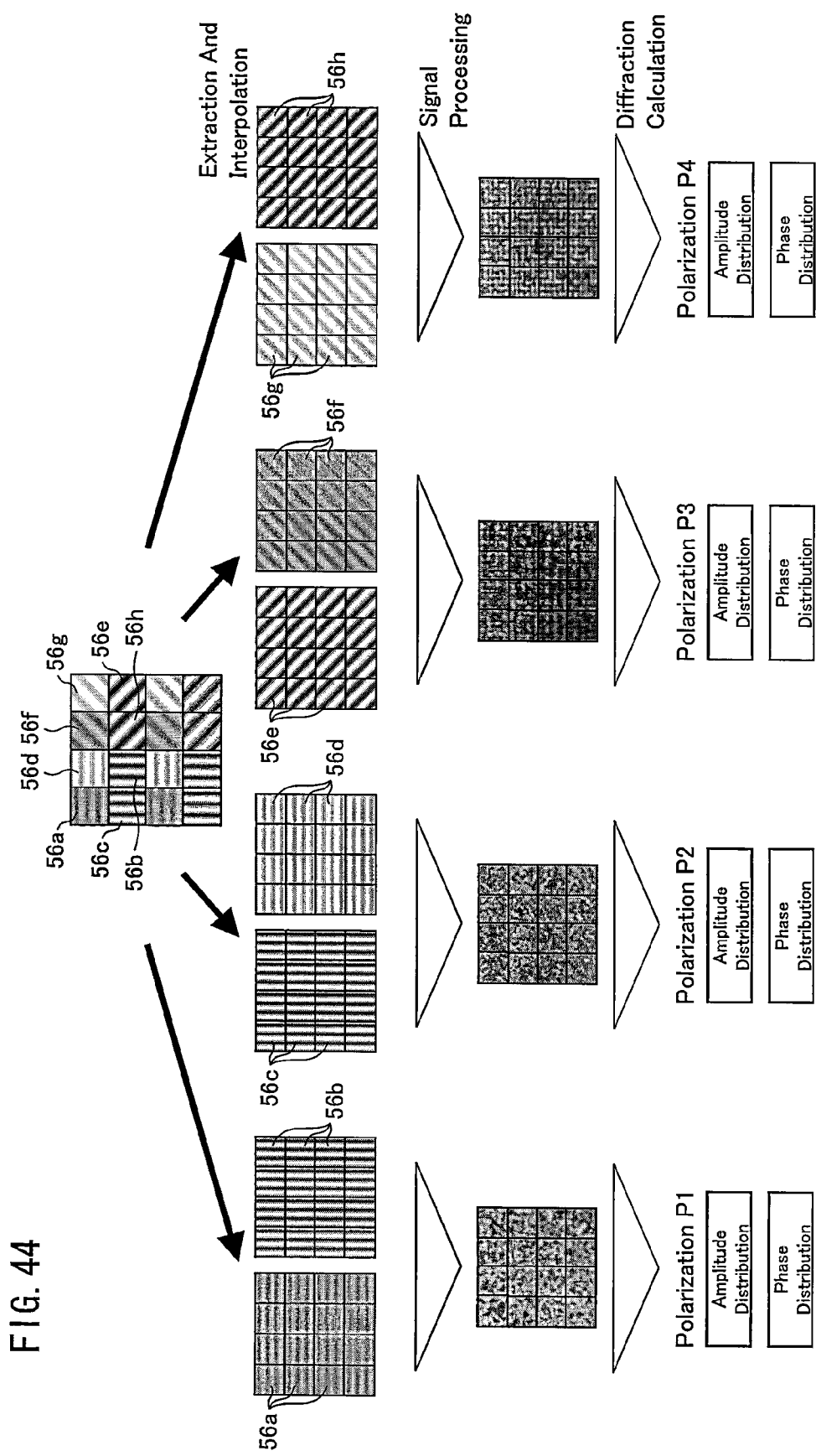

FIG. 44 illustrates an algorithm for the above polarization imaging apparatus generating a reconstructed image of polarized-light components.

Figure 45:
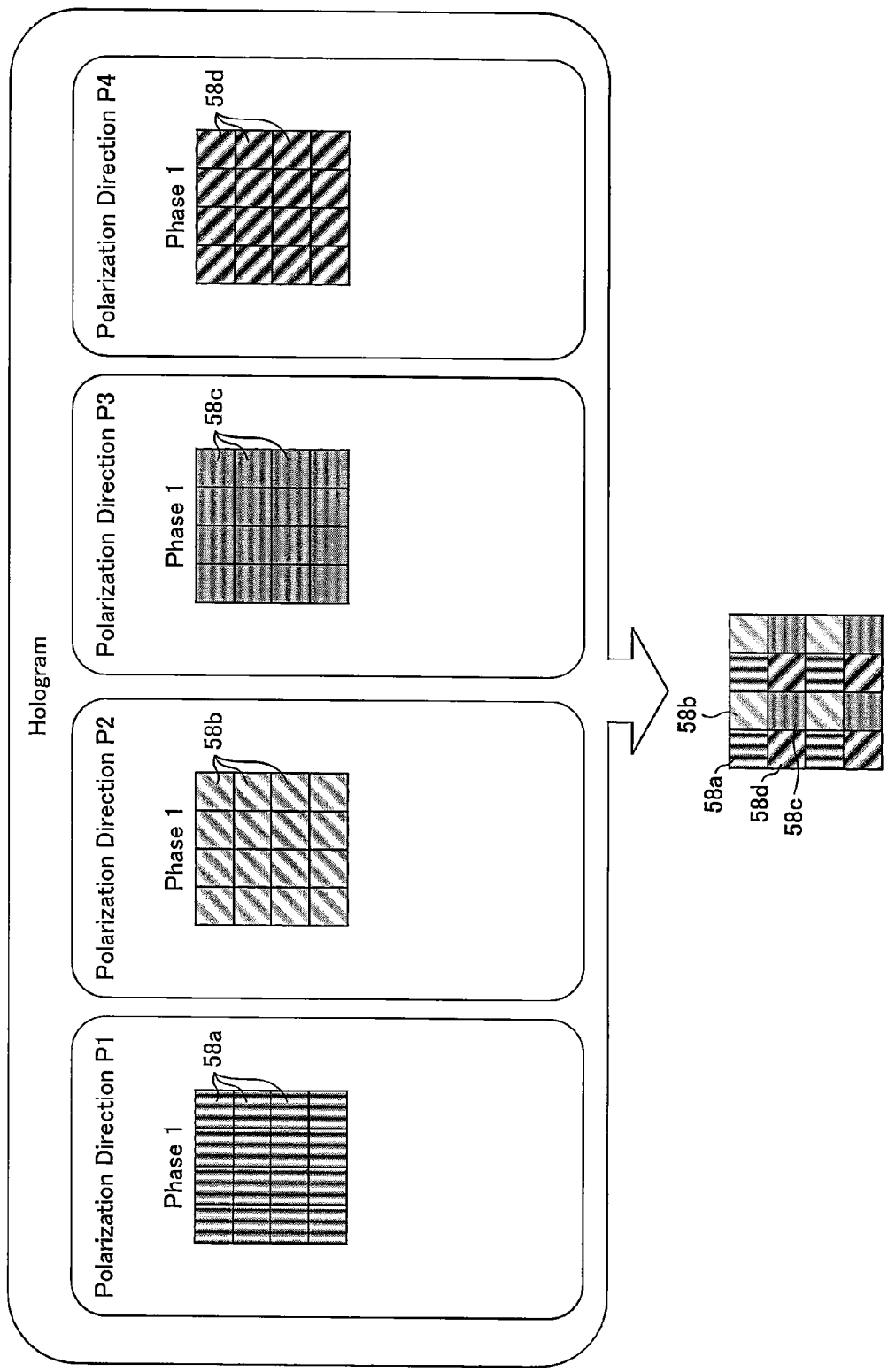

FIG. 45 is a view illustrating a configuration of holograms captured by an image pickup section that is provided in another polarization imaging apparatus according to Embodiment 7.

Figure 46:
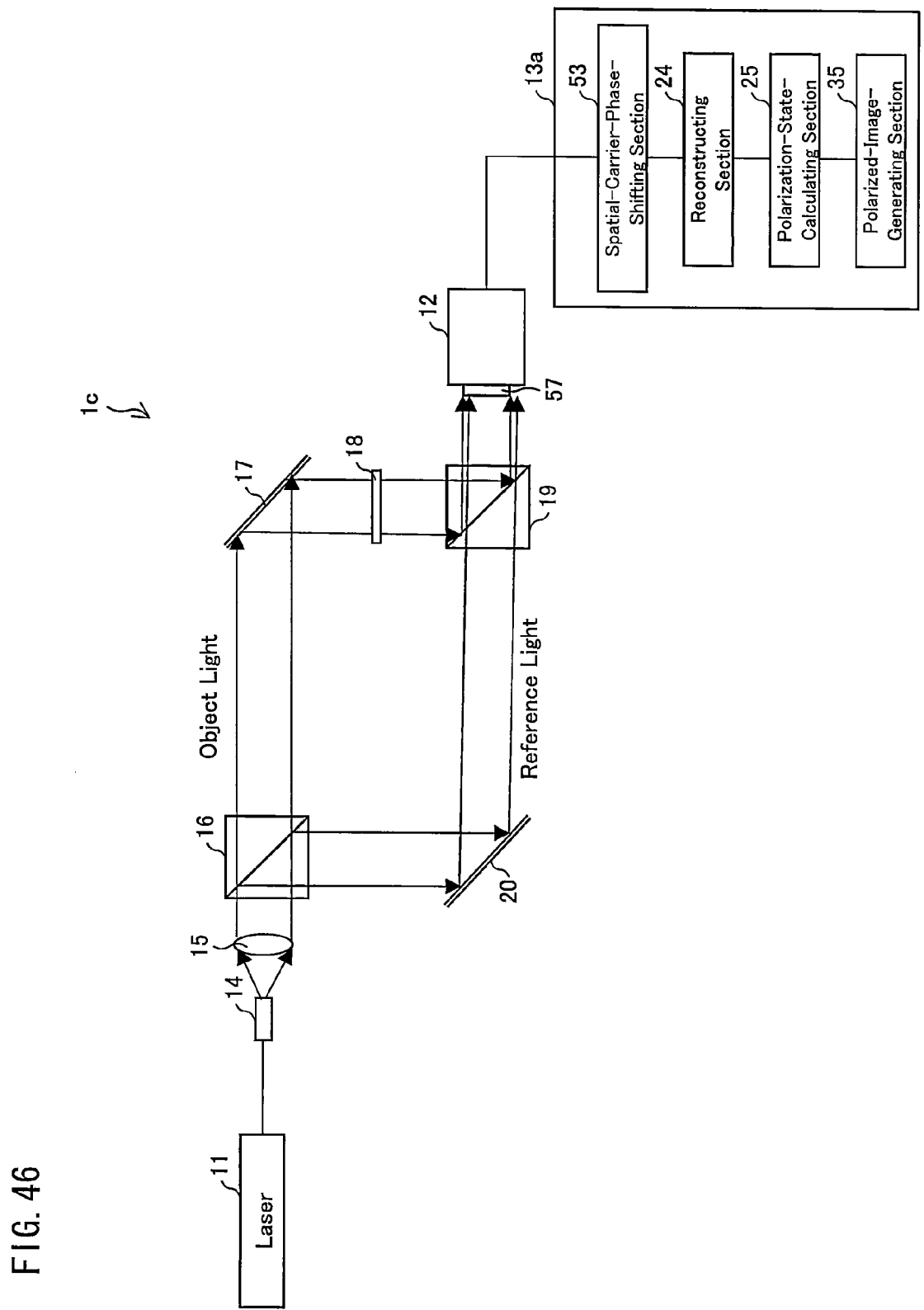

FIG. 46 is a view schematically illustrating another configuration of the above polarization imaging apparatus.

FIG. 47

Figure 47:
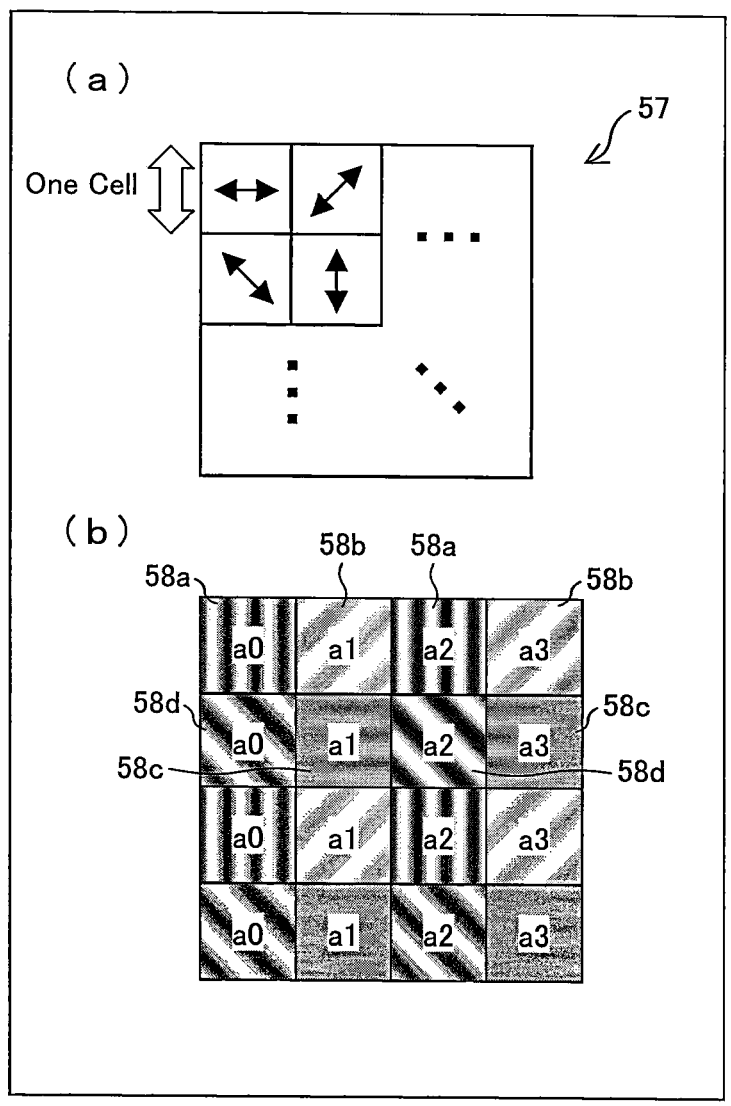

(a) of FIG. 47 is a view illustrating a configuration of a polarizer-array device provided in the above polarization imaging apparatus; and (b) of FIG. 47 is a view illustrating a configuration of a hologram captured by an image pickup section which is provided in the above polarization imaging apparatus.

Figure 48:
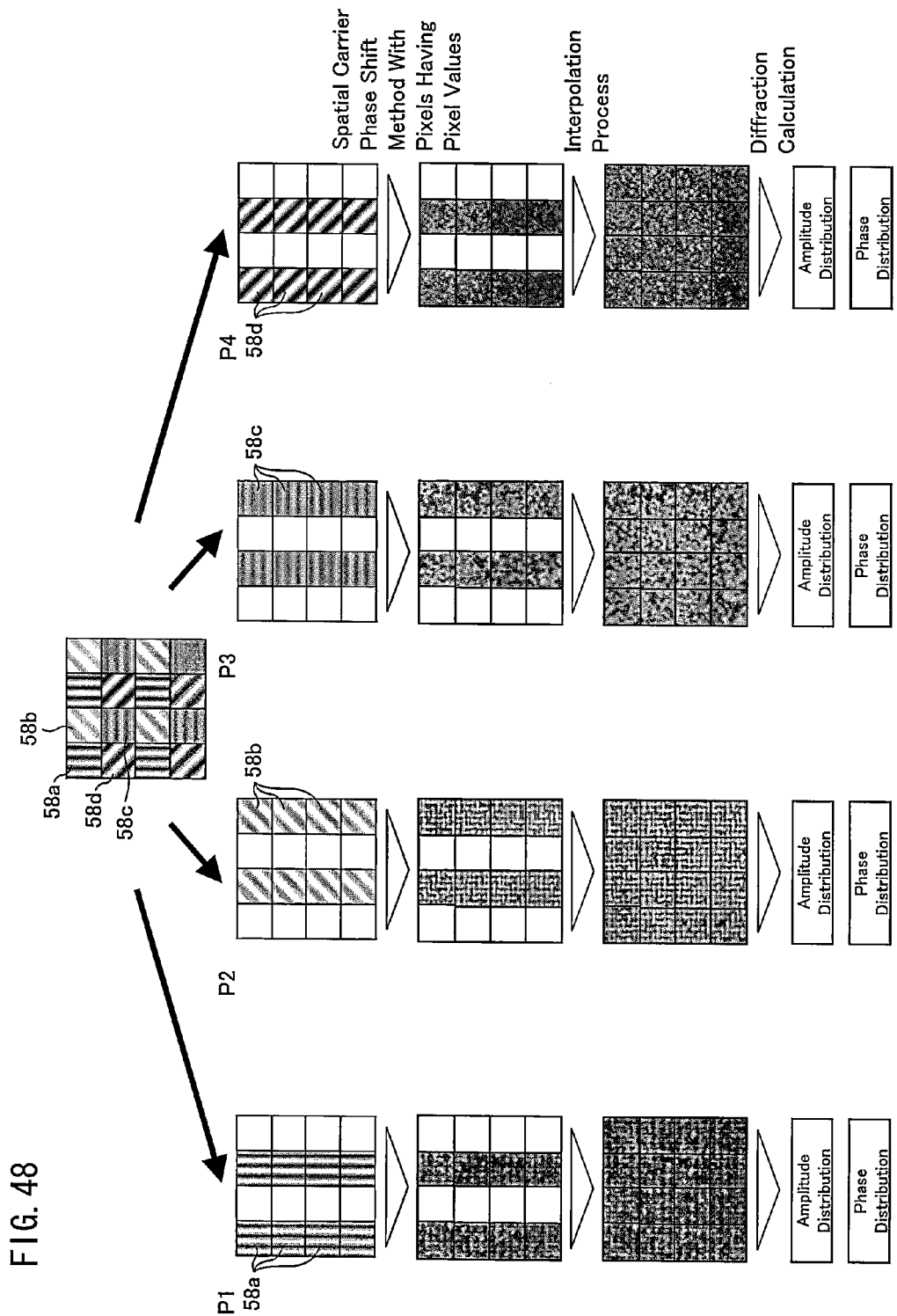

FIG. 48 illustrates an algorithm for the above polarization imaging apparatus generating a reconstructed image of polarized-light components.

Figure 49:
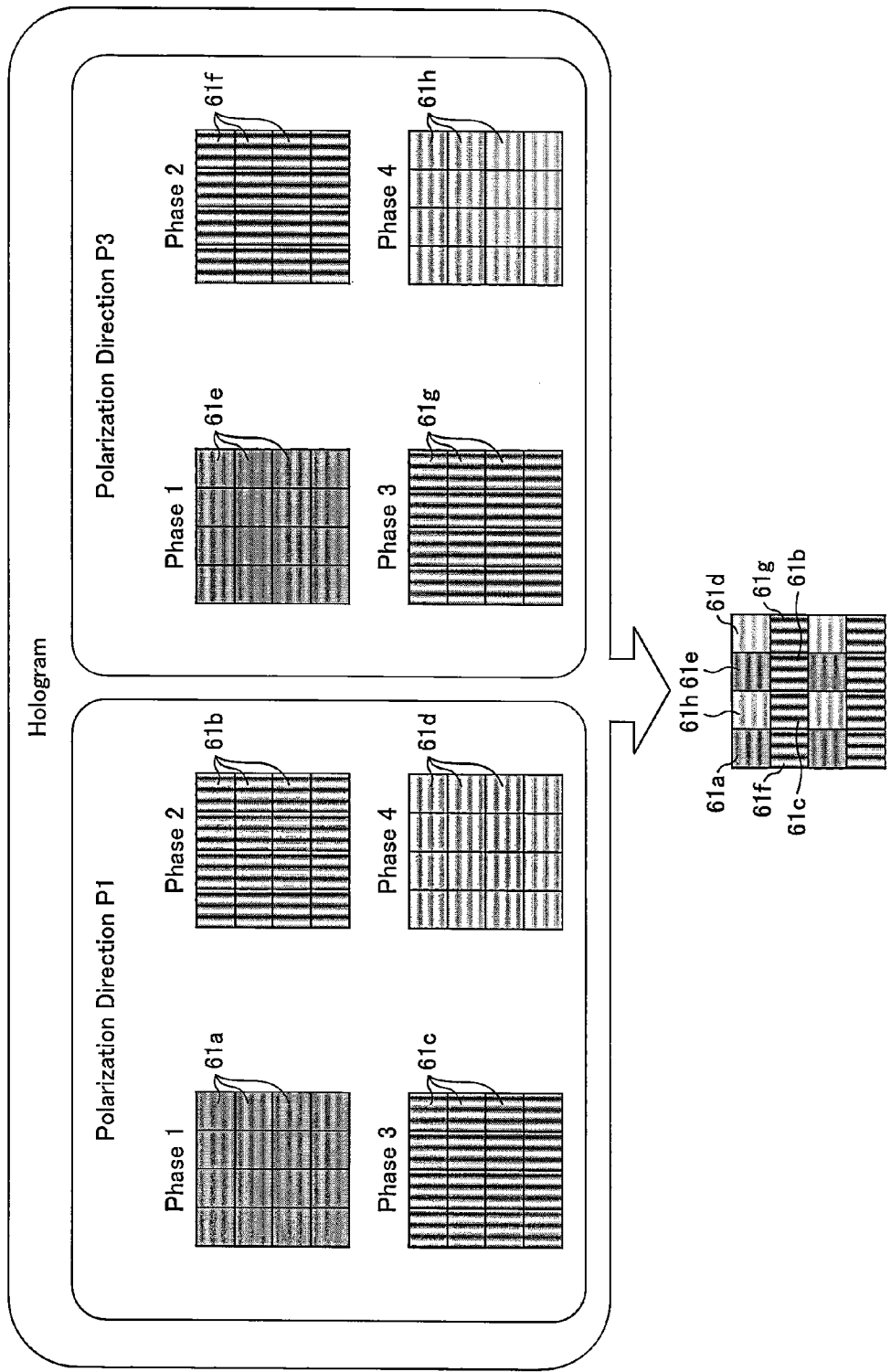

FIG. 49 illustrates a configuration of a hologram captured by an image pickup section which is provided in still another polarization imaging apparatus according to Embodiment 7.

Figure 50:
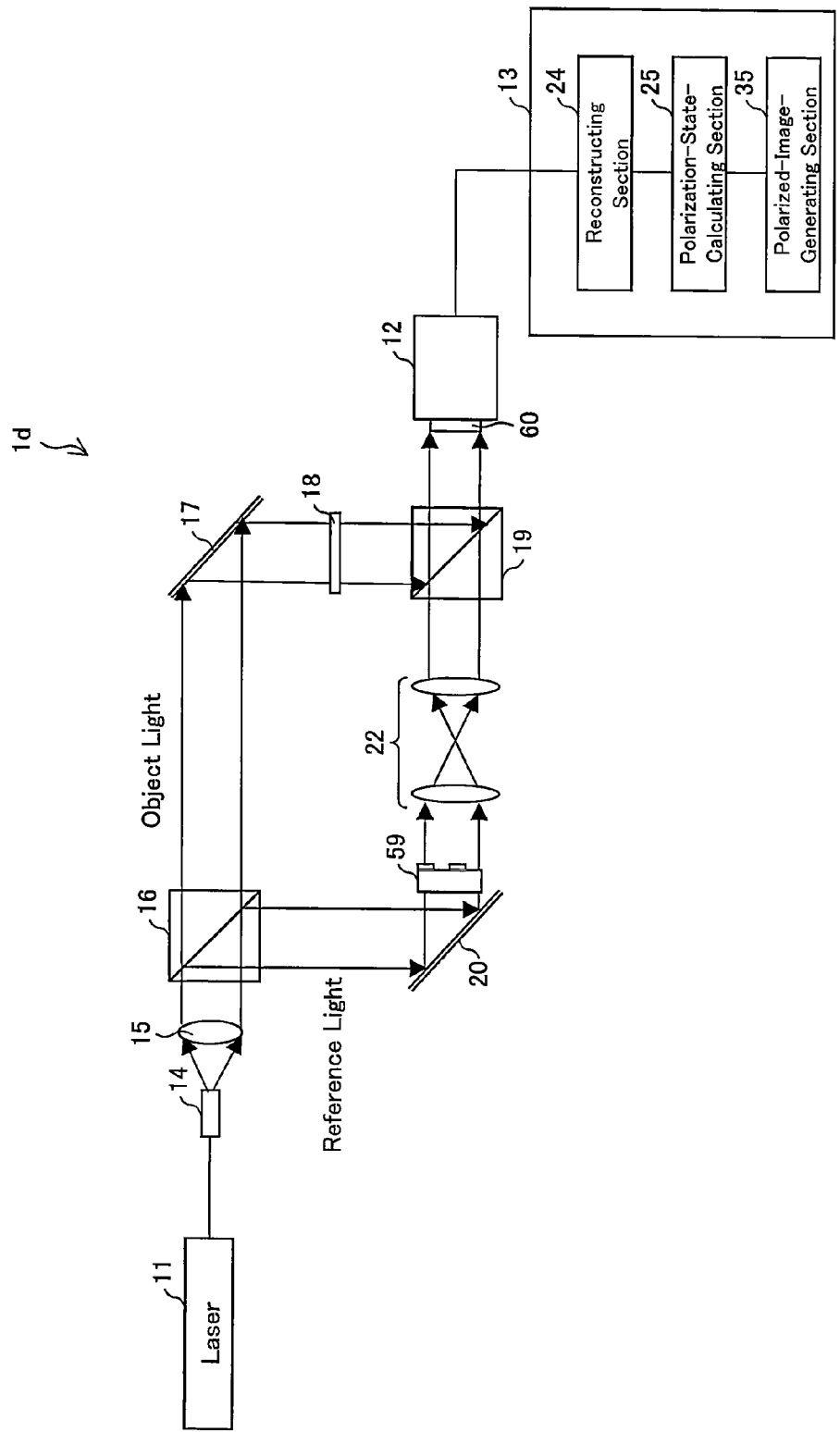

FIG. 50 is a view schematically illustrating still another configuration of the above polarization imaging apparatus.

Figure 51:
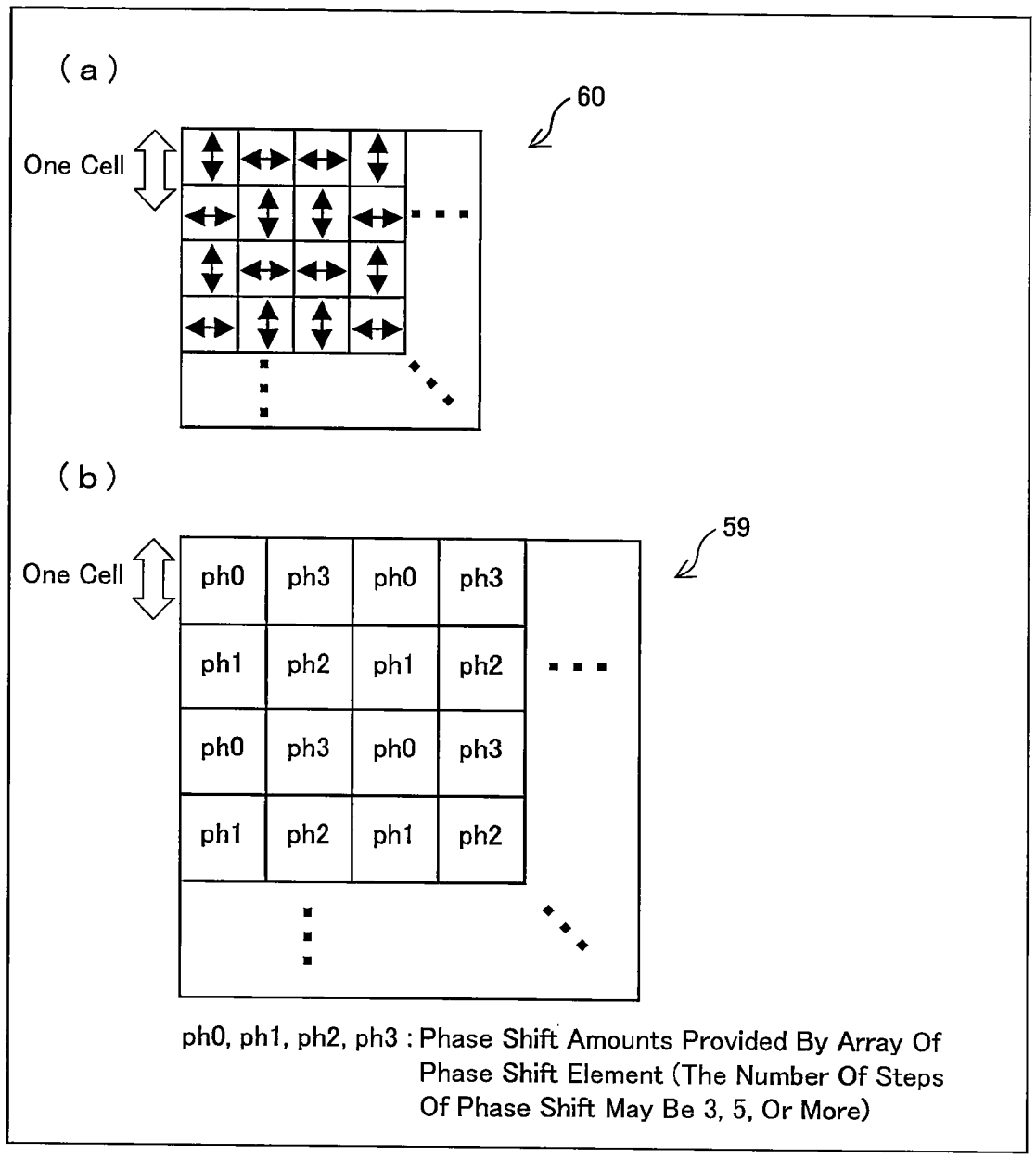

FIG. 51 a view illustrating a configuration of constituent components of the above polarization imaging apparatus, wherein (a) is a view illustrating a configuration of a polarizer-array device, and (b) is a view illustrating a configuration of a phase-shift-array device.

Figure 52:
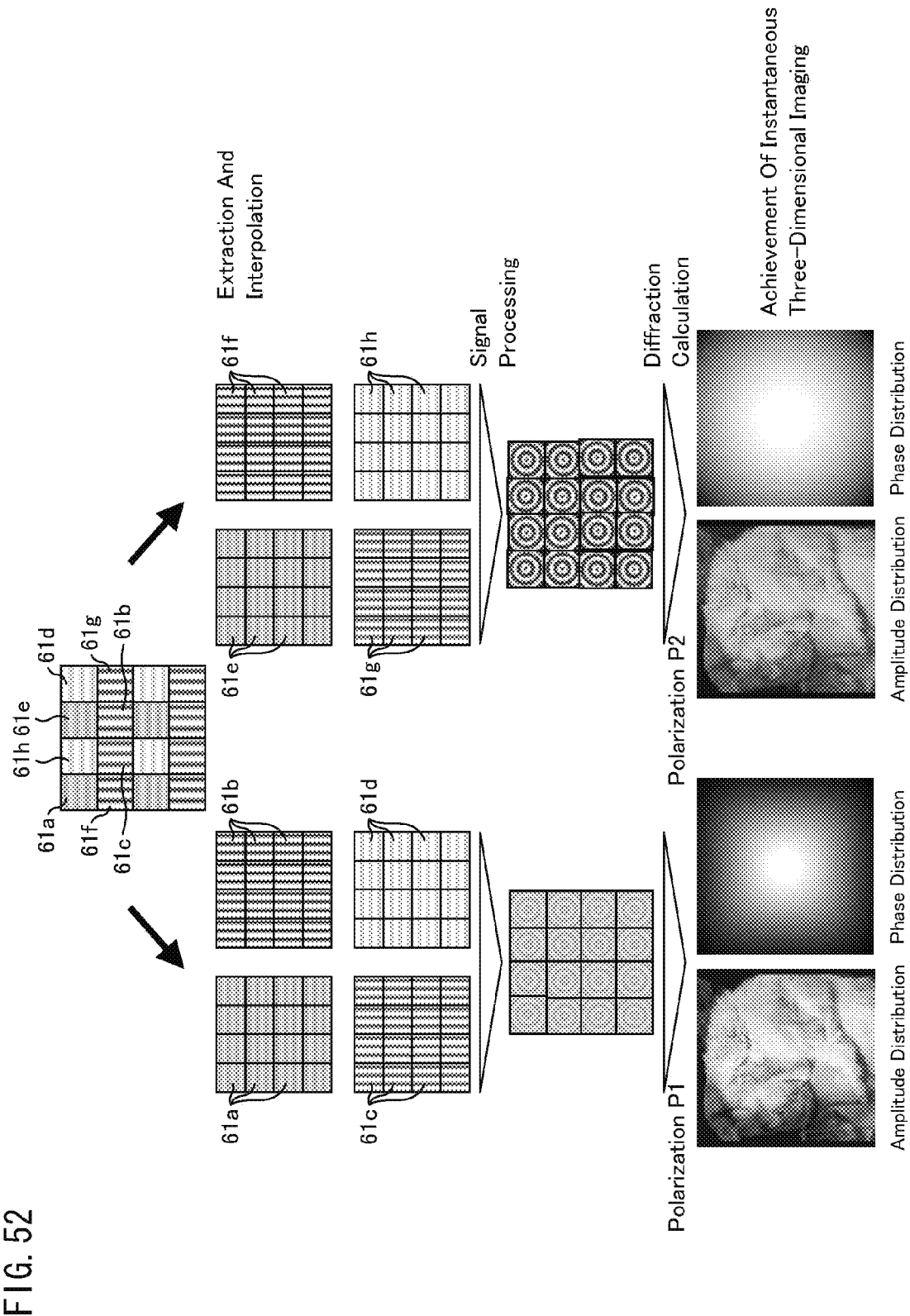

FIG. 52 illustrates an algorithm for the above polarization imaging apparatus generating a reconstructed image of polarized-light components.

Figure 53:
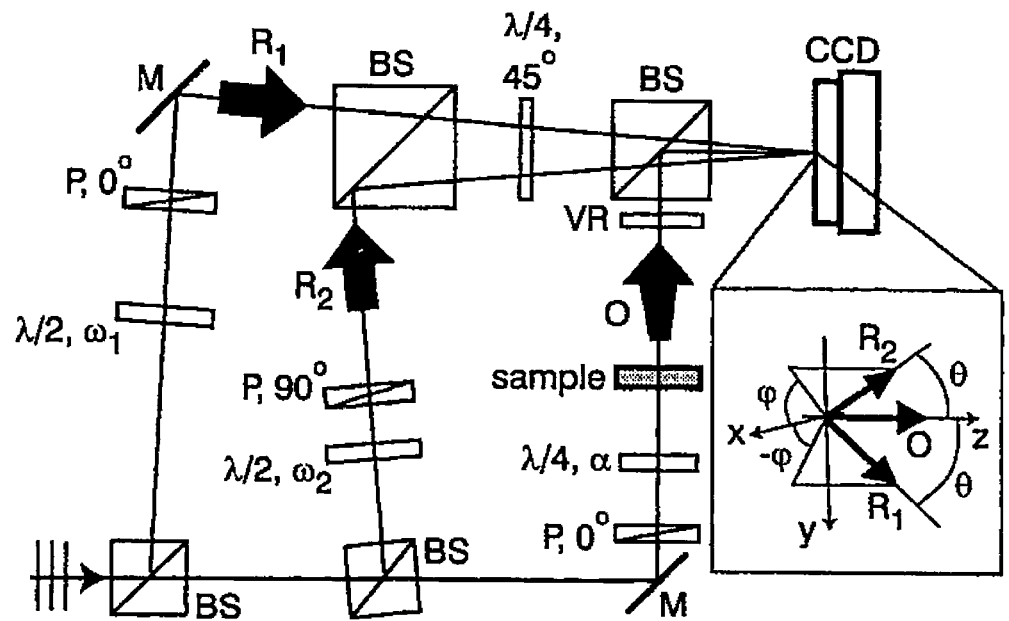

FIG. 53 is a view illustrating a configuration of a conventional polarization imaging apparatus.

Figure 54:
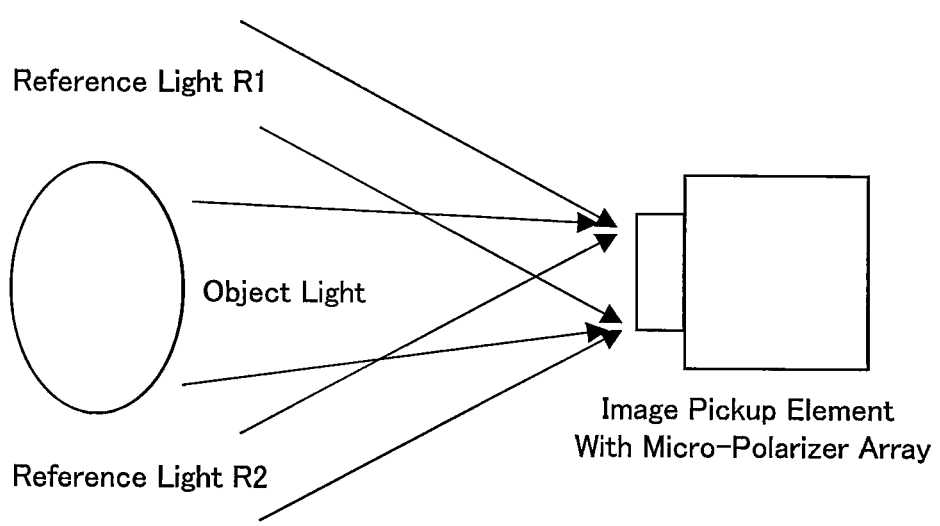

FIG. 54 is a view illustrating a relation between reference light and object light that enter an image pickup device provided in the conventional polarization imaging apparatus.

Figure 55:
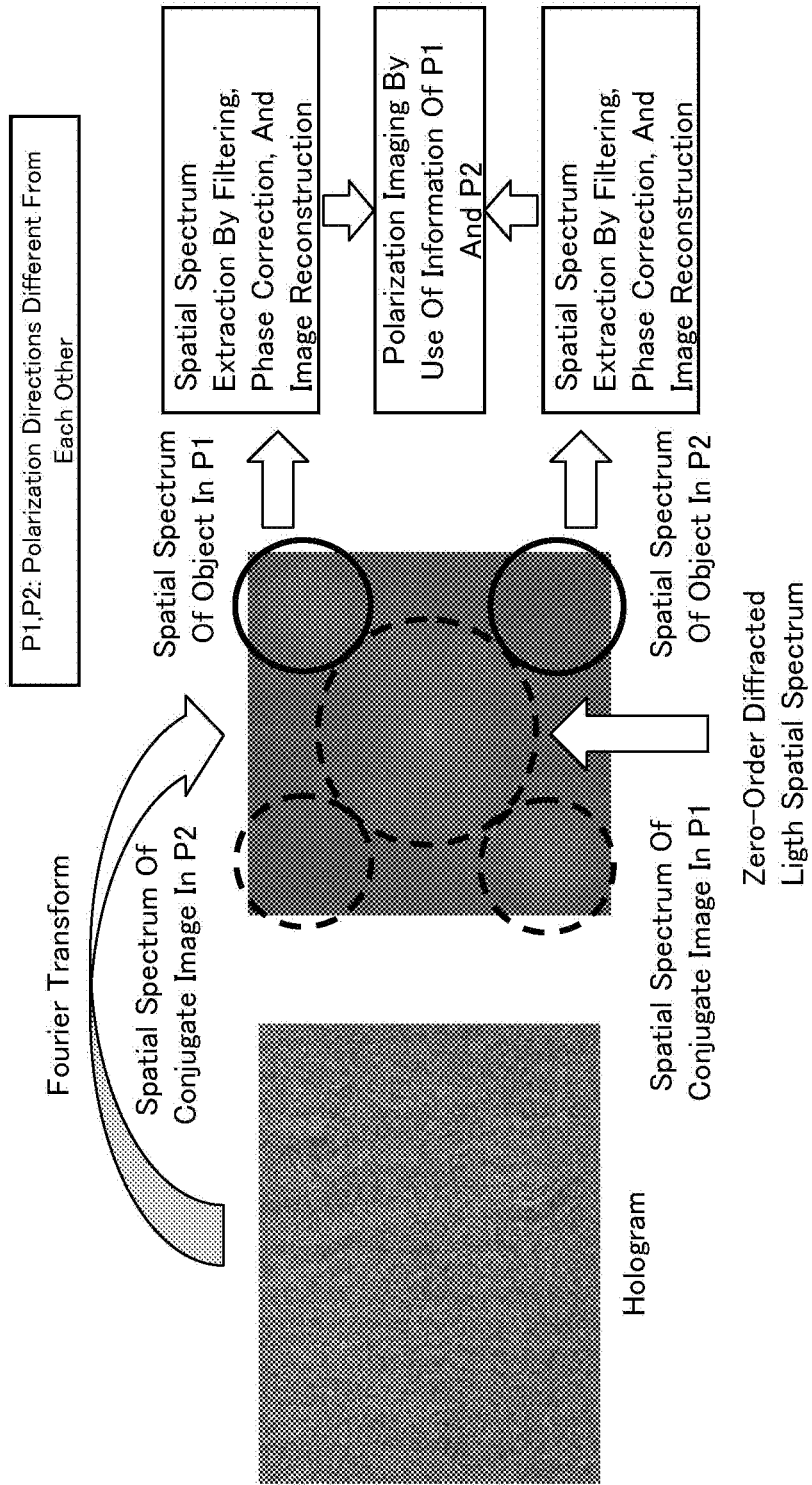

FIG. 55 is a view illustrating a procedure in which an image is reconstructed from a hologram that is recorded by the conventional polarization imaging apparatus.

Figure 56:
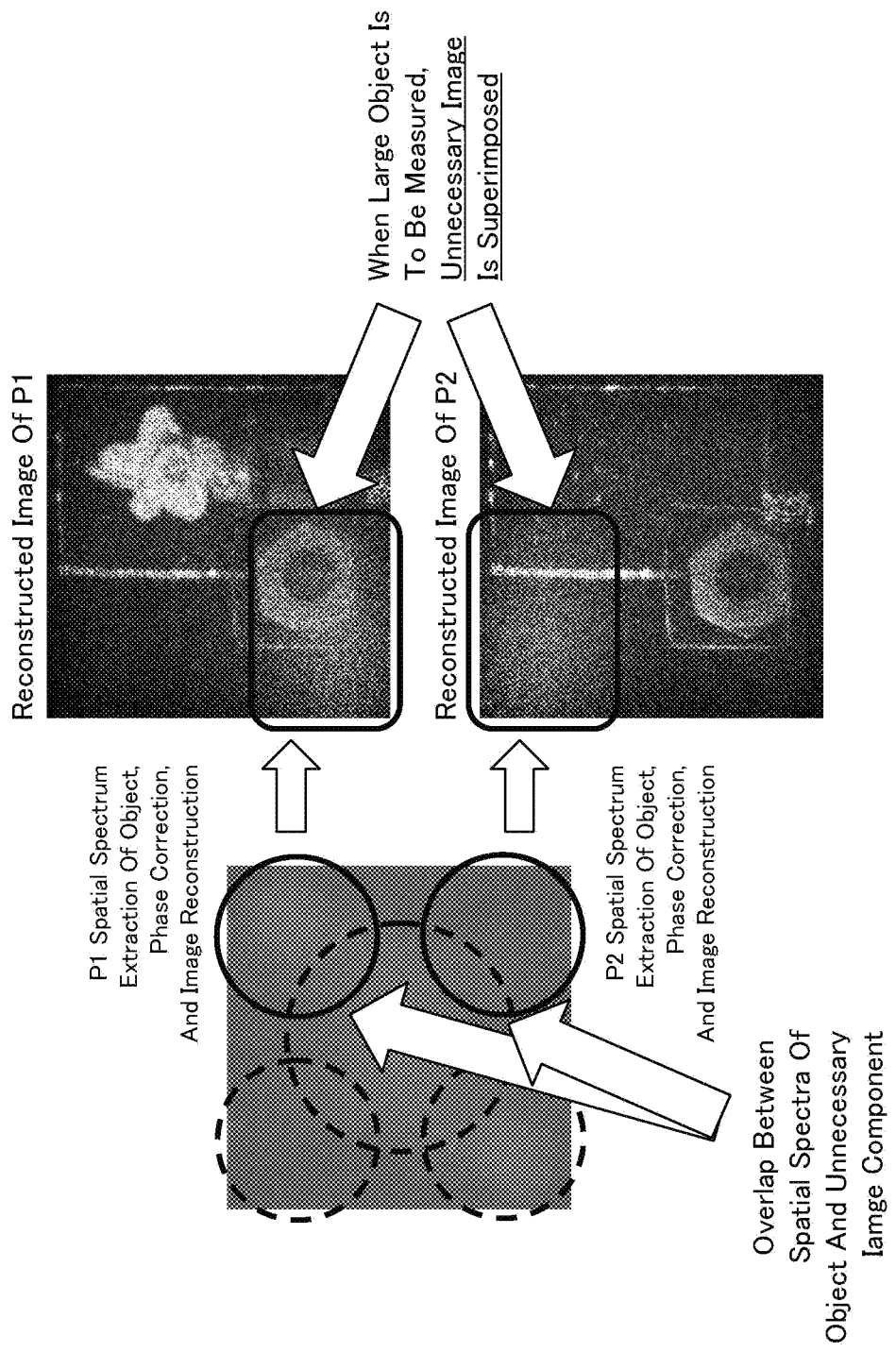

FIG. 56 is a view illustrating a problem of the conventional polarization imaging apparatus.

DESCRIPTION OF EMBODIMENTS

Embodiment 1

The following discusses in detail Embodiment 1, with reference to FIGS. 1 through 8. In Embodiment 1, the number of light sources is 1; in regard to reference light, the number of light components polarized in different directions is 2; and in regard to light components polarized in first and second directions, the number of different phases is 2.

Figure 1:
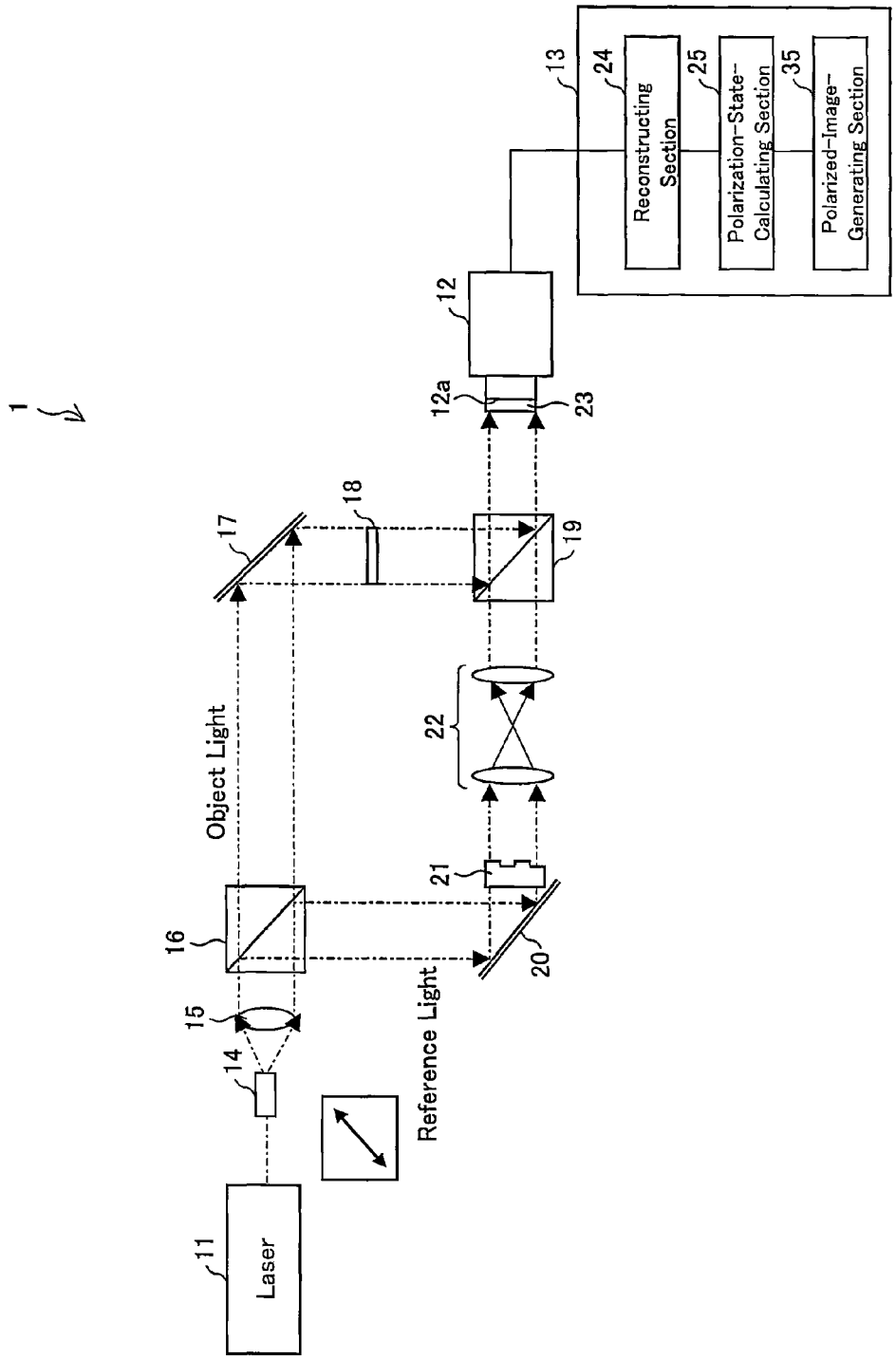
FIG. 1 is a view schematically illustrating a polarization imaging apparatus according to Embodiment 1 of the present invention.

FIG. 1 is a view schematically illustrating a polarization imaging apparatus 1 according to Embodiment 1 of the present invention. The polarization imaging apparatus 1 includes an image pickup device including an optical system provided with a laser light source (light source) 11 and an image pickup element (image pickup section) 12. The image pickup element 12 has an image pickup plane 12a which is made of a CCD. Further, the polarization imaging apparatus 1 includes a computer 13 connected to an output of the image pickup element 12. The image pickup element 12 has a polarizer-array device 23 disposed in front of the image pickup plane 12a.

The laser light source 11 generates coherent light, that is, laser light. Here, a direction that is perpendicular to a laser light propagation direction is defined as a first direction, while a direction that is perpendicular to the laser light propagation direction and also perpendicular to the first direction is defined as a second direction. The laser light is linearly polarized light that includes light components polarized in two directions, that is, a light component polarized in the first direction (first polarized-light component) and a light component polarized in the second direction (second polarized-light component). In Embodiment 1, the first direction is a horizontal direction, while the second direction is a vertical direction. The laser light is linearly polarized in a direction that is inclined at 45° with respect to the first direction and that also is a right-upward direction with respect to the laser light propagation direction. Note that laser light may be turned into circularly-polarized light by a ¼ wave plate. Alternatively, polarization of the laser light may be regulated by providing other polarizer, other wave plate, or the like. The laser light emitted (supplied) from the laser light source 11 becomes collimated light, passing through a beam expander 14 and a collimator lens 15. Then, the laser light is split into reference light and object light by a beam splitter 16. The reference light and the object light each are linearly polarized light including a first polarized-light component and a second polarized-light component.

The object light that is one of thus split light is reflected by a mirror 17 and thrown onto an object 18. The object light having entered the object 18 is diffracted or scattered by the object 18, and thus diffracted or scattered object light exits from the object 18. Subsequently, the object light is reflected by a beam-combining element 19, passes through the polarizer-array device 23, and then enters the image pickup plane 12a of the image pickup element 12 at an angle that is substantially perpendicular to the image pickup plane 12a. The beam-combining element 19 is made of a half mirror.

The reference light that is the other one of thus split light is reflected by a mirror 20, and passes through a phase-shift-array device (phase-shift-array section) 21. (a) of FIG. 2 is a plan view schematically illustrating a part of the phase-shift-array device 21. The phase-shift-array device 21 has plural regions that provide mutually different phases to laser light having passed through the phase-shift-array device 21. The phase-shift-array device 21 is configured by two types of phase-shift regions 21a and 21b. Regardless of a polarization direction of the reference light, a phase of the reference light having passed through the phase-shift region 21b is shifted by $(-\pi/2)$ (delayed by $\pi/2$) relative to a phase of the reference light having passed through the phase-shift region 21a. The phase shifted here is a phase on a plane perpendicular to a reference light propagation direction. For convenience, the reference light having passed through the phase-shift region 21a is referred to as zero-shift reference light (reference light with a phase shift amount of zero), while the reference light having passed through the phase-shift region 21b is referred to as $(-\pi/2)$ shift reference light (reference light with a phase shift amount of $(-\pi/2)$). The phase-shift-array device 21 is configured in an arrangement where (i) a line of the phase-shift regions 21a and (ii) a line of the phase-shift regions 21b are alternately provided. In other words, the phase-shift-array device 21 produces two types of reference light with different phases.

The phase-shift-array device 21 can be made of, for example, glass, and configured by changing thickness of the glass for each phase-shift region. Note that in the phase-shift-array device 21, the regions for providing mutually different phases may be configured by (i) using a wave plates, (ii) changing thickness of each phase-shift region, (iii) providing a liquid crystal element in each region and changing an orientation of liquid crystal molecules; (iv) using other birefringent material, (v) using an element having structural birefringence, or (vi) using a spatial light modulator.

The reference light having passed through the phase-shift-array device 21 passes through an image-forming optical section 22, the beam-combining element 19, and the polarizer-array device (polarizer-array section) 23. Then the reference light enters the image pickup plane 12a of the image pickup element 12 so that an optical axis of the reference light becomes substantially perpendicular to the image pickup plane 12a. The reference light having passed through the phase-shift-array device 21 is diffracted and an image is formed on the image pickup plane 12a by the image-forming optical section 22. In Embodiment 1, the image-forming optical section 22 is made of two lenses. The present invention is not limited to this configuration. The image-forming optical section 22 may be configured by one lens or more than two lenses. Here, for example, after passing through one phase-shift region 21a or one phase-shift region 21b of the phase-shift-array device 21, the reference light focuses on any one line of pixels of the image pickup plane 12a. In other words, an image is formed at one of pixels of the image pickup plane 12a, from the reference light having passed through one cell of the phase-shift regions 21a and the phase-shift regions 21b illustrated as cells of the phase-shift-array device 21 partitioned by a grating in (a) of FIG. 2. Though in (a) of FIG. 2, the phase-shift regions 21a and 21b are illustrated as cells of the phase-shift-array device 21 partitioned by a grating, the phase-shift-array device 21 may have, in practice, a striped structure.

An image pickup optical system of the polarization imaging apparatus 1 is configured by an in-line type optical system. In this optical system, the optical axis of the reference light entering the image pickup plane 12a is perpendicular to the image pickup plane 12a and the object 18 is positioned optically in front (optically in a normal direction) of the image pickup plane 12a.

(b) of FIG. 2 is a plan view schematically illustrating a part of the polarizer-array device 23 in a case where the polarizer-array device 23 is viewed from an image pickup plane 12a side. The polarizer-array device 23 includes polarizers (polarizer regions) 23a and polarizers 23b which are arranged in a checkerboard pattern. The polarizers 23a extract only a light component of transmitted light which light component is polarized in one specified direction (here, horizontal direction) while the polarizers 23b extract only a light component of transmitted light which polarized-light component is polarized in a direction (here, vertical direction) perpendicular to the one specified direction. The reference light and the object light that enter the polarizer-array device 23 each include a horizontally-polarized-light component and a vertically-polarized-light component. In Embodiment 1, the first direction is the horizontal direction, while the second direction is the vertical direction. That is, the polarizers 23a and 23b each transmit only light components of the reference light and the object light corresponding to a polarization direction of each of the polarizers 23a and 23b.

The object light and the reference light having passed through the polarizer-array device 23 enter the image pickup plane 12a at the back of the polarizer-array device 23. The pixels of the image pickup plane 12a each detect light intensity associated with interference between the object light and the reference light. Then, the image pickup element 12 captures an image of an interference pattern (interference figures) that is formed on the image pickup plane 12a from the object light and the reference light. Because the polarizer-array device 23 is bonded next to each other to the image pickup plane 12a, each of the polarizers 23a and 23b corresponds to one pixel of the image pickup plane 12a. Further, an image is formed by the image-forming optical section 22 from the reference light having passed through one cell among the cells of the phase-shift-array device 21 partitioned by the grating as illustrated in (a) of FIG. 2. Then, the reference light passes further through one polarizer 23a or 23b of the polarizer-array device 23. Therefore, the image pickup plane 12a has pixels corresponding to four types of interference in total. The four types of interference includes (i) two types of interference (a) between a horizontally-polarized-light component of the object light and a horizontally-polarized-light component of the reference light with a first phase, and (b) between a horizontally-polarized-light component of the object light and a horizontally-polarized-light component of the reference light with a second phase that is different from the first phase, and (ii) two types of interference (a) between a vertically-polarized-light component of the object light and a vertically-polarized-light component of the reference light with the first phase and (b) between a vertically-polarized-light component of the object light and a vertically-polarized-light component of the reference light with the second phase. More specifically, the image pickup plane 12a includes (i) a pixel where horizontally-polarized light of the zero-shift reference light interferes with horizontally-polarized light of the object light, (ii) a pixel where horizontally-polarized light of the $(-\pi/2)$ shift reference light interferes with horizontally-polarized light of the object light, (iii) a pixel where vertically-polarized light of the zero-shift reference light interferes with vertically-polarized light of the object; and (iv) a pixel where vertically-polarized light of the $(-\pi/2)$ shift reference light interferes with vertically-polarized light of the object. Thereby, the image pickup element 12 can obtain two types of interference patterns of respective phases for each of two polarization directions by one image pickup, that is, simultaneously obtain four types of interference patterns that is formed on the image pickup plane 12a.

The computer 13 includes a reconstructing section 24, a polarization-state-calculating section 25, and a polarized-light-image-generating section 35. The computer 13 obtains image data indicative of the interference pattern whose image is captured by the image pickup element 12, and inputs the image data into the reconstructing section 24.

FIG. 3 is a diagram showing an image reconstruction algorithm in the reconstructing section 24. FIG. 3 shows only a part of an interference pattern (interference figures) 26.

The interference pattern 26 formed on the image pickup plane 12a includes four types of pixels including (i) a pixel 27a where a horizontally-polarized-light component of the object light interferes with a horizontally-polarized-light component of the zero-shift reference light, (ii) a pixel 27b where a horizontally-polarized-light component of the object light interferes with a horizontally-polarized-light component of the $(-\pi/2)$ shift reference light, (iii) a pixel 27c where a vertically-polarized-light component of the object light interferes with a vertically-polarized-light component of the zero-shift reference light, and (iv) a pixel 27d where a vertically-polarized-light component of the object light interferes with a vertically-polarized-light component of the $(-\pi/2)$ shift reference light.

The reconstructing section 24 extracts the four types of pixels 27a to 27d so as to obtain (i) an interference pattern 28a of the interference between the horizontally-polarized light components of the object light and the zero-shift reference light, (ii) an interference pattern 28b of the interference between the horizontally-polarized light components of the object light and the $(-\pi/2)$ shift reference light, (iii) an interference pattern 28c of the interference between the vertically-polarized-light component of the object light and the zero-shift reference light, and (iv) an interference pattern 28d of the interference between the vertically-polarized light component of the object light and the $(-\pi/2)$ shift reference light. The reconstructing section 24 obtains respective complex amplitude distributions of the horizontally-polarized-light component and the vertically-polarized light component of the object light, from the four interference patterns 28a to 28d which are obtained by dividing the pixels of the interference pattern 26.

Next, the reconstructing section 24 interpolates pixel values of missing pixels (pixels shown in white in the interference patterns 28a, 28b, 28c, and 28d) in (i) the interference pattern 28a corresponding to horizontally-polarized light in the case of the zero-shift reference light, (ii) the interference pattern 28b corresponding to horizontally-polarized light in the case of the $(-\pi/2)$ shift reference light, (iii) the interference pattern 28c corresponding to vertically-polarized light in the case of the zero-shift reference light, and (iv) the interference pattern 28d of vertically-polarized light in the case of the $(-\pi/2)$ shift reference light. Thereby, the reconstructing section 24 obtains (i) an interpolated interference pattern 29a of the horizontally-polarized light in the case of the zero-shift reference light, (ii) an interpolated interference pattern 29b of the horizontally-polarized light in the case of the $(-\pi/2)$ shift reference light, (iii) an interpolated interference pattern 29c of the vertically-polarized light in the case of the zero-shift reference light, and (iv) an interpolated interference pattern 29d of the vertically-polarized light in the case of the $(-\pi/2)$ shift reference light.

It requires information on an intensity distribution of the reference light on the image pickup plane 12a, to obtain complex amplitude distributions of the object light from these interference patterns. Because the intensity distribution of the reference light is constant and does not change, an image of only the reference light can be captured by blocking the object light or the like in advance or after an image of the interference patterns of the object is captured. In obtaining the intensity distribution of the reference light, the object 18 is not necessary. The reconstructing section 24 obtains an intensity distribution 30 of reference light from the image pickup element 12 in the same manner as the interference pattern 26. Because the reference light has passed through the polarizer-array device 23, the intensity distribution 30 of the reference light includes both of pixels 31a each indicating an intensity of a horizontally-polarized-light component of the reference light and pixels 31b each indicating an intensity of a vertically-polarized-light component of the reference light.

The reconstructing section 24 extracts each of these two types of pixels 31a and 31b so as to obtain an intensity distribution 32a of the horizontally-polarized-light component of the reference light and an intensity distribution 32b of the vertically-polarized-light component of the reference light.

Further, in a case where an intensity distribution of reference light can be assumed or predicted to be uniform, it may be omitted to record the intensity distribution of the reference light and to use an intensity distribution of reference light which is produced by the reconstructing section 24 at the time when signal processing is performed for obtaining a complex amplitude distribution of the object light. By repeatedly processing the interference patterns previously obtained, an appropriate intensity distribution of the reference light can be estimated.

Then, the reconstructing section 24 interpolates pixel values of missing pixels (pixels shown in white in the intensity distributions 32a and 32b) in (i) the intensity distribution 32a of the horizontally-polarized-light component of the reference light and (ii) the intensity distribution 32b of the vertically-polarized-light component of the reference light. Thereby, the reconstructing section 24 obtains (i) an interpolated intensity distribution 33a of the horizontally-polarized-light component of the reference light and (ii) an interpolated intensity distribution 33b of the vertically-polarized-light component of the reference light.

The reconstructing section 24 can obtain a complex amplitude distribution 34a of the horizontally-polarized-light component of the object light on the image pickup plane 12a by a two-step phase-shifting method (See Non-Patent Literature 3), from (i) the interpolated interference patterns 29a and 29b respectively for different shift amounts and (ii) the interpolated intensity distribution 33a of the reference light which (i) and (ii) are concerned with the horizontally-polarized-light components. Similarly, the reconstructing section 24 can obtain a complex amplitude distribution 34b of the vertically-polarized-light component of the object light on the image pickup plane 12a, from (i) the interpolated interference patterns 29c and 29d respectively for the different shift amounts and (ii) the interpolated intensity distribution 33b of the reference light which (i) and (ii) are concerned with the vertically-polarized-light components.

The reconstructing section 24 can obtain a focused image (a reconstructed image indicative of an amplitude distribution) for each polarized-light component at a given depth position, by diffraction integral on thus obtained complex amplitude distribution. Further, the reconstructing section 24 also can obtain a phase distribution including information on a three-dimensional shape of the object, in regard to the focused image. The reconstructing section 24 outputs, to the polarization-state-calculating section 25, the reconstructed image and the phase distribution thus obtained by calculation for each of the horizontally-polarized-light component and the vertically-polarized-light component at the given position of the object in the depth direction.

The polarization-state-calculating section 25 obtains Stokes parameters from (i) the reconstructed image and the phase distribution of the horizontally-polarized-light component and (ii) the reconstructed image and the phase distribution of the vertically-polarized-light component, for representation of a detailed polarization state at each position (each pixel) of the reconstructed image. First, the polarization-state-calculating section 25 obtains a difference between (i) the phase distribution of the horizontally-polarized-light component and the phase distribution of the vertically-polarized-light component. Then, the polarization-state-calculating section 25 obtains Stokes parameters S0, S1, S2, and S3 at each position (each pixel) of the reconstructed image, from thus obtained phase difference distribution and the amplitude distribution of each of the polarized-light components. These Stokes parameters can be expressed in the following formulae:

$$S0 = A_x^2 + A_y^2$$

$$S1 = A_x^2 - A_y^2$$

$$S2 = 2A_x A_y \cos(\theta_x - \theta_y)$$

$$S3 = 2A_x A_y \sin(\theta_x - \theta_y)$$

where: $A_x$ is an amplitude distribution of the object in regard to horizontally-polarized light; $A_y$ is an amplitude distribution of the object in regard to vertically-polarized light; $\theta_x$ is a phase distribution of the object in regard to the horizontally-polarized light; and $\theta_y$ is a phase distribution of the object in regard to the vertically-polarized light. The polarization-state-calculating section 25 outputs thus obtained Stokes parameters to the polarized-light-image-generating section 35. Note that the polarization-state-calculating section 25 may obtain the detailed polarization state by obtaining Jones vectors, Mueller matrices or the like instead of the Stokes parameters. The polarization-state-calculating section 25 may also represent the polarization state by obtaining other parameters that represents the polarization state. The polarization-state-calculating section 25 can obtain a detailed polarization state of an image of the object, from the complex amplitude distributions of the object light in regard to the horizontally-polarized light component and the vertically-polarized light component.

The polarized-light-image-generating section 35 obtains, from the Stokes parameters, an amplitude distribution of the object in each polarization direction (e.g., each of a 0-degree direction (horizontal direction), a 45-degree direction, a 90-degree direction (vertical direction), and a 135-degree direction). Then, the polarized-light-image-generating section 35 colors the amplitude distribution separately for each polarization direction and generates an object image indicative of a polarized-light distribution.

As described above, in Embodiment 1, an image of the four types of interference patterns is simultaneously obtained by one image pickup. The four types of interference patterns correspond to respective varying combinations of phases and polarization directions of the reference light. From the four types of interference patterns, polarization imaging is achieved by obtaining the Stokes parameters each indicative of a detailed polarization state of the constructed image. According to Embodiment 1, each interference pattern is obtained at a time by (i) simultaneously forming, on one plane (image pickup plane 12a), the four types of interference patterns which correspond to respective varying combinations of phases and polarization directions of the reference light and (ii) then dividing pixels of the image pickup plane. Accordingly, by one image pickup, it is possible to obtain necessary information for imaging a three-dimensional structure of the object and a polarized-light distribution of the object. This makes it possible to realize imaging of (i) an instantaneous three-dimensional structure of a changing-changing object and (ii) an instantaneous polarized-light distribution of the dynamically-changing object. Further, in Embodiment 1, because respective interference patterns for different phases of the reference light are obtained, it becomes possible to obtain a reconstructed image (first-order diffracted light) from which zero-order diffracted light and a conjugate image (minus first-order diffracted light) are removed by a phase shift method. Therefore, a reconstructed image can be obtained by in-line type digital holography. Accordingly, as compared to a technique of Non-Patent Literature 1, a photographable area is wider and it is possible to obtain a more detailed structure of an object. Consequently, in Embodiment 1, it is possible to observe in detail a larger dynamically-changing object. Further, in Embodiment 1, it is possible to make an optical system simpler and therefore, make the polarization imaging apparatus 1 smaller, as compared to those of a configuration of Non-Patent Literature 1 that employs off-axis type digital holography. This is because, in Embodiment 1, the number of polarization-regulating elements (wave plates, polarizers, and the like) can be reduced.

For obtaining the information on the three-dimensional structure and the information on the polarized-light distributions simultaneously, it is natural to think of employing one polarization imaging camera and one image pickup element for holography and capturing images separately by the polarization imaging camera and the image pickup element. However, when image capturing is performed separately by use of two image pickup elements (cameras), it is required to control precisely by nanometer order relative positions of the two image pickup elements by precise alignment. This is not practical. In order to solve this problem, the inventors of the present application attained the invention of a method (present invention) in which four types of pixels are alternately arranged in one image pickup plane so as to correspond to respective varying combinations of (i) at least two types of pixels (pixels for different polarizations) each for obtaining a polarized-light distribution and (ii) at least two types of pixels (pixels for different phases of reference light) for obtaining three-dimensional information (for obtaining an object image by the phase shift method). In this method, different types of interference patterns are subjected to space-division multiplexing and formed on an image pickup plane. The number of divisions (pixels) in the space-division multiplexing is at least four (the number of apparent pixels is ¼ or less of the total number of the pixels). Therefore, in comparison with an off-axis type polarization imaging apparatus (Non-Patent Literature 1, etc.), image quality seemingly deteriorates in Embodiment 1. Accordingly, Embodiment 1 is predicted to have no superiority. However, as a result of analysis and evaluation performed by the inventors of the subject application, it was found that (i) the present invention has a wider view and a higher resolution as compared to those of the configuration of Non-Patent Literature 1 and (ii) therefore, the present invention is remarkably superior to conventional techniques. In a simulation result described later, it is explained that in Embodiment 1, it is possible to obtain (i) a reconstructed image that is not inferior and (ii) polarized-light distributions, regardless of the apparent number of pixels that is ¼ of the total number of the pixels.

Note that polarization directions of laser light employed is not necessarily be equivalent to the first and second directions, as long as the laser light includes both light components respectively polarized in the first and second directions. The laser light may also be circularly-polarized light or elliptically-polarized light. Certainly, the first and second directions are not limited to the horizontal and vertical directions.

Further, it is not necessary to form, at one pixel of the image pickup element, an image of reference light that has passed through one cell (phase-shift region) of the phase-shift-array device partitioned by a grating. For example, it is possible to configure an image-forming optical system so that an image of reference light having passed through one cell of the phase-shift-array device is formed at plural pixels (e.g., 2×2 pixels) of the image pickup element. Similarly, one cell (a polarizer 23a or 23b) of the polarizer-array device does not necessarily correspond to one pixel of the image pickup element. One cell of the polarizer-array device may be configured to correspond to plural pixels (e.g., 2×2 pixels). Moreover, in Embodiment 1, the reference light having passed through the phase-shift-array device is split into reference light beams of two types of phases. However, the reference light may be split into reference light beams of three types of phases. In addition, there may be three or more directions of optical axes of polarizers in the polarizer-array device. In other words, it is possible to simultaneously capture an image of four or more types of interference patterns respectively corresponding to varying combinations of phases of reference light and polarization directions, and thereby to obtain reconstructed images and Stokes parameters from thus obtained interference patterns.

Further, Embodiment 1 employs a transmissive optical system for observation of object light that has passed through an object and diffracted by the object. However, the present invention may be accomplished by employing a reflective optical system for observation of object light that is reflected and scattered by an object. Furthermore, in Embodiment 1, an image of an interference pattern for each polarization direction is captured by use of a polarizer-array device. However, the present invention is not limited to this. It is possible to employ an image pickup element that (i) splits object light and reference light that are received by the image pickup element, into plural light beams by a beam splitter, (ii) causes each split light beam to pass through a polarizer of a different direction, (iii) captures an image of each split light beam on a separate image pickup plane, and (iv) captures an interference pattern in each polarization direction.

<Simulation Result>

The inventors of the present invention performed, on a computer, simulation in which reconstructed images are generated and Stokes parameters are calculated according to Embodiment 1. The following explains a result of this simulation.

An optical system for capturing an image of an object is the polarization imaging apparatus 1 shown in FIG. 1. (a) of FIG. 4 shows an image of an amplitude distribution of a light component polarized in a horizontal direction (P1) which amplitude distribution indicates apparent lightness of an object. (b) of FIG. 4 shows an image of an amplitude distribution of a light component polarized in a vertical direction (P2) which amplitude distribution indicates apparent lightness of the object. The object has a square cross section along a plane perpendicular to a direction in which the object light passes through the object. On the object, an image of a cat is formed. (c) of FIG. 4 corresponds to (a) of FIG. 4 and shows an image of a phase distribution in a case where laser light polarized in the horizontal direction (P1) passes through the object. (d) of FIG. 4 corresponds to (b) of FIG. 4 and shows an image of a phase distribution in a case where laser light polarized in the vertical direction (P2) passes through the object. In (c) and (d) of FIG. 4, a phase delay is expressed in the lightness. A phase of laser light (object light) in the darkest region is delayed by $1.5\pi$ relative to a phase of laser light in the brightest region. (a) of FIG. 5 shows an image illustrating a Stokes parameter S0 of object light that has been diffracted by the object. Similarly, (b) of FIG. 5 shows an image illustrating a Stokes parameter S1 of such object light; (c) of FIG. 5 shows an image illustrating a Stokes parameter S2 of such object light; and (d) of FIG. 5 shows an image illustrating a Stokes parameter S3 of such object light. In (a) to (d) of FIG. 5, a brighter region has a larger Stokes parameter.

Note that conditions for the simulation were assumed as below: (i) a wavelength $\lambda$ of laser light employed was 532 nm; (ii) a cross section size of the object (a size in terms of length and width of an image shown in (a) of FIG. 4) was 3.69 mm×3.69 mm; (iii) a distance between the object and the image pickup plane of the image pickup element (a distance along an optical axis of the object light) was 50 mm; (iv) a size of each pixel of the image pickup element was 1.8 μm×1.8 μm; (v) the number of pixels of the image pickup element was 2048×2048 pixels; and (vi) a pixel pitch was 1.8 μm. Under the above conditions, the simulation was performed on a computer. The simulation included the steps of (i) obtaining interference patterns formed on the image pickup plane from the object light of the object and the reference light; (ii) calculating reconstructed images; and (iii) obtaining Stokes parameters of the reconstructed images from the reconstructed images. Note that the step (i) was also performed by simulation on a computer.

(a) to (d) of FIG. 6 show images showing a result of the simulation performed according to Embodiment 1, in regard to reconstructed images of the object. (a) of FIG. 6 shows an image of an amplitude distribution of a light component polarized in P1 in a reconstructed image; (b) of FIG. 6 shows an image of an amplitude distribution of a light component polarized in P2 in the reconstructed image; (c) of FIG. 6 corresponds to (a) of FIG. 6 and shows an image of a phase distribution of the light component polarized in P1 in the reconstructed image; and (d) of FIG. 6 corresponds to (b) of FIG. 6 and shows an image of a phase distribution of the light component polarized in P2 in the reconstructed image. It is clear that precise and sharp reconstructed images and precise phase distributions can be obtained in Embodiment 1, even when four types of interference patterns of respective varying combinations of phases and polarization directions are obtained by dividing, into 4 patterns, an interference pattern whose image is captured.

(a) to (d) of FIG. 7 show images showing Stokes parameters obtained from the phase distributions and the reconstructed images which are obtained in the simulation. (a) of FIG. 7 shows an image illustrating the Stokes parameter S0 of the reconstructed images; (b) of FIG. 7 shows an image illustrating the Stokes parameter S1 of the reconstructed images; (c) of FIG. 7 shows an image illustrating the Stokes parameter S2 of the reconstructed images; and (d) of FIG. 7 shows an image illustrating the Stokes parameter S3 of the reconstructed images. In comparison of (a) to (d) of FIG. 7 with (a) to (d) of FIG. 5, it is clear that original Stokes parameters could be reproduced precisely in the polarization imaging simulation according to Embodiment 1. That is, in Embodiment 1, it is possible to perform polarization imaging by precisely obtaining a three-dimensional structure of a dynamically-changing object and a detailed polarized-light distribution state of the dynamically-changing object.

<Comparison of Measurable Areas>

In Embodiment 1, the image pickup plane is divided into four and multiple holographic recording (multiple recording of interference patterns) is performed. However, because an in-lint type optical system is employed in Embodiment 1, a photographable area, i.e., a size of a measurable object becomes larger as compared to that of Non-Patent Literature 1 which employs an off-axis type optical system.

(a) of FIG. 8 is a view illustrating a photographable area of the polarization imaging apparatus of Embodiment 1 and a photographable area of an off-axis type polarization imaging apparatus. In this comparative view, the reference light is assumed as collimated light. The polarization imaging apparatus of Embodiment 1 can capture an image of a larger object (larger area) as compared to the off-axis type polarization imaging apparatus. Note that the followings were conditions under which the photographable area shown in (a) of FIG. 8 was obtained: a pixel pitch of the image pickup element was 1.8 μm; a laser light wavelength was 532 nm; an area of the image pickup plane was 1.84 mm×1.84 mm; and a distance between the object and the image pickup plane was 300 mm. Note also that the photographable area is defined as an area (view) whose sharp reconstructed image can be obtained. In an area out of the photographable area, there occur problems such as superposition of zero-order diffracted light or a conjugate image, the occurrence of aliasing and a ghost image caused by the aliasing, and the like. These problems result in deterioration in image quality. The area whose sharp reconstructed image can be captured is a limited area where the above problems do not occur.

When an image pickup element having a large pixel pitch is employed, a difference between the polarization imaging apparatus of the present invention and the off-axis type polarization imaging apparatus becomes more significant. (b) of FIG. 8 is a view illustrating a photographable area of the polarization imaging apparatus of the present invention and a photographable area of the off-axis type polarization imaging apparatus. The followings are conditions under with the photographable area shown in (b) of FIG. 8 was obtained: a pixel pitch of the image pickup element was 5 μm; a laser light wavelength was 532 nm; an area of the image pickup plane was 2.56 mm×2.56 mm; and a distance between the object and the image pickup plane was 300 mm. In this case, it is clear that the polarization imaging apparatus of Embodiment 1 can capture an image of an object (area) that is four or more times as large as an object whose image can be captured by the off-axis type polarization imaging apparatus.

Embodiment 2

The following discusses in detail Embodiment 2 with reference to FIGS. 9 and 10. In Embodiment 2, the number of light sources is 1; in regard to reference light, the number of light components polarized in different directions is 2; and in regard to light components polarized in first and second directions, the number of different phases is 2. For convenience, members and configurations having the same functions as those discussed in Embodiment 1 are given identical reference signs and only explanations of differences from Embodiment 1 are given below.

FIG. 9 is a view schematically illustrating a configuration of a polarization imaging apparatus 2 according to Embodiment 2. The polarization imaging apparatus 2 includes a laser light source 11. The laser light source 11 emits linearly-polarized laser light that includes a light component polarized in the second direction (vertical direction). The polarization imaging apparatus 2 includes a ½ wave plate 36 that regulates a polarization direction, a first spatial light modulator (first modulator) 37 that regulates a polarization direction, and a second spatial light modulator (second modulator) 38 that regulates a polarization direction and that also performs phase shift. The polarization imaging apparatus 2 does not include a phase-shift-array device and a polarizer-array device of Embodiment 1.

After vertically-polarized object light has been produced by splitting laser light by a beam splitter 16, the ½ wave plate 36 turns by 45° a polarization direction of the vertically-polarized object light so that the vertically-polarized object light is converted to polarized light whose vertically-polarized-light component is equal to a horizontally-polarized light component. This object light (obliquely-polarized object light) is thrown onto the object 18, including the vertically-polarized-light component and the horizontally-polarized-light component. After having passed through the object 18 and diffracted by the object 18, the object light is reflected by a beam-combining element 19 and enters an image pickup plane 12a of an image pickup element 12. Note that the object light may be turned to circularly-polarized light or elliptically-polarized light by a ¼ wave plate or the like.

Meanwhile, after vertically-polarized reference light has been produced by splitting the laser light by the beam splitter 16, the vertically-polarized reference light is reflected by a mirror 20 and passes through two spatial light modulators 37 and 38. (a) of FIG. 10 is a plan view schematically illustrating a part of the first modulator 37. The first modulator (polarization-direction-changing-array section) 37 includes (i) a plurality of first-direction regions 37a each of which turns by 90° a polarization direction of laser light passing through a first-direction region 37a, and (ii) a plurality of second-direction regions 37b each of which transmits laser light without changing a polarization direction. When the vertically-polarized reference light enters a first-direction region 37a, the polarization direction of the vertically-polarized reference light is turned by 90° to become horizontally-polarized reference light. Then, the horizontally-polarized reference light exits from the first-direction region 37a. Meanwhile, when the vertically-polarized reference light enters the second-direction region 37b, the vertically-polarized reference light directly exits from the second-direction region 37b as the vertically-polarized reference light. The first modulator 37 is configured by an arrangement where a line of first-direction regions 37a and a line of second-direction regions 37b are alternately provided in a vertical direction. Note that the polarization direction of incident reference light, effects of the first-direction regions and the second-direction regions are not limited to above-described examples. The first modulator only needs to be configured such that: (i) the first-direction regions each convert incident reference light to reference light polarized in a first direction and (ii) the second-direction regions each convert the incident reference light to reference light polarized in a second direction.

(b) of FIG. 10 is a plan view schematically illustrating a part of a second modulator 38. The second modulator (phase-shift-array section) 38 includes plural regions that provide mutually different phases to laser light having passed through the second modulator 38. The second modulator 38 includes two types of phase-shift regions 38a and 38b. The reference light having passed through a phase-shift region 38b has a phase shifted by $(-\pi/2)$ (delayed by $\pi/2$) relative to a phase of the reference light having passed through a phase-shift region 38a, regardless of the polarization direction of the reference light. The phase discussed here is a phase on a plane perpendicular to a reference light propagation direction. For convenience, the reference light having passed through the phase-shift region 38a is referred to as zero-shift reference light, while the reference light having passed through the phase-shift region 38b is referred to as $(-\pi/2)$ shift reference light. The second modulator 38 is configured in an arrangement where a line of phase-shift regions 38a and a line of phase-shift regions 38b are alternately provided in a lateral direction.

The first modulator 37 and the second modulator 38 are bonded to each other. The reference light having passed through the first modulator 37 and the second modulator 38 is split into four types of reference light corresponding to respective varying combinations of two types of polarization and two types of phases, as shown in (c) of FIG. 10. (c) of FIG. 10 corresponds to (b) of FIG. 10 and is a view schematically illustrating a state of a part of the reference light that has just passed through the second modulator 38. The reference light having passed through a region 39a is horizontally-polarized zero-shift reference light. The reference light having passed through a region 39b is horizontally-polarized $(-\pi/2)$ shift reference light. The reference light having passed through a region 39c is vertically-polarized zero-shift reference light. The reference light having passed through a region 39d is vertically-polarized $(-\pi/2)$ shift reference light. As a result of passage through the second modulator 38, these four types of reference light diverge and propagate forward. Then, by an image-forming optical section 22, image formation of the four types of reference light is performed at respective pixels on the image pickup plane 12a of the image pickup element 12.

On the image pickup plane 12a, interference patterns each are formed by interference between obliquely-polarized object light and each of the four types of reference light. In other words, each pixel of the image pickup plane 12a measures light intensity of light resulting from interference between the obliquely-polarized object light and one of the four types of reference light. Thereby, it becomes possible to simultaneously capture an image of each of the four types of interference patterns by the image pickup element 12 that includes no polarizer-array device or the like. The four types of interference patterns are: (i) an interference pattern formed by horizontally-polarized-light components of the object light and the zero-shift reference light, (ii) an interference pattern formed by horizontally-polarized-light components of the object light and the $(-\pi/2)$ reference light, (iii) an interference pattern formed by vertically-polarized light components of the object light and the zero-shift reference light, and (iv) an interference pattern formed by vertically-polarized-light components of the object light and the $(-\pi/2)$ shift reference light.

Subsequently, as in Embodiment 1, polarization imaging can be performed by (i) obtaining complex amplitude distributions of the object light, (ii) generating reconstructed images and phase distributions, and (iii) obtaining Stokes parameters.

In Embodiment 2, a polarization imaging camera including a polarizer-array device is not necessary, and it is possible to realize polarization imaging only by a simple image pickup element. Further, an aberration caused by the image-forming optical section 22 can be compensated by either of the spatial light modulators 37 and 38. In addition, in Embodiment 2, the two spatial light modulators 37 and 38 are aligned in a path of the reference light and affect only the reference light. Accordingly, it becomes easy to regulate the image-forming optical section 22.

Note that in a configuration of Embodiment 1 in which a polarizer array is bonded to an image pickup plane of an image pickup element, the following problems arise. That is, (i) when the polarizer array is bonded in a distorted state, a light phase may also be distorted; and (ii) when the polarizer array and the image pickup element are bonded, misalignment may occur. Once the polarizer array and the image pickup element are bonded, correction of the bonding is impossible. On the contrary, Embodiment 2 has a feature such that it is not necessary to bond the polarizer array and the image pickup element to each other. Accordingly, it is easy to regulate an optical system.

Though two light beams in one polarization direction interfere with each other, two light beams in respective different polarization directions never interfere. For example, at a pixel where the obliquely-polarized object light and the horizontally-polarized zero-shift reference light enter, a vertically-polarized-light component of the object light causes no interference though a horizontally-polarized-light component of the object light interferes with the reference light. Meanwhile, at a pixel where the obliquely-polarized object light and the vertically-polarized zero-shift reference light enter, a horizontally-polarized-light component of the object light causes no interference though a vertically-polarized-light component of the object light interferes with the reference light. Accordingly, the image pickup element 12 measures even a polarized-light component that is not involved in interference of the object light. However, an influence of the polarized-light component that is not involved in the interference of the object light can be removed together with an influence of zero-order diffracted light in a calculation process performed by a phase shift method. The following discusses a method for removing the influence of the polarized-light component of the object light which is not involved in interference.

<Method for Calculating Complex Amplitude Distributions of Object Light>

An intensity $A_o^2(x,y)$ of the object light on the image pickup plane 12a can be expressed by the following expression.

[Expression 1]

$$A_o^2(x,y) = A_{oP1}^2(x,y) + A_{oP2}^2(x,y) \quad (1)$$

In Expression 1, $A_{oP1}^2(x,y)$ is an intensity of a light component of the object light which light component is polarized in a horizontal direction (P1); and $A_{oP2}^2(x,y)$ is an intensity of a light component of the object light which light component is polarized in a vertical direction (P2).

It is assumed that: (i) $I_A(x,y)$ is a light intensity detected by a pixel where the horizontally-polarized zero-shift reference light enters; (ii) $I_B(x,y)$ is a light intensity detected by a pixel where the horizontally-polarized $(-\pi/2)$ shift reference light enters; (iii) $I_C(x,y)$ is a light intensity detected by a pixel where the vertically-polarized zero-shift reference light enters; and (iv) $I_D(x,y)$ is a light intensity detected by a pixel where the vertically-polarized $(-\pi/2)$ shift reference light enters. The reference light that enters each pixel does not interfere with object light having a polarization direction perpendicular to that of the reference light. Accordingly, light intensities detected by respective pixels can be expressed in the following four expressions.

[Expressions 2]

$$I_A(x,y) = A_{oP1}^2(x,y) + A_{oP2}^2(x,y) + A_P^2(x,y) + 2A_{oP1}(x,y)A_P(x,y)\cos\phi_{oP1}(x,y) \quad (2)$$

$$I_B(x,y) = A_{oP1}^2(x,y) + A_{oP2}^2(x,y) + A_P^2(x,y) + 2A_{oP1}(x,y)A_P(x,y)\cos(\phi_{oP1}(x,y) - \alpha) \quad (3)$$

$$I_C(x,y) = A_{oP1}^2(x,y) + A_{oP2}^2(x,y) + A_P^2(x,y) + 2A_{oP2}(x,y)A_P(x,y)\cos\phi_{oP2}(x,y) \quad (4)$$

$$I_D(x,y) = A_{oP1}^2(x,y) + A_{oP2}^2(x,y) + A_P^2(x,y) + 2A_{oP2}(x,y)A_P(x,y)\cos(\phi_{oP2}(x,y) - \alpha) \quad (5)$$

In the above Expressions 2, $A_r(x,y)$ indicates an amplitude of the reference light on the image pickup plane 12a; and $\phi_{oP1}(x,y)$ and $\phi_{oP2}(x,y)$ respectively indicate phases of light components polarized in P1 and P2 of the object light on the image pickup plane 12a.

By forming (i) an expression according to a two-step phase-shifting method from $I_A(x,y)$ and $I_B(x,y)$ in regard to the light component polarized in P1 and (ii) an expression according to the two-step phase-shifting method from $I_C(x,y)$ and $I_D(x,y)$ in regard to the light component polarized in P1, the following expressions can be obtained

[Expressions 3]

$$A_{oP1}(x,y)\cos\phi_{aP1}(x,y) = \frac{I_A(x,y) - t(x,y)}{2A_r(x,y)} \quad (6)$$

$$A_{oP1}(x,y)\sin\phi_{oP1}(x,y) = \frac{I_B(x,y) - I_A(x,y)\cos\alpha - (1 - \cos\alpha)t(x,y)}{2A_r(x,y)\sin\alpha} \quad (7)$$

$$A_{oP2}(x,y)\cos\phi_{oP2}(x,y) = \frac{I_C(x,y) - t(x,y)}{2A_r(x,y)} \quad (8)$$

$$A_{oP2}(x,y)\sin\phi_{oP2}(x,y) = \frac{I_D(x,y) - I_C(x,y)\cos\alpha - (1 - \cos\alpha)t(x,y)}{2A_r(x,y)\sin\alpha} \quad (9)$$

$$t(x,y) = A_{oP1}^2(x,y) + A_{oP2}^2(x,y) + A_r^2(x,y) \quad (10)$$

In the Expressions 3, $\alpha$ is a phase shift amount (here, $\alpha = -\pi/2$); and $t(x,y)$ is a sum of an intensity of a zero-order diffracted light component and an intensity of a non-interfering component of the object light (i.e., a polarized-light component that is orthogonal to the reference light).

From the above expressions (6) to (9) and a formula $\sin^2\phi_o + \cos^2\phi_o = 1$, it is possible to form a quadratic equation for obtaining $t(x,y)$. As a result, $t(x,y)$ can be expressed in the following expressions.

[Expressions 4]

$$t(x,y) = \frac{v_{P1} - \sqrt{v_{P1}^2 - 4u_{P1}w_{P1}}}{2u_{P1}} \quad (11)$$

$$t(x,y) = \frac{v_{P2} - \sqrt{v_{P2}^2 - 4u_{P2}w_{P2}}}{2u_{P2}} \quad (12)$$

$$u_{P1} = u_{P2} = 2(1 - \cos\alpha) \quad (13)$$

$$v_{P1} = 2(1 - \cos\alpha)(I_A(x,y) + I_B(x,y)) + 4A_r^2(x,y)\sin^2\alpha \quad (14)$$

$$w_{P1} = I_A^2(x,y) + I_B^2(x,y) - 2I_A(x,y)I_B(x,y)\cos\alpha + 4A_r^2(x,y)\sin^2\alpha \quad (15)$$

$$v_{P2} = 2(1 - \cos\alpha)(I_C(x,y) + I_D(x,y)) + 4A_r^2(x,y)\sin^2\alpha \quad (16)$$

$$w_{P2} = I_C^2(x,y) + I_D^2(x,y) - 2I_C(x,y)I_D(x,y)\cos\alpha + 4A_r^2(x,y)\sin^2\alpha \quad (17)$$

Because $I_A(x,y)$, $I_B(x,y)$, $I_C(x,y)$, $I_D(x,y)$, and $A_r(x,y)$ indicate respectively measurable amounts, a value of $t(x,y)$ can be obtained from the above expressions (11) to (17). It is also possible to obtain $A_{oP1}(x,y)$, $A_{oP2}(x,y)$, $\phi_{oP1}(x,y)$, and $\phi_{oP2}(x,y)$ that are pieces of desired information for expressing a complex amplitude distribution of each polarized-light component of the object light, from t(x,y) obtained above and the expressions (6) to (9). In this way, by removing the influence of the polarized-light component of the object light which is not involved in interference, it is possible to obtain a complex amplitude distribution of each polarized-light component of the object light.

Embodiment 3

The following discusses in detail Embodiment 3 with reference to FIG. 11. In Embodiment 3, the number of light sources is 1; in regard to reference light, the number of light components polarized in different directions is 2; and in regard to light components polarized in first and second directions, the number of different phases 2. For convenience, members and configurations having the same functions as those discussed in Embodiment 1 are given identical reference signs and only explanations of differences from Embodiment 1 are given below. Embodiment 3 discusses application to a polarization microscope that is suitably used for observation of living samples such as cells.

FIG. 11 is a view schematically illustrating a configuration of a polarization imaging apparatus 3 of Embodiment 3 of the present invention. A laser light source 11 of the polarization imaging apparatus 3 emits laser light in a polarization direction that is inclined at 45° relative to a first direction and that also is in a right-upward direction relative to a propagation direction of the laser light. Note that laser light may be turned to circularly-polarized light by a ¼ wave plate. The polarization imaging apparatus 3 includes a spatial modulator 40, an image-forming optical section (wavefront-transforming section) 41, a spatial-filtering element 42, and a microscope objective lens 43. The polarization imaging apparatus 3 does not include a phase-shift-array device of Embodiment 1. Having passed through an object 18 and diffracted by the object 18, object light is magnified by a microscope objective lens (magnifying optical section) 43. That is, in observation of the object 18 through the microscope objective lens 43, a magnified image of the object 18 can be observed. The object light having passed through the microscope objective lens 43 is reflected by a beam-combining element 19 and enters an image pickup plane 12a of an image pickup element 12.

Meanwhile, reference light having been split by a beam splitter 16 is reflected by a mirror 20 and passes through a spatial light modulator (phase-shift-array section) 40. Like a spatial light modulator 38 shown in (b) of FIG. 10, the spatial light modulator 40 acts on the reference light passing through the spatial light modulator 40 and shifts a phase of the reference light. That is, the spatial light modulator 40 includes two types of regions, and shifts by ($-\pi/2$) a phase of the reference light having passed through a second region, relative to a phase of the reference light having passed through a first region.

The reference light having passed through the spatial light modulator 40 passes through the image-forming optical section 41, the spatial-filtering element 42, the beam-combining element 19, and a polarizer-array device 23, and then enters the image pickup plane 12a. Images of two types of reference light having passed through the spatial light modulator 40 are formed at respective pixels of the image pickup plane 12a of the image pickup element 12, by the image-forming optical section 41 and the spatial-filtering element 42. Note that the image-forming optical section 41 causes the reference light to exit, as a spherical wave (or aspherical wave), from the image-forming optical section 41. The spatial-filtering element 42 has a pinhole, and removes a reference light component which has passed through cells of the spatial light modulator 40 and diffracted by these cells. This makes it possible to obtain reference light having a spherical wave (or aspherical wave) of a regular shape. Then, the reference light enters, as a spherical wave (or aspherical wave), the image pickup plane 12a of the image pickup element 12.

As in Embodiment 1, the polarizer-array device 23 selectively transmits only light components of the object light and the reference light which light components are polarized in either a first direction (horizontal direction) or in a second direction (vertical direction). Accordingly, the image pickup plane 12a includes: (i) a pixel where horizontally-polarized object light interferes with horizontally-polarized zero-shift reference light; (ii) a pixel where the horizontally polarized object light interferes with horizontally-polarized ($-\pi/2$) shift reference light; (iii) a pixel where the vertically-polarized object light interferes with the vertically-polarized zero-shift reference light; and (iv) a pixel where the vertically-polarized object light interferes with the vertically-polarized ($-\pi/2$) shift reference light.

The object light diffracted at a point of the object 18 and diverges from the point reaches the image pickup plane 12a, as a spherical wave (or aspherical wave). When the reference light enters the image pickup plane 12a as a plane wave from a direction perpendicular to the image pickup plane 12a, an incident angle of the reference light in the form of a plane wave entering the image pickup plane 12a becomes partially different from an incident angle of the object light in the form of a spherical wave (or aspherical wave) entering the image pickup plane 12a. The difference between these incident angles indicates that a spatial frequency of an interference pattern formed on the image pickup plane 12a becomes high (a distance between interference fringes becomes narrow). Consequently, a high-resolution image pickup element is required for recording a detailed three-dimensional structure of an object.

In Embodiment 3, the reference light is caused to enter the image pickup plane 12a, after having been converted to a spherical wave (or aspherical wave) in accordance with the object light. This makes it possible to reduce a difference in angle between an object-light propagation direction and a reference-light propagation direction and to widen a distance between interference fringes. Consequently, it becomes possible to record, by a low-resolution image pickup element, interference patterns including information on a detailed three-dimensional structure of the object. Therefore, in the polarization imaging apparatus 3 of Embodiment 3, it is possible to more accurately observe, by polarization imaging, details of an image of the object 18 which is magnified by the microscope objective lens 42. Note that it is possible to apply, to a polarization microscope, a configuration in which the reference light is caused to directly enter the image pickup plane 12a in the form of a plane wave.

Note that different from Embodiment 3, it is not possible to observe details at a high accuracy in a configuration in which an off-axis type optical system is employed (Non-Patent Literature 1). This is because the configuration employing the off-axis type optical system is originally required to have a difference between respective incident angles of the object light and the reference light.

Embodiment 4

The following discusses in detail Embodiment 4 with reference to FIGS. 12 and 18. For convenience, members and configurations having the same functions as those discussed in Embodiment 1 are given identical reference signs and only explanations of differences from Embodiment 1 are given below. Embodiment 4 discusses a polarization imaging apparatus that can obtain spectral information by employing laser light beams respectively having three wavelength types.

FIG. 12 is a view schematically illustrating a configuration of a polarization imaging apparatus 4 according to Embodiment 4. In Embodiment 4, the number of light sources is 3; in regard to reference light, the number of light components polarized in different directions is 2 for each light source; and in regard to light components polarized in first and second directions, the number of different phases is 2. The polarization imaging apparatus 4 includes three types of laser light sources 11a, 11b, and 11c that respectively emit laser light beams having respectively different wavelengths, a mirror 44, a beam-combining elements 45 and 46, and a phase-shift-array device 47. Moreover, the polarization imaging apparatus 4 includes a wavelength selection filter 48 and a polarizer-array device 49 which are disposed in front of an image pickup plane 12a of an image pickup element 12.

The laser light source 11a emits laser light (λ1 laser light) having a wavelength λ1; the laser light source 11b emits laser light (λ2 laser light) having a wavelength λ2; and the laser light source 11c emits laser light (λ3 laser light) having a wavelength λ3. The λ3 laser light emitted from the laser light source 11c is reflected by the mirror 44. The λ2 laser light emitted from the laser light source 11b is reflected by the beam-combining element 45. The beam-combining element 46 then aligns optical axes of the λ2 laser light and the λ3 laser light with an optical axis of the λ1 laser light emitted from the laser light source 11a. Respective polarization directions of laser light respectively emitted from the laser light sources 11a, 11b, and 11c are inclined at 45° relative to a first direction and in a right-upward direction relative to a propagation direction of the laser light. Note that the laser light may be turned to circularly-polarized light or the like by a ¼ wave plate. Each of the laser light beams respectively having the above wavelengths is split into object light beam and reference light beam which have a wavelength of thus split laser light beam, by a beam splitter 16.

Reference light beams respectively having the above wavelengths pass through the phase-shift-array device 47. (a) of FIG. 13 is a view schematically illustrating a part of the phase-shift-array device 47. The phase-shift-array device 47 includes plural regions that provide mutually different phases to the laser light beams having passed through the phase-shift-array device 47. The phase-shift-array device 47 is configured by six types of phase-shift regions 47a through 47f. A phase of λ1 reference light having passed through a phase-shift region 47b is shifted by (−π/2) relative to a phase of λ1 reference light having passed through the phase-shift region 47a. A phase of λ2 reference light having passed through the phase-shift region 47d is shifted by (−π/2) relative to a phase of λ2 reference light having passed through the phase-shift region 47c. A phase of λ3 reference light having passed through the phase-shift region 47f is shifted by (−π/2) relative to a phase of λ3 reference light having passed through the phase-shift region 47e. The above phase shift is performed regardless of a polarization direction of the reference light and each phase discussed above is a phase on a plane perpendicular to a reference light propagation direction. Note that for example, displacement of the phase of the λ2 reference light or λ3 reference light having passed through the phase-shift regions 47a or 47b is insignificant. This is because the λ2 reference light and the λ3 reference light each having passed through the phase-shift region 47a or 47b is subsequently blocked by the wavelength selection filter 48 and therefore is not detected by the image pickup element 12. For convenience, the reference light having passed through any of the phase-shift regions 47a, 47c, and 47e is referred to as zero-shift reference light, while the reference light having passed through any of the phase-shift regions 47b, 47d, and 47f is referred to as (−π/2) shift reference light.

In the phase-shift-array device 47, the above 6 types of phase-shift regions 47a to 47f are provided in an arrangement as shown in (a) of FIG. 13 and a structure of 4×4 cells as shown in (a) of FIG. 13 is periodically provided in an array. The phase-shift-array device 47 can be made of, for example, glass, and configured by changing thickness of the glass for each phase-shift region.

The reference light having passed through the phase-shift-array device 47 passes through an image-forming optical section 22, a beam-combining element 19, the wavelength selection filter 48, and the polarizer-array device 49, and then enters the image pickup plane 12a. When the reference light enters the image pickup plane 12a, an optical axis of the reference light is substantially perpendicular to the image pickup plane 12a. The reference light having passed through the phase-shift-array device 47 is diffracted and an image is formed on the image pickup plane 12a by the image-forming optical section 22. The image-forming optical section 22 is configured by a plurality of lenses. For example, an image is formed at one pixel of the image pickup plane 12a, from the reference light having passed through one phase-shift region 47a of the phase-shift-array device 47. That is, an image is formed at one pixel of the image pickup plane 12a from the reference light having passed through one cell among the phase-shift regions 47a to 47f of the phase-shift-array device 47 partitioned by a grating.

Meanwhile, having been diffracted or scattered by an object 18, the object light of each of the above wavelengths is reflected by the beam-combining element 19, passes through the wavelength selection filter 48 and the polarizer-array device 49, and then enters the image pickup plane 12a of the image pickup element 12.

(b) of FIG. 13 is a view schematically illustrating a part of the wavelength selection filter 48 viewed from an image pickup plane 12a side. The wavelength selection filter 48 is a filter that selectively transmits light depending on a wavelength, and includes a plurality of first wavelength-selecting regions 48a, a plurality of second wavelength-selecting regions 48b, and a plurality of third wavelength-selecting regions 48c. The first wavelength-selecting regions 48a transmit light having the wavelength λ1 and block light having the wavelengths λ2 and λ3; the second wavelength-selecting regions 48b transmit light having the wavelength λ2 and block light having the wavelengths λ1 and λ3; and the third wavelength-selecting regions 48c transmit light having the wavelength λ3 and block light having the wavelengths λ1 and λ2.

(c) of FIG. 13 is a plan view schematically illustrating a part of the polarizer-array device 49 viewed from an image pickup plane 12a side. The polarizer-array device 49 includes a plurality of polarizers 49a and a plurality of polarizers 49b. The polarizers 49a extract only a light component of transmitted light which is polarized in one specified direction (here, horizontal direction), while the polarizers 49b extract only a light component of transmitted light which is polarized in another direction (here, vertical direction) perpendicular to the one specified direction. Incident reference light and incident object light each include a horizontally-polarized-light component and a vertically-polarized-light component. In Embodiment 4, the first direction is the horizontal direction while a second direction is the vertical direction. That is, the polarizers 49a and 49b each transmit only light components of the reference light and the object light corresponding to a polarization direction of each of the polarizers 49a and 49b.

The object light and the reference light having passed through the polarizer-array device 49 enter the image pickup plane 12a at the back of the polarizer-array device 49. The pixels of the image pickup plane 12a each detect a light intensity associated with interference between the object light and the reference light. Then, the image pickup element 12 captures an image of an interference pattern formed on the image pickup plane 12a from the object light and the reference light. Because the polarizer-array device 49 and the wavelength selection filter 48 are bonded next to each other to the image pickup plane 12a, one pixel of the image pickup plane 12a corresponds to (i) one of wavelength-selecting regions 48a to 48c of the wavelength selection filter 48 partitioned by a grating and (ii) one of the polarizers 49a and 49b of the polarizer-array device 49 partitioned by a grating. Further, an image is formed by the image-forming optical section 22 from the reference light that has passed through one cell (one of the phase-shift regions 47a to 47f) among cells of the phase-shift-array device 47 partitioned by a grating. Then, the reference light passes through one of the wavelength-selecting regions 48a to 48c of the wavelength selection filter 48 and one polarizer 49a or 49b of the polarizer-array device 49.

Therefore, the image pickup plane 12a has 12 types in total of pixels subjected to interference. The 12 types of pixels correspond to respective varying combinations of two types of polarization directions and two types of phases of the reference light for each of respective laser light beams of the three types of wavelengths. FIG. 14 is a view illustrating a part of an interference pattern 50 obtained by the polarization imaging apparatus 4. The interference pattern 50 includes the following 12 types of pixels: (a) a pixel 51a where horizontal components of the object light and zero-shift λ1 reference light interfere; (b) a pixel 51b where horizontal components of the object light and (−π/2) shift λ1 reference light interfere; (c) a pixel 51c where vertical components of the object light and zero-shift λ1 reference light interfere; (d) a pixel 51d where vertical components of the object light and (−π/2) shift λ1 reference light interfere; (e) a pixel 51e where horizontal components of the object light and zero-shift λ2 reference light interfere; (f) a pixel 51f where horizontal components of the object light and (−π/2) shift λ2 reference light interfere; (g) a pixel 51g where vertical components of the object light and zero-shift λ2 reference light interfere; (h) a pixel 51h where vertical components of the object light and (−π/2) shift λ2 reference light interfere; (i) a pixel 51i where horizontal components of the object light and zero-shift λ3 reference light interfere; (j) a pixel 51j where horizontal components of the object light and (−π/2) shift λ3 reference light interfere; (k) a pixel 51k where vertical components of the object light and zero-shift λ3 reference light interfere; and (l) a pixel 51l where vertical components of the object light and (−π/2) shift λ3 reference light interfere.

A computer 13 obtains, from the image pickup element 12, image data indicative of the interference pattern 50 whose image is captured by the image pickup element 12. The computer 13 includes a reconstructing section 24. The reconstructing section 24 extracts each of the 12 types of pixels 51a to 51l. This allows obtaining interference patterns corresponding to respective types of pixels, that is, interference patterns like the interference patterns 28a to 28d shown in FIG. 3 for each of the laser light beams respectively having the three types of wavelengths. Then, in each of thus obtained interference patterns, missing pixels are interpolated as in Embodiment 1, and a two-step phase-shifting method is used for obtaining six types of complex amplitude distributions for respective varying combinations of the wavelengths and the polarized light components. Consequently, reconstructed images of the object 18 and phase distributions of the object 18 can be obtained.

Further, a polarization-state-calculating section 25 can (i) calculate Stokes parameters of the reconstructed images for each of the wavelengths, from the reconstructed images and the phase distributions which are obtained above, and (ii) obtain a detailed polarization state. A polarized-light-image-generating section 35 can (i) color the amplitude distribution separately for each of polarization direction of each of the wavelengths, and (ii) generate object images indicative of respective polarized-light distributions for the wavelengths. In this way, in the polarization imaging apparatus 4 of the present invention, spectral diffraction is performed by using the laser light sources 11a to 11c. This makes it possible to simultaneously perform (by one image pickup) polarization imaging for each of the wavelengths.

Note that the order of providing the wavelength selection filter 48 and the polarizer-array device 49 may be reversed. Accordingly, it is possible to configure Embodiment 4 by using a commercially-available color CCD camera to which a wavelength selection filter is bonded, and to obtain spectral information. Note further that the wavelength selection filter 48 employed in Embodiment 4 has a Bayer arrangement, for obtaining an interference pattern of spectrally diffracted light for each of the wavelengths. However, the present invention is not limited to the configuration employing the wavelength selection filter 48. The present invention may alternatively employ (i) a three-sheet-structure image pickup element that captures, by spectral diffraction with use of a prism, respective images of interference patterns which respectively correspond to the wavelengths and which are respectively formed on three image pickup planes, (ii) an image pickup element (See Non-Patent Literature 4) that separately detects light having a plurality of wavelengths (red, green and blue) with use of one pixel, by utilizing a characteristic of a silicon sensor such that light is absorbed at different depths depending on wavelengths, or the like.

<Simulation Results>

The inventors of the present invention performed, on a computer, simulation in which reconstructed images are generated and Stokes parameters are calculated according to Embodiment 4. The following explains a result of this simulation.

An optical system for capturing an object image is the polarization imaging apparatus 4 shown in FIG. 12. (a) of FIG. 15 shows an image of an amplitude distribution of a light component polarized in a horizontal direction (P1) which amplitude distribution indicates apparent lightness of an object. (b) of FIG. 15 shows an image of an amplitude distribution of a light component polarized in a vertical direction (P2) which amplitude distribution indicates apparent lightness of the object. The object has a square cross section along a plane perpendicular to a direction in which the object light passes through the object. On the object, an image of a letter "KIT" is formed. (c) of FIG. 15 corresponds to (a) of FIG. 15 and shows an image of a phase distribution in a case where laser light polarized in the horizontal direction (P1) passes through the object. (d) of FIG. 15 corresponds to (b) of FIG. 15 and shows an image of a phase distribution in a case where laser light polarized in the vertical direction (P2) passes through the object. In (c) and (d) of FIG. 15, a phase delay is expressed in the lightness. A phase of laser light (object light) in the darkest region is delayed by 2π relative to a phase of laser light in the brightest region.

FIG. 16 shows images illustrating respective Stokes parameters S0 to S3 for each of object light beams respectively having the wavelengths λ1 to λ3 which object light beams have been diffracted by the object. In FIG. 16, a brighter region has a larger Strokes parameter.

Note that conditions for the simulation were assumed as below: (i) wavelengths of laser light employed were λ1=633 nm (red:R), λ2=532 nm (green:G), and λ3=473 nm (blue:B); (ii) a cross section size of the object (a size in terms of length and width of an image shown in (a) of FIG. 4) was 3.69 mm×3.69 mm; (iii) a distance between the object and the image pickup plane of the image pickup element (a distance along an optical axis of the object light) was 50 mm; (iv) a size of each pixel of the image pickup element was 1.8 μm×1.8 μm; (v) the number of pixels of the image pickup element was 2048×2048 pixels; and (vi) a pixel pitch was 1.8 μm. Under the above conditions, the simulation was performed on a computer. The simulation included the steps of (i) obtaining interference patterns formed on the image pickup plane from the object light of the object and the reference light; (ii) calculating reconstructed images; and (iii) obtaining Stokes parameters of the reconstructed images from the reconstructed images. Note that the interference patterns were also obtained from the simulation performed on the computer.

(a) to (d) of FIG. 17 show images showing a result of the simulation performed in accordance with Embodiment 4, in regard to reconstructed images of the object. (a) of FIG. 17 shows an image of an amplitude distribution indicating a sum of amplitude distributions of respective light components polarized in P1 in the reconstructed images of the wavelengths; (b) of FIG. 17 shows an image of an amplitude distribution indicating a sum of amplitude distributions of respective light components polarized in P2 in the reconstructed images of the wavelengths; (c) of FIG. 17 corresponds to (a) of FIG. 17 and shows an image of a phase distribution of the light components polarized in P1 in the reconstructed images; and (d) of FIG. 17 corresponds to (b) of FIG. 17 and shows an image of a phase distribution of the light components polarized in P2 in the reconstructed images. Note that the phase distributions in (c) and (d) of FIG. 17 each indicate a phase distribution at a given wavelength, because no dependency on wavelength was set as a condition for the simulation in regard to the phase distributions. It is clear that precise and sharp reconstructed images and precise phase distributions can be obtained in Embodiment 4, even when 12 types of interference patterns for respective varying combinations of phases and polarization directions are obtained by dividing, into 12 patterns, an interference pattern whose image is captured.

FIG. 18 shows images respectively illustrating Stokes parameters S0 to S3 obtained for each of object light beams respectively having wavelengths λ1 to λ3, from the phase distributions and the reconstructed images which are obtained in the simulation. It is clear from comparison of FIG. 18 with FIG. 16, original Stokes parameters could be reproduced accurately in the simulation of polarization imaging of Embodiment 4. That is, in Embodiment 4, it is possible (i) to accurately obtain a three-dimensional structure of a dynamically-changing object and a detailed polarization state of such an object in regard to a plurality of wavelengths and (ii) to perform spectral imaging and polarization imaging.

Note that in Embodiment 4, the laser light employed have three types of wavelengths. However, the laser light may have two or more than three types of wavelengths. Further, the wavelengths of light may be a wavelength of not only visible light, but also a wavelength of infrared, ultraviolet, X-ray, or the like.

Embodiment 5

The following discusses in detail Embodiment 5 with reference to FIGS. 19 and 20. In Embodiment 5, for convenience, members and configurations having the same functions as those discussed in Embodiment 1 are given identical reference signs, and only explanations of differences from Embodiment 1 are given below. Embodiment 5 describes an embodiment including an in-line type optical system utilizing an optical-path-length shift method.

FIG. 19 is a view schematically illustrating a configuration of a polarization imaging apparatus 5 according to Embodiment 5. In Embodiment 5, the number of light sources is 1; in regard to reference light, the number of light components polarized in different directions is 2; and in regard to light components polarized in first and second directions, the number of different phases is 2. The polarization imaging apparatus 5 includes a laser light source 11. Laser light emitted from the laser light source 11 has polarization directions which are inclined at 45° relative to the first direction and in a right-upward direction relative to a laser light propagation direction. Note that the laser light may be changed into circularly-polarized light or the like by a ¼ wave plate. The polarization imaging apparatus 5 includes an optical-path-length shift array (optical-path-length-shift-array section having a phase shift adjusting function) 52 disposed in front of an image pickup plane 12a of an image pickup element 12. The optical-path-length-shift-array device 52 and a polarizer-array device 23 are bonded next to each other in front of the image pickup plane 12a. The polarization imaging apparatus 5 does not include a phase-shift-array device 21 and an image-forming optical section 22.

Object light having passed through an object 18 and diffracted by the object 18 is reflected from a beam-combining element 19 and then enters the image pickup plane 12a of the image pickup element 12.

Meanwhile, reference light into which the laser light has been split by a beam splitter 16 is reflected from a mirror 20. The reflected light passes through the beam-combining element 19 and then enters the image pickup plane 12a of the image pickup element 12 at an incidence angle substantially perpendicular to the image pickup plane 12a.

The object light and the reference light each pass through the polarizer-array device 23 and the optical-path-length-shift-array device 52 and then enter the image pickup plane 12a. The polarizer-array device 23 employed in Embodiment 5 is the one shown in (b) of FIG. 2.

FIG. 20 is a view schematically illustrating a part of the optical-path-length-shift-array device 52 viewed from the image pickup plane 12a side. The optical-path-length-shift-array device 52 has plural regions that provide mutually different optical path lengths to the laser light beams having passed through the respective regions. In Embodiment 5, the optical-path-length-shift-array device 52 has optical-path-length-shifting regions 52a and 52b each constituted by respective ¼ wave plates whose optical axes are orthogonal to each other. A fast axis of the optical-path-length-shifting region 52a is identical to a horizontal direction, while a slow axis of the optical-path-length-shifting region 52a is identical to a vertical direction. A fast axis of the optical-path-length-shifting region 52b is identical to a vertical direction, while a slow axis of the optical-path-length-shifting region 52b is identical to a horizontal direction. Therefore, horizontally-polarized reference light and horizontally-polarized object light having passed through the optical-path-length-shifting region 52b are phase-shifted by $(-\pi/2)$ relative to horizontally-polarized reference light and horizontally-polarized object light having passed through the optical-path-length-shifting region 52a. That is, an optical path difference of ¼ wavelength occurs in an optical path length between the object 18 and the image pickup plane 12a. On the other hand, vertically-polarized reference light and vertically-polarized object light having passed through the optical-path-length-shifting region 52a are phase-shifted by (−π/2) relative to vertically-polarized reference light and vertically-polarized object light having passed through the optical-path-length-shifting region 52b.

Thus, the image pickup plane 12a has pixels subjected to four types of interferences corresponding to varying combinations of two types of polarization directions and two types optical path lengths.

The image pickup element 12 captures an image of an interference pattern which is formed on the image pickup plane 12a and which includes the four types of interferences. As in Embodiment 1, a reconstructing section 24 divides pixels into four types of pixels to obtain four types of interference patterns. Thereafter, by utilizing an optical-path-length shift method, the reconstructing section 24 calculates a complex amplitude distribution of horizontally-polarized-light components and a complex amplitude distribution of vertically-polarized-light components. The subsequent processes for the polarization imaging are much the same as those in Embodiment 1. In Embodiment 5, the polarizer-array device 23 and the optical-path-length-shift-array device 52 are attached to the image pickup element 12 by being bonded to the image pickup plane 12a. Once such an image pickup element camera is produced, a subsequent system formation of a polarization imaging apparatus becomes very simple.

Embodiment 6

Embodiment 6 will describe an embodiment of the present invention, wherein a plurality of holograms are obtained by changing an incidence angle of reference light with respect to an image pickup element, instead of using a phase shift device for the reference light.

FIG. 21 is a view schematically illustrating a basic configuration of a polarization imaging apparatus 1a according to Embodiment 6 of the present invention. Constituent components identical to the foregoing constituent components are given the same reference signs and detailed descriptions thereof are not repeated.

The basic configuration in Embodiment 6 is such that reference light is singly made incident, from a direction different from a direction from which object light is incident, on a polarizer-array device 23 provided to an image pickup element 12 of the polarization imaging apparatus 1a. Oblique incidence of reference light makes it possible to obtain a spatially-phase-shifted hologram on an image pickup plane without a device for performing a phase shift function and to extract object information by a simple image processing called a spatial carrier shift method. Thereby, instantaneous three-dimensional polarization imaging is realized.

FIG. 22 illustrates an operating principle of the polarization imaging apparatus 1a. Note that the number of light sources is 1; in regard to reference light, the number of light components polarized in different directions is 2; and in regard to polarized-light components in first and second directions, the number of different phases is 4. This operating principle is the one for obtaining spatially-phase-shifted holograms. Being inclined at an inclination angle θ relative to the object light (which means diffracted light or scattered light from the object) incident from a direction perpendicular to the image pickup plane formed on the image pickup element 12, the reference light is made incident, so that pixels of the image pickup element 12 individually shift phases of incoming reference light by an amount equivalent to the inclination. In this case, the inclination angle θ is expressed by θ=sin−1(λ/4τ), where: λ represents a wavelength of reference light; and τ represents a distance between pixels of the image pickup element 12.

The inclination angle θ is most preferably, but not necessarily limited to, (sin⁻¹(λ/4τ). The effect of the present invention is achievable as long as the inclination angle θ is based on (sin⁻¹(λ/4τ).

Therefore, phases of the reference light on the image pickup plane are successively shifted by a phase shift amount of (π/2) at every distance τ that is a distance between adjacent pixels. For easy understanding, phase shift amounts of the reference light are schematically shown in FIG. 22.

Owing to interference between the reference light and the object light, a spatially-phase-shifted hologram is formed on the image pickup plane, as shown in FIG. 22. The spatial-phase-shift hologram thus obtained is hereinafter referred to as "spatial-carrier-phase-shift hologram". By recording such a spatially-phase-shifted hologram, it is possible to obtain the spatial-carrier-phase-shift hologram by a single shot.

FIG. 23 is a view schematically illustrating the configuration of the polarization imaging apparatus 1a. Note that the number of light sources is 1; in regard to reference light, the number of light components polarized in different directions is 2; and in regard to polarized-light components in first and second directions, the number of different phases is 4. Constituent components identical to the foregoing constituent components are given the same reference signs and detailed descriptions thereof are not repeated. Light emitted from the laser light source 11 has at least polarized-light components whose directions are much the same as those of polarized-light components of polarizers in a polarizer-array device 23. The configuration of the polarizer-array device 23 is identical to the foregoing configuration described with reference to (b) of FIG. 2.

Light emitted from a laser light source 11 is turned into enlarged collimated light and then split into two light waves by a beam splitter 16. One of these light waves is thrown onto an object 18, and diffracted light from the object 18 enters, as object light, an image pickup element 12 with the polarizer-array device 23. The other light wave enters, as reference light, the image pickup element 12 with the polarizer-array device 23 at a given inclination angle relative to the object light.

FIG. 24 illustrates an algorithm for operations of the polarization imaging apparatus 1a. The polarization imaging apparatus 1a shown in FIG. 23 has a computer 13a. The computer 13a has a spatial-carrier-phase-shifting section 53.

First, with the configuration of the image pickup element 12 shown in FIG. 23, a hologram 62 spatially-phase-shifted in polarization directions P1 and P2 is obtained by one image pickup. Thereafter, the spatial-carrier-phase-shifting section 53 extracts interference patterns 63a and 63b corresponding to respective polarization directions P1 and P2. Next, the spatial-carrier-phase-shifting section 53 interpolates missing pixels by using pixels which have orthogonality with respect to a direction in which the reference light has been inclined. It should be noted that Embodiment 6 gives an example where the reference light is inclined in a horizontal direction. Accordingly, FIG. 24 shows an example of performing interpolation by using pixels in the vertical direction. In this manner, spatially-phase-shifted holograms 64a and 64b can be obtained in correspondence with the polarization directions P1 and P2, respectively.

Further, the spatial-carrier-phase-shifting section 53 performs calculation with respect to the obtained holograms 64a and 64b according to a spatial carrier phase shift method, so that complex amplitude distributions 65a and 65b of an object corresponding to the respective polarization directions P1 and P2 can be obtained. Then, on the basis of the complex amplitude distributions 65a and 65b thus obtained, polarization imaging can be performed by using an expression for calculating a polarization state, such as Stokes parameters or Jones vectors.

FIG. 25 illustrates a spatial carrier phase shift method based on the above-described algorism. In this spatial carrier phase shift method, complex amplitude distributions of the object are calculated, according to a phase shift method, from information of adjacent, spatially-phase-shifted holograms. The calculation can be generally performed with any number of steps of phase shift. As an example is given a case where (i) phase shift amounts are different by 90 degrees between adjacent pixels and (ii) the number of steps of phase shift is 3.

For example, in order to find complex amplitudes of the object for respective pixels disposed in a region R5 shown in FIG. 25, calculation based on a phase shift method can be carried out using a hologram having three phase shift amounts of $-\pi/2$, 0, and $-3\pi/2$ which are provided in the region R2 shown in FIG. 25. In order to find complex amplitudes of the object for the pixels disposed in a region R4, calculation based on the phase shift method can be carried out using a hologram having three phase shift amounts of 0, $-3\pi/2$, and $-\pi$ which are provided in the region R1 shown in FIG. 25. In order to find complex amplitudes of the object for respective pixels disposed in a region R6 shown in FIG. 25, calculation based on the phase shift method is performed using a hologram having three phase shift amounts of $-\pi$, $-\pi/2$, and 0 which are provided in a region R3 shown in FIG. 25. Through such a calculation based on the phase shift method, complex amplitude distributions of the object can be found, and a three-dimensional image of the object can be reconstructed by performing diffraction integral with respect to the complex amplitude distributions.

The above case deals with a procedure for the calculation using holograms each having three phase shift amounts by a phase shift method. However, the number of holograms required for the calculation based on the phase shift method needs to be at least two, and the number of phase shift amounts may be 2, 4, or 5.

As described above, Embodiment 6 realizes oblique incidence of single reference light without using any special phase shift elements like a phase-shift-array device 21 and an image-forming optical section 22 which are shown in FIG. 1. This makes it possible to simultaneously implement wide-range, high-definition, instantaneous three-dimensional imaging and polarization imaging with more compact configuration.

Unlike Non-Patent Literature 1, the method using the spatial carrier phase shift method is such that single reference light having respective components of the different polarization directions P1 and P2 is made incident at an angle formed with respect to the object light. Since the light being made incident at a given angle is single reference light, the components of the polarization directions P1 and P2 enter from the same direction. Unlike Non-Patent Literature 1, a phase adjustment amount for the polarization direction P1 is therefore identical to that for the polarization direction P2. Consequently, the present method eliminates the need for a highly precise adjustment, which is required for Non-Patent Literature 1. This eliminates readily decreased accuracy in polarization imaging even when there occurs a change in position of optical element(s), unlike Non-Patent Literature 1.

Note that Embodiment 6 has given an example applied to a transmissive optical system; however, Embodiment 6 can also be implemented by a reflective optical system.

FIG. 26 is a view schematically illustrating a configuration of a polarization imaging apparatus 3a which is another polarization imaging apparatus according to Embodiment 6. Note that the number of light sources is 1; in regard to reference light, the number of light components polarized in different directions is 2; and in regard to polarized-light components in first and second directions, the number of different phases is not less than 2. Constituent components identical to the foregoing constituent components are given the same reference signs and detailed descriptions thereof are not repeated. Embodiment 6 can also be applied to the polarization imaging apparatus 3 shown in FIG. 11 and is configured such that without using a second spatial light modulator 40 and an image-forming optical section 41, reference light is made incident, on a polarizer-array device 23, at an inclination with respect to object light. With this arrangement, it is possible to apply Embodiment 6 to the configuration of a microscope with the microscope objective lens 43.

FIG. 27 is a view schematically illustrating a polarization imaging apparatus 4a which is still another polarization imaging apparatus according to Embodiment 6. Note that the number of light sources is 3; in regard to reference light, the number of light components polarized in different directions is 2; and in regard to polarized-light components in first and second directions, the number of different phases is not less than 2. Constituent components identical to the foregoing constituent components are given the same reference signs and detailed descriptions thereof are not repeated.

Embodiment 6 can also be applied to the polarization imaging apparatus 4 shown in FIG. 12. The polarization imaging apparatus 4a is arranged such that without using a phase-shift-array device 47 and an image-forming optical section 22 which are shown in FIG. 12, reference light originated from a laser light source 11a, reference light originated from a laser light source 11b, and reference light originated from a laser light source 11c are made incident, on a polarizer-array device 49, at an inclination of the same angle with respect to object light. With this arrangement, it is possible to measure spectral characteristics by applying Embodiment 6 to the polarization imaging apparatus 4 to which polarization imaging and spectral imaging are applied.

The reference light originated from the laser light source 11a, the reference light originated from the laser light source 11b, and the reference light originated from the laser light source 11c have mutually different wavelengths. Therefore, the inclination angles $\theta=(\sin^{-1}(\lambda/4\tau))$ of the respective reference light beams are mutually different from one another in a strict sense since these reference light beams have mutually different wavelengths $\lambda$. However, as described previously, the inclination angle $\theta$ is most preferably, but not necessarily limited to, $(\sin^{-1}(\lambda/4\tau)$. The effect of the present invention is achieved as long as the inclination angle $\theta$ is based on $(\sin^{-1}(\lambda/4\tau)$.

In addition, such an arrangement having the same inclination angles unfortunately causes a slightly lower accuracy of an image, but enables easier inclination adjustment to be made, as compared with the arrangement in which adjustment is made to exactly obtain $(\sin^{-1}(\lambda/4\tau))$. This enables shortening of an adjustment time and easy installation.

FIG. 28 is a view schematically illustrating a configuration of a polarization imaging apparatus 3b which is yet another polarization imaging apparatus in Embodiment 6. Note that the number of light sources is 3; in regard to reference light, the number of light components polarized in different directions is 2; and in regard to polarized-light components in first and second directions, the number of different phases is not less than not less than 2. Constituent components identical to the foregoing constituent components are given the same reference signs and detailed descriptions thereof are not repeated. The polarization imaging device 3b is an example of application of the polarization imaging apparatus 3a, which is applied to a microscope shown in FIG. 26, to a spectral imaging application apparatus including lasers 11a through 11c. As with the polarization imaging apparatus 4a shown in FIG. 27, the polarization imaging apparatus 3b is configured such that reference light originated from a laser light source 11a, reference light originated from a laser light source 11b, reference light originated from a laser light source 11c are made incident, on a polarizer-array device 49, at the same inclination angle with respect to object light. Such an arrangement having the same inclination angles unfortunately causes a slightly lower accuracy of an image, but enables easier inclination adjustment to be made, as compared with the arrangement in which adjustment is made to exactly obtain $(\sin^{-1}(\lambda/4\tau))$. This enables shortening of an adjustment time and easy installation.

(a) of FIG. 29 is a view schematically illustrating a configuration of a polarization imaging apparatus 4b which is a further polarization imaging apparatus in Embodiment 6. Constituent components identical to the foregoing components are given the same reference signs and detailed descriptions thereof are not repeated.

The polarization imaging apparatus 4a, which has been described previously with reference to FIG. 27, is configured such that reference light beams having mutually different wavelengths and respectively originated from the laser light sources 11a, 11b, and 11c are made incident at the same inclination angle on the polarizer-array device 49. However, the polarization imaging apparatus 4b is configured such that the reference light beams respectively originated from the laser light sources 11a, 11b, and 11c are each made incident, on the polarizer-array device 49, at the inclination angle θ expressed by $\theta=(\sin^{-1}(\lambda/4\tau))$. Since wavelengths λ of the reference light beams respectively originated from the laser light sources 11a, 11b, and 11c are mutually different from one another, inclination angles θ of these reference light beams are also mutually different from one another.

The laser light source 11a emits laser light having a wavelength λ1, the laser light source 11b emits laser light having a wavelength λ2, and the laser light source 11c emits laser light having a wavelength λ3. The laser light having the wavelength λ3 emitted from the laser light source 11c is split into object light and reference light by a beam-combining element 44a. The laser light having the wavelength λ2 emitted from the laser light source 11b is split into object light and reference light by a beam-combining element 45. The laser light having the wavelength λ1 emitted from the laser light source 11a is split into object light and reference light by a beam-combining element 46.

The object light originated from the laser light source 11c and reflected by the beam-combining element 44a, the object light originated from the laser light source 11b and reflected by the beam-combining element 45, and the object light originated from the laser light source 11a and reflected by the beam-combining element 46 are reflected by a mirror 20. Each reflected light passes through a beam expander 14 and a collimator lens 15 to turn into collimated light. The collimated light is diffracted or scattered by an object 18. The resultant light passes through a beam-combining element 19 and then enters a wavelength selection filter 48 and a polarizer-array device 49.

The reference light originated from the laser light source 11c and having passed through the beam-combining element 44a passes through a beam expander 14c and a collimator lens 15c to turn into collimated light. The collimated light is reflected by the beam-combining element 19. The reflected light enters the wavelength selection filter 48 and the polarizer-array device 49 at an inclination angle $\theta=(\sin^{-1}(\lambda 3/4\tau))$ with respect to the object light.

The reference light originated from the laser light source 11b and having passed through the beam-combining element 45 passes through a beam expander 14b and a collimator lens 15b to turn into collimated light. The collimated light is reflected by the beam-combining element 19. The reflected light enters the wavelength selection filter 48 and the polarizer-array device 49 at an inclination angle $\theta=(\sin^{-1}(\lambda 2/4\tau))$ with respect to the object light.

The reference light originated from the laser light source 11a and having passed through the beam-combining element 46 passes through a beam expander 14a and a collimator lens 15a to turn into collimated light. The collimated light is reflected by the beam-combining element 19. The reflected light enters the wavelength selection filter 48 and the polarizer-array device 49 at an inclination angle $\theta=(\sin^{-1}(\lambda 1/4\tau))$ with respect to the object light.

Since the inclination angle θ is most preferably $(\sin^{-1}(\lambda/4\tau))$ as described previously, the reference light beams respectively originated from the laser light sources 11a, 11b, and 11c can enter the polarizer-array device 49 at the most preferable inclination angle. This makes it possible to improve accuracy of a polarized image.

(b) of FIG. 29 is a view schematically illustrating a configuration of a polarization imaging apparatus 4c which is a still further polarization imaging apparatus in Embodiment 6. Constituent components identical to the foregoing components are given the same reference signs and detailed descriptions thereof are not repeated. For a configuration applied to a microscope with a microscope objective lens 43, the configuration shown in (b) of FIG. 29, as with the configuration shown in (a) of FIG. 29, can be configured such that inclination angles θ of reference light beams originated from laser light sources 11a, 11b, and 11c are different from one another.

(a) of FIG. 30 is a view schematically illustrating a configuration of a polarization imaging apparatus 4d which is yet another polarization imaging apparatus in Embodiment 6. In the polarization imaging apparatus 4d, four light sources are used. Constituent components identical to the foregoing components are given the same reference signs and detailed descriptions thereof are not repeated. The polarization imaging apparatus 4d is an example of the polarization imaging apparatus 4d, shown in (a) of FIG. 29, which is additionally provided with a laser light source 11d that emits laser light having a wavelength λ4. With an arrangement in which the reference light beams having different wavelengths are inclined differently, spectral imaging from a small number of pixels and correspondingly small numbers of filters and sensors is realized.

(b) of FIG. 30 is a view schematically illustrating the configuration of a polarization imaging apparatus 4e which is a yet further polarization imaging apparatus in Embodiment 6. In the polarization imaging apparatus 4e, four light sources are used. Constituent components identical to the foregoing components are given the same reference signs and detailed descriptions thereof are not repeated. The polarization imaging apparatus 4e is an example of the polarization imaging apparatus 4c, shown in (b) of FIG. 29, which is additionally provided with a laser light source 11d that emits laser light having a wavelength λ4. With an arrangement in which the reference light beams having different wavelengths are inclined differently, spectral imaging from a small number of pixels and correspondingly small numbers of filters and sensors is realized.

The above descriptions has given, as examples using a plurality of light sources, the examples using three light sources respectively supplying three types of wavelengths and the examples using four light sources respectively supplying four types of wavelengths. This is not intended to limit the present invention. Alternatively, two light sources respectively supplying two types of wavelengths may be used, or five light sources respectively supplying five types of wavelengths may be used.

FIG. 31 illustrates a method for obtaining plural pieces of wavelength information with use of a single-type image sensor described in Non-Patent Literature 7. An image sensor 66 is a monochrome image sensor capable of recording only luminance information (hereinafter referred to as "single-type image sensor"). Reference light beams having mutually different wavelengths $\lambda_1$, $\lambda_2$, and $\lambda_3$ enter the image sensor 66 respectively at mutually different inclination angles, so that a hologram 67 is formed. Then, in correspondence with the inclination angles of the respective reference light beams, a spatial spectrum of an object is Fourier-transformed, for each wavelength, to be separated into a spatial spectrum 68a of the object at the wavelength $\lambda_1$, a spatial spectrum 68b of the object at the wavelength $\lambda_2$, and a spatial spectrum 68c of the object at the wavelength $\lambda_3$. Subsequently, by filtering the spatial spectrums 68a, 68b, and 68c, it is possible to reconstruct a three-dimensional structure information figure of the object involving desired wavelengths.

Thus, it is possible to obtain spectral image information with use of the monochrome image sensor 66 capable of recording only luminance information. The number of wavelengths that can be recorded by one image pickup may be smaller than 3 or may be larger than 3. Non-Patent Literature 7 uses spatial filtering in an off-axis type arrangement, but does not use the spatial carrier phase shift method. Addition of a calculation processing section utilizing the spatial carrier phase shift method enables wide-range imaging. Furthermore, the use of the single-type image sensor 66 in combination with the present invention enables not only wide-range polarization imaging but also simultaneous obtaining of spectral image information.

(a) of FIG. 32 is a view schematically illustrating a configuration of a polarization imaging apparatus 4f which is another polarization imaging apparatus according to Embodiment 6, and (b) of FIG. 32 illustrates a method for obtaining three-dimensional information, polarization information, and plural pieces of wavelength information with use of a single-type image sensor. FIG. 33 is an oblique view illustrating a configuration of the image pickup element 12 for obtaining three-dimensional information, polarization information, and plural pieces of wavelength information with use of a single-type image sensor. Constituent components identical to the foregoing components are given the same reference signs and detailed descriptions thereof are not repeated.

The following will describe a method for utilizing a spatial carrier shift method by means of the polarizer-array device 49 and the single-type image sensor 66 to obtain three-dimensional information, polarization information, and plural pieces of wavelength information.

The polarization imaging apparatus 4f includes: a laser light source 11a that supplies light having a wavelength $\lambda_1$; and a laser light source 11b that supplies light having a wavelength $\lambda_2$. The image pickup element 12 is provided with a single-type image sensor 66 and the polarizer-array device 49.

An optical axis of the reference light corresponding to the light having the wavelength $\lambda_1$ is made different, in inclination angle at the entry to the image pickup element 12, from an optical axis of the reference light corresponding to the light having the wavelength $\lambda_2$. This enables separation of a spatial spectrum of an object into spatial spectrums corresponding to the respective wavelengths.

Thus, by providing the single-type image sensor 66 in the image pickup element 12, it is possible to record plural pieces of wavelength information without provision of a wavelength selection filter or a multilayered image sensor.

FIG. 34 is a view showing a flow for obtaining three-dimensional images of an object corresponding to the varying combinations of a plurality of polarizations and a plurality of wavelengths from a hologram 69 recorded in the single-type image sensor 66. First, the hologram 69 recorded in the single-type image sensor 66 is separated into interference patterns 70a and 70b for the respective polarization directions P1 and P2. Then, missing pixels in the interference patterns 70a and 70b are interpolated. An interpolation direction is a direction orthogonal to a direction in which reference light has been inclined. Thus, holograms 71a and 71b and holograms 71c and 71d are generated by interpolations performed in interpolation directions that vary depending upon the wavelengths of desired information.

Subsequently, not only spatial filtering but also a calculation based on a spatial carrier phase shift method are utilized to obtain complex amplitude distributions 72a, 72b, 72c, and 72d of the object corresponding to the varying combinations of the specific polarization directions P1 and P2 and the specific wavelengths $\lambda_1$ and $\lambda_2$. Thereafter, three-dimensional images of the object corresponding to the varying combinations of the specific polarization directions P1 and P2 and the specific wavelengths $\lambda_1$ and $\lambda_2$ are reconstructed by diffraction integral.

FIG. 35 is a flow chart showing a flow for reconstructing three-dimensional structures, polarized-light distributions, and spectral images of an object from a recorded hologram. FIG. 35 briefly shows a general flow of performing the steps shown in FIG. 34. Through the flow shown in FIG. 35, three-dimensional structures, polarized-light distributions, and spectral image information of an object are obtained by one image pickup, so that an image is reconstructed.

First, a hologram is recorded in an image pickup element (step S1). Then, interference patterns obtained by separation of image information are extracted in correspondence with the respective polarization directions (step S2). Next, missing pixels in the interference patterns thus extracted are interpolated (step S3). Thereafter, the spatial filtering and the calculation based on the spatial carrier phase shift method are performed (step S4). Then, diffraction integral is performed (step S5). Subsequently, polarization imaging is carried out for each wavelength (step S6). Then, three-dimensional structures, polarized-light distributions, and spectral image information are displayed (step S7).

In the step S4, either of the spatial filtering and the calculation based on the spatial carrier phase shift method may be carried out first.

(a) of FIG. 36 is a view illustrating a configuration of a wavelength-selection-filter array 73 including two types of filters 74a and 74b, and (b) of FIG. 36 illustrates an operation of the wavelength-selection-filter array 73.

The following will describe a method for obtaining three-dimensional information, polarization information, plural pieces of wavelength information according to a spatial carrier phase shift method by means of a polarizer-array device 49 and an image sensor 66 with the wavelength-selection-filter 73 having two types of filters 74a and 74b.

The wavelength-selection-filter array 73 includes filters 74a and filters 74b. For example, the filters 74a each transmit red light having a wavelength $\lambda_1$ and infrared light having a wavelength $\lambda_4$, but blocking light having wavelengths shorter than the wavelength of the red light, and the filters 74b each transmit green light having a wavelength $\lambda_2$ and blue light having a wavelength $\lambda_3$, but blocking light having wavelengths longer than the wavelength of the green light having the wavelength $\lambda_2$.

The filters 74a and the filters 74b are arranged in a matrix manner and arranged alternately in the horizontal direction and in the vertical direction. The filters 74a and the filters 74b may be each constituted by (i) material(s) and structure(s) having a range of wavelength choices for transmissivities and reflectivities, such as absorptive filters, photonic crystals, and others.

On the filters 74a, reference light of the red light having the wavelength $\lambda_1$ and reference light of the infrared light having the wavelength $\lambda_4$ are made incident at different inclination angles. On the filters 74b, reference light of the green light having the wavelength $\lambda_2$ and reference light of the blue light having the wavelength $\lambda_3$ are made incident at different inclination angles.

(a) of FIG. 37 is a view schematically illustrating a configuration of a polarization imaging apparatus 4g which is still another polarization imaging apparatus according to Embodiment 6, and (b) of FIG. 37 is an oblique view illustrating a configuration of an image pickup element 12 provided in the polarization imaging apparatus 4g.

According to (a) of FIG. 37, the reference light of the red light having the wavelength $\lambda_1$ is made different, in inclination angle at the entry to the wavelength-selection-filter array 73, from the reference light of the infrared light having the wavelength $\lambda_4$, and the reference light of the green light having the wavelength $\lambda_2$ is made different in the inclination angle from the reference light of the blue light having the wavelength $\lambda_3$. This makes it possible to separate a spatial spectrum of an object into respective spatial spectrums for the red light having the wavelength $\lambda_1$, the green light having the wavelength $\lambda_2$, the blue light having the wavelength $\lambda_3$, and the infrared light having the wavelength $\lambda_4$. Note that the inclination angle of the red light having the wavelength $\lambda_1$ may be identical to the inclination angle of the green light having the wavelength $\lambda_2$ or the inclination angle of the blue light having the wavelength $\lambda_3$. In addition, the inclination angle of the infrared light having the wavelength $\lambda_4$ may be identical to the inclination angle of the blue light having the wavelength $\lambda_3$ or the inclination angle of the green light having the wavelength $\lambda_2$.

According to (b) of FIG. 37, onto the image pickup plane 12a of the image pickup element 12 provided in the polarization imaging apparatus 4g, a monochrome image sensor 66, a wavelength-selection-filter array 73, and a polarizer-array device 49 are provided in this order.

Multiple recording of a plurality of wavelengths can be achieved without the wavelength-selection-filter array 73. However, the provision of the wavelength-selection-filter array 73 eliminates complexity of the calculation based on the spatial carrier phase shift method and thus decreases the problem of errors in calculations. With the polarizer-array device 49, the wavelength-selection-filter array 73, and the image sensor 66 arranged as described above, simultaneous recording of polarized-light distributions and spectral image information can be achieved. Then, by adjusting the inclination angles of the respective reference light beams as described previously, it is possible to obtain (four types of) pieces of spectral image information which is larger in number than types (2 types) of the filters 74a and 74b of the wavelength selection filter 73.

FIG. 38 is a view illustrating the flow for obtaining three-dimensional images corresponding to the varying combinations of polarizations and wavelengths from a hologram having been recorded by the image pickup element 12. First, the hologram having been recorded in the single-type image sensor 66 through the polarizer-array device 49 and the wavelength-selection-filter array 73 is separated into eight interference patterns corresponding to varying combinations of the polarization directions P1 and P2 and the wavelengths $\lambda_1$ through $\lambda_4$. Then, missing pixels in the interference patterns are interpolated. A direction in which missing pixels are interpolated is a direction in which pixels are not phase-shifted by a spatial carrier. For the interference patterns corresponding to the red light having the wavelength $\lambda_1$ and the green light having the wavelength $\lambda_2$, pixels are interpolated in the vertical direction. For the interference patterns corresponding to the blue light having the wavelength $\lambda_3$ and the infrared light having the wavelength $\lambda_4$, pixels are interpolated in the horizontal direction. Subsequently, not only spatial filtering but also a calculation based on a spatial carrier phase shift method are utilized to obtain complex amplitude distributions of the object corresponding to varying combinations of the specific polarization directions P1 and P2 and the specific wavelengths $\lambda_1$, $\lambda_2$, $\lambda_3$, and $\lambda_4$. Thereafter, three-dimensional images of the object corresponding to the varying combinations of the specific polarization directions P1 and P2 and the specific wavelengths $\lambda_1$, $\lambda_2$, $\lambda_3$, and $\lambda_4$ are reconstructed by diffraction integral.

FIG. 39 is a view illustrating the configuration of a multi-layered image sensor 75 according to Embodiment 6. FIG. 40 is an oblique view illustrating the configuration of an image pickup element 12 using the multilayered image sensor 75.

The following will describe a method for utilizing a spatial carrier phase shift method by means of a polarizer-array device 49 and the image sensor 75 having two types of light-receptive planes (sensors 76a and 76b) to obtain three-dimensional information, polarization information, and plural pieces of wavelength information.

The multilayered image sensor 75 has a sensor 76a and a sensor 76b. For example, the sensor 76a receives red light having a wavelength $\lambda_1$ and infrared light having a wavelength $\lambda_4$, and the sensor 76b receives green light having a wavelength $\lambda_2$ and blue light having a wavelength $\lambda_3$. When the red light, green light, and infrared light having respectively different wavelengths reach the multilayered image sensor 75 arranged as above, the sensor 76a receives the red light having the wavelength $\lambda_1$ and the infrared light having the wavelength $\lambda_4$, and the sensor 76b receives the green light having the wavelength $\lambda_2$ and the blue light having the wavelength $\lambda_3$.

By means of the multilayered image sensor 75 and the image pickup element 12 with the polarizer-array device 49, it is also possible to obtain three-dimensional information, polarization information, plural pieces of wavelength information. The configurations shown in FIGS. 39 and 40 are feasible in the polarization imaging apparatus 4g shown in (a)

of FIG. 37. For the processes before image reconstruction, the processes shown in FIG. 34 may be performed on light beams having varying wavelengths.

Embodiment 7

Embodiment 7 will describe embodiments of the present invention in cases where the number of polarization directions is larger than 2 (For example, the number of polarization directions is 3, 4, 5 or more, and Embodiment 7 will mainly describe a case where the number of polarization directions is 4.). FIG. 41 illustrates a configuration of a hologram formed by an image pickup section which is provided in a polarization imaging apparatus according to Embodiment 7. FIG. 41 illustrates a principle of an implementation method when the number of polarization directions is larger than 2. FIG. 41 illustrates, as an example, a principle of a method in a case where the number of polarization directions obtained by the image pickup element is 4 (polarization directions P1 through P4).

The hologram is subjected to 8-division multiplexing so that pieces of polarization information corresponding to respective polarizations in four directions are obtained. For example, as shown in FIG. 41, obtained by one image pickup is an interference figure formed in combination of: a hologram 56a of reference light having a polarization direction P1 and a phase 1; a hologram 56b of reference light having the polarization direction P1 and a phase 2; a hologram 56c of reference light having a polarization direction P2 and the phase 1; a hologram 56d of reference light having the polarization direction P2 and the phase 2; a hologram 56e of reference light having a polarization direction P3 and the phase 1; a hologram 56f of reference light having the polarization direction P3 and the phase 2; a hologram 56g of reference light having a polarization direction P4 and the phase 1; and a hologram 56h of reference light having the polarization direction P4 and the phase 2.

In this manner, the interference figure associated with 3 or more polarization directions is obtained by one image pickup, and an image reconstruction algorithm is applied to the interference figure thus obtained, so that three-dimensional information and polarized-light distribution information are obtained. Since the number of polarization directions is larger than 2, it becomes possible to obtain further more polarization information and to perform more detailed analysis of polarization states.

Note that in the above example, the number of polarization directions is 4. However, this is not intended to limit the present invention. Alternatively, the number of polarization directions may be 3 or 5.

FIG. 42 is a view schematically illustrating a configuration of a polarization imaging apparatus 1b according to Embodiment 7. Constituent components identical to the foregoing constituent components are given the same reference signs and detailed descriptions thereof are not repeated. As for the configuration of the polarization imaging apparatus 1b, a laser light source 11 may emit light including components corresponding to all of the polarization directions P1, P2, P3, and P4, or the laser light source 11 may emit light including components corresponding to only some of the polarization directions P1 through P4. An array of a polarizer-array device 55 is different from that of the polarizer-array device 23 shown in FIG. 1. Accordingly, an array of a phase-shift-array device 54 is varied depending upon the arrangement of polarizer-array device 55.

FIG. 43 is a view illustrating a configuration of constituent components of the polarization imaging apparatus 1b, wherein (a) is a view illustrating a configuration of the polarizer-array device 55, and (b) is a view illustrating a configuration of the phase-shift-array device 54. As shown in (a) of FIG. 43, each cell of the polarizer-array device 55 extracts information on one of the following four directions: a horizontal direction, a vertical direction, a rightward oblique direction at a 45-degree angle, and a leftward oblique direction at a 45-degree angle. By using the polarizer-array device 55, it is possible to obtain an interference figure associated with the four directions. In the above example, the four directions are provided. However, this is not intended to limit the present invention. Alternatively, an interference figure associated with polarizations in three or five directions can be extracted. By using the phase-shift-array device 54 shown in (b) of FIG. 43 in combination with the polarizer-array device 55, it is possible to obtain, by one image pickup, eight types of information on the hologram as shown in FIG. 41.

FIG. 44 illustrates an algorithm for the polarization imaging apparatus 1b generating a reconstructed image of polarized-light components. First, holograms 56a through 56h are extracted from a recorded interference figure in such a manner that the holograms 56a through 56h are grouped into the same types of holograms. Then, an interpolation process is performed to generate a plurality of interference figures corresponding to respective polarization directions P1 through P4. Next, signal processing of the interference figures thus generated is performed by utilizing a phase shift method or the like, so that complex amplitude distributions (amplitude distributions and phase distributions) of an object are obtained in correspondence with the polarization directions P1 through P4. Subsequently, a three-dimensional image of the object is obtained by diffraction calculation. Thus, instantaneous three-dimensional imaging of the object can be achieved in association with the polarization directions P1 through P4.

By using the complex amplitude distributions thus obtained, it is possible to carry out polarization imaging. Examples of a method for performing polarization imaging include: calculating polarized-light distributions of an object from amplitude distributions and phase distributions of the object with use of Stokes parameters, Jones vectors, or Mueller matrices; and using other expression(s) for calculating a polarization state.

As described above, by increasing polarization directions in number while lowering a spatial resolution, more amplitudes and phase information of polarization directions are obtained, so that more accurate polarization imaging can be thus achieved in a small three-dimensional space.

FIG. 45 is a view illustrating a configuration of holograms captured by an image pickup section that is provided in a polarization imaging apparatus 1c which is another polarization imaging apparatus according to Embodiment 7. Unlike Non-Patent Literature 1, the method using the spatial carrier phase shift method is such that single reference light having respective components of the different polarization directions P1 and P2 is made incident at an angle formed with respect to the object light. Since the light being made incident at a given angle is single reference light, the components of the polarization directions P1 and P2 enter from the same direction. Unlike Non-Patent Literature 1, a phase adjustment amount for the polarization direction P1 is therefore identical to that for the polarization direction P2. Consequently, the present method eliminates the need for a highly precise adjustment, which is required for Non-Patent Literature 1. This eliminates readily decreased accuracy in polarization imaging even when there occurs a change in position of optical element(s), unlike Non-Patent Literature 1.

FIG. 45 illustrates a principle of an implementation method through the practice of a spatial carrier phase shift method when the number of polarization directions is larger than 2. FIG. 45 illustrates, as an example, a principle of a method in a case where the number of polarization directions obtained by the image pickup element is 4 (polarization directions P1 through P4).

For example, as shown in FIG. 45, obtained by one image pickup is an interference figure which is formed in combination of: a hologram 58a of reference light having a polarization direction P1; a hologram 58b of reference light having a polarization direction P2; a hologram 58c of reference light having a polarization direction P3; a hologram 58d of reference light having a polarization direction P4.

In this manner, the interference figure associated with 3 or more polarization directions is obtained by one image pickup, and an image reconstruction algorithm is applied to the interference figure thus obtained, so that three-dimensional information and polarized-light distribution information are obtained. Since the number of polarization directions is larger than 2, it becomes possible to obtain further more polarization information and to perform more detailed analysis of polarization states.

Note that in the above example, the number of polarization directions is 4. However, this is not intended to limit the present invention. Alternatively, the number of polarization directions may be 3 or 5.

FIG. 46 is a view schematically illustrating another configuration of the polarization imaging apparatus 1c. Constituent components identical to the foregoing constituent components are given the same reference signs and detailed descriptions thereof are not repeated. As for the configuration of the polarization imaging apparatus 1c, a laser light source 11 may emit light including components corresponding to all of the polarization directions P1, P2, P3, and P4, or the laser light source 11 may emit light including components corresponding to only some of the polarization directions P1 through P4. Since the spatial carrier phase shift method is applied, an array of a polarizer-array device 57 is different from that of the polarizer-array device 23 shown in FIG. 1.

(a) of FIG. 47 is a view illustrating a configuration of the polarizer-array device 57 provided in the polarization imaging apparatus 1c. Each cell of the polarizer-array device 57 extracts information on one of the following four directions: a horizontal direction, a vertical direction, a rightward oblique direction at a 45-degree angle, and a leftward oblique direction at a 45-degree angle. By using the polarizer-array device 57, it is possible to obtain an interference figure associated with the four directions. In an example shown in (a) of FIG. 47, assume that 2×2 cells are one unit. Among the 2×2 cells, an upper-left cell extracts polarization information on the horizontal direction, a lower-right cell extracts polarization information on the vertical direction, an upper-right cell extracts polarization information on the rightward oblique direction at a 45-degree angle, and a lower-left cell extracts polarization information on the leftward oblique direction a 45-degree angle. In the above example, the four directions are provided. However, this is not intended to limit the present invention. Alternatively, an interference figure associated with polarizations in three or not less than five directions can be extracted.

(b) of FIG. 47 is a view illustrating the configuration of a hologram captured by an image pickup section 12 which is provided in the polarization imaging apparatus 1c. $\alpha 0$ through $\alpha 3$, each of which represents the amount of phase shift made by a spatial carrier, indicates an example of changes in amount of phase shift in relation to a horizontal direction. For example, $\alpha 0=0$, $\alpha 1=\pi/4$, $\alpha 2=\pi/2$, $\alpha 3=3\pi/4$ (all expressed in the unit (rad)). Alternately, the amount of phase shift may be changed in relation to the vertical direction.

By using the polarizer-array device 57 shown in (a) of FIG. 47, it is possible to obtain an interference figure associated with four directions, and by applying spatial carriers in the vertical direction, the horizontal direction, and other directions, it is possible to obtain holograms required for the phase shift method. As described above, it is possible to obtain, by one image pickup, information of (i) an interference figure required for the spatial carrier phase shift method shown in FIG. 35 and (ii) an interference figure associated with four directions.

FIG. 48 illustrates an algorithm for the polarization imaging apparatus generating a reconstructed image of polarized-light components. First, holograms 58a through 58d are extracted from a recorded interference figure in such a manner that the holograms 58a through 58d are grouped into the same types of holograms. Then, missing pixels are interpolated in a direction where no phase shift by spatial carriers occurs (vertical direction in an example shown in FIG. 48). Subsequently, by using pixels having their respective pixel values, calculation is carried out according to the spatial carrier phase shift method. This makes it possible to obtain complex amplitudes of an object from the pixels having their respective pixel values. Next, by using values of complex amplitude distributions thus obtained, missing pixels are subjected to an interpolation process for interpolation of values. In this manner, it is possible to obtain complex amplitude distributions (amplitude distributions and phase distributions) of the object corresponding to the polarization directions P1 and P4. Thereafter, a three-dimensional image of the object is obtained by diffraction calculation. Thus, instantaneous three-dimensional imaging of the object can be achieved in association with the polarization directions P1 through P4.

By using the complex amplitude distributions thus obtained, it is possible to carry out polarization imaging. Examples of a method for performing polarization imaging include: calculating polarized-light distributions of an object from amplitude distributions and phase distributions of the object with use of Stokes parameters, Jones vectors, or Mueller matrices; and using other expression(s) for calculating a polarization state.

As described above, by increasing polarization directions in number while lowering a spatial resolution, more amplitudes and phase information of polarization directions are obtained, so that more accurate polarization imaging can be thus achieved in a small three-dimensional space.

FIG. 49 illustrates a configuration of a hologram captured by an image pickup section which is provided in a polarization imaging apparatus 1d which is still another polarization imaging apparatus according to Embodiment 7. FIG. 49 illustrates a principle of an implementation method when the number of steps of phase shift in the polarization directions P1 and P2 is larger than 2. FIG. 49 illustrates, as an example, a principle of a method in a case where the number of steps of phase shift obtained by the image pickup element is 4.

Obtained by one image pickup is an interference figure formed in combination of: a hologram 61a of reference light having a polarization direction P1 and a phase 1; a hologram 61b of reference light having the polarization direction P1 and a phase 2; a hologram 61c of reference light having the polarization direction P1 and a phase 3; a hologram 61d of reference light having the polarization direction P1 and a phase 4; a hologram 61e of reference light having a polarization direction P2 and the phase 1; a hologram 61f of reference light having the polarization direction P2 and the phase 2; a hologram 61g of reference light having the polarization direction P2 and the phase 3; and a hologram 61h of reference light having the polarization direction P2 and the phase 4.

In this manner, the interference figure associated with 3 or more steps of phase shift is obtained by one image pickup, and an image reconstruction algorithm is applied to the interference figure thus obtained, so that three-dimensional information and polarized-light distribution information are obtained.

Note that in the above example, the number of steps of phase shift is 4. However, this is not intended to limit the present invention. Alternatively, the number of steps of phase shift may be 3 or 5.

FIG. 50 is a view schematically illustrating still another configuration of the polarization imaging apparatus 1d. Constituent components identical to the foregoing constituent components are given the same reference signs and detailed descriptions thereof are not repeated. A laser light source 11 emits light including components of both of the polarization directions P1 and P2. An array of a polarizer-array device 60 is different from that of the polarizer-array device 23 shown in FIG. 1. Further, an array of a phase-shift-array device 59 is different from that of the phase-shift-array device 21 shown in FIG. 1.

FIG. 51 is a view illustrating the configuration of constituent components of the polarization imaging apparatus 1d, wherein (a) is a view illustrating a configuration of the polarizer-array device 60, and (b) is a view illustrating the configuration of the phase-shift-array device 59. As shown in (a) of FIG. 51, the polarizer-array device 60 has 2×4 cells as one unit, and each cell extracts information on one of the following directions: a horizontal direction and a vertical direction. As shown in (b) of FIG. 51, the phase-shift-array device 59 has 2×2 cells as one unit, and each unit of the 2×2 cells performs phase shift into 4 levels of phases ph0 to ph3. In the above example, the number of steps of phase shift is 4. However, this is not intended to limit the present invention. Alternatively, the number of steps of phase shift may be 3, 5, or more. By using the polarizer-array device 60 shown in (a) of FIG. 51 in combination with the phase-shift-array device 59 shown in (b) of FIG. 51, it is possible to obtain, by one image pickup, eight types of information on the interference figure as shown in FIG. 49.

FIG. 52 illustrates an algorithm for the polarization imaging apparatus 1d generating a reconstructed image of polarized-light components. First, holograms 61a through 61h are extracted from a recorded interference figure in such a manner that the holograms 61a through 61h are grouped into the same types of holograms. Then, an interpolation process is performed to generate a plurality of interference figures corresponding to polarization directions P1 and P2. Next, signal processing of the interference figures thus generated is performed by utilizing a phase shift method or the like method, so that complex amplitude distributions (amplitude distributions and phase distributions) of an object are obtained in correspondence with the polarization directions P1 and P2. Subsequently, a three-dimensional image of the object is obtained by diffraction calculation. Thus, instantaneous three-dimensional imaging of the object can be achieved in association with the polarization directions P1 and P2.

By using the complex amplitude distributions thus obtained, it is possible to carry out polarization imaging. Examples of a method for carrying out polarization imaging include: calculating polarized-light distributions of an object from amplitude distributions and phase distributions of the object with use of Stokes parameters, Jones vectors, or Mueller matrices; and using other expression(s) for calculating a polarization state.

As described above, the increase in number of steps of phase shift while lowering a spatial resolution eliminates the need for pre-implementation or post-implementation measurement of reference light intensity and increases intensity of object light. This eliminates constraints such as regular adjustments required for Non-Patent Literature 1. Thus, the above arrangement is useful though it involves an increased number of steps of phase shift and a correspondingly small measurement range.

Preferred Embodiments of the Present Invention

Further, in the polarization imaging apparatus of the present invention, it is preferable that: the reference light further includes a third polarized-light component polarized in a third direction and a fourth polarized-light component polarized in a fourth direction; the interference pattern further includes (v) a fifth interference figure formed by interference between the object light and the reference light which has the third polarized-light component and the first phase, (vi) a sixth interference figure formed by interference between the object light and the reference light which has the third polarized-light component and the second phase, (vii) a seventh interference figure formed by interference between the object light and the reference light which has the fourth polarized-light component and the first phase, and (viii) an eighth interference figure formed by interference between the object light and the reference light which has the fourth polarized-light component and the second phase; the reconstructed-image-producing section (III) produces a third reconstructed image of the object in regard to a third polarized-light component which is polarized in the third direction, after (a) extraction of pixels corresponding to the fifth interference figure and the sixth interference figure from the interference pattern and (b) pixel interpolation and (IV) produces a fourth reconstructed image of the object in regard to a fourth polarized-light component which is polarized in the fourth direction, after (a) extraction of pixels corresponding to the seventh interference figure and the eighth interference figure from the interference pattern and (b) pixel interpolation; and the polarized-light-image-calculating section obtains the polarized-light images of the object from the first to fourth reconstructed images, the polarized-light images corresponding to respective positions in each of the reconstructed images of the object.

In the polarization imaging apparatus of the present invention, it is preferable that: the interference pattern further includes (v) a fifth interference figure formed by interference between the object light and the reference light which has the first polarized-light component and a third phase, (vi) a sixth interference figure formed by interference between the object light and the reference light which has the first polarized-light component and a fourth phase, (vii) a seventh interference figure formed by interference between the object light and the reference light which has the second polarized-light component and the third phase, and (viii) an eighth interference figure formed by interference between the object light and the reference light which has the second polarized-light component and the fourth phase; the reconstructed-image-producing section (III) produces a third reconstructed image of the object in regard to the first polarized-light component, after (a) extraction of pixels corresponding to the first interference figure, the second interference figure, the fifth interference figure and the sixth interference figure from the interference pattern and (b) pixel interpolation and (IV) produces a fourth reconstructed image of the object in regard to the second polarized-light component, after extraction of pixels corresponding to the third interference figure, the fourth interference figure, the seventh interference figure and the eighth interference figure from the interference pattern and (b) pixel interpolation; and the polarized-light-image-calculating section obtains the polarized-light images of the object from the third and fourth reconstructed images, the polarized-light images corresponding to respective positions in each of the reconstructed images of the object.

In the polarization imaging apparatus of the present invention, it is preferable that the light source is made of three light sources supplying light of three wavelength types, or four light sources supplying light of four wavelength types.

The polarization imaging apparatus of the present invention may be configured to further include: a polarization-direction-changing-array section including (a) first-direction regions converting the reference light having entered the first-direction regions into reference light polarized in the first direction and (b) second-direction regions converting the reference light having entered the second-direction regions into reference light polarized in the second direction; and a phase-shift-array section including first phase-shift regions and second phase-shift regions, and making (a) a phase of the reference light having entered the first phase-shift regions different from (b) a phase of the reference light having entered the second phase-shift regions.

The polarization imaging apparatus may be configured to further include: a phase-shift-array section including first phase-shift regions and second phase-shift regions, and making (a) a phase of the reference light having entered the phase-shift regions different from (b) a phase of the reference light having entered the second phase-shift regions; and a polarizer-array section which the reference light and the object light enter, the polarizer-array section including (a) first polarizer regions allowing the first polarized-light components of the reference light and the object light to exit from the first polarizer regions, and (b) second polarizer regions allowing the second polarized-light components of the reference light and the object light to exit from the second polarizer regions.

In the above configuration, it is possible to simultaneously form, on one plane, four types of interference figures in regard to different phases of the reference light and different polarization directions. By capturing images of the four types of interference figures by an image pickup element, the four types of interference figures can be simultaneously obtained.

In the polarization imaging apparatus of the present invention, the reference light may enter the image pickup section, being inclined, with respect to the object light, at an inclination angle set in accordance with a wavelength of the reference light and a distance between pixels in the image pickup section.

Further, the reference light may enter the image pickup section, being inclined, with respect to the object light, at an inclination angle obtained by: $\sin^{-1}(\lambda/4T)$ where the wavelength of the reference light is $\lambda$ and the distance between pixels of the image pickup section is $\tau$.

In the above configuration, instantaneous three-dimensional imaging for a wide area can be realized by using only a compact optical system and simple image processing, while no spatial phase shift element is required.

The polarization imaging apparatus may further include a spatial-carrier-phase-shifting region obtaining complex amplitude distributions of the object from a hologram of regions that are adjacent to each other along an inclination direction of the reference light.

In the above configuration, instantaneous three-dimensional imaging for a wide area can be realized by a simple algorithm.

The polarization imaging apparatus may be configured to further include: a polarizer-array section which the reference light and the object light enter, the polarizer-array section including (a) first polarizer regions allowing the first polarized-light components of the reference light and the object light to exit from the first polarizer regions, and (b) second polarizer regions allowing the second polarized-light components of the reference light and the object light to exit from the second polarizer regions; and an optical-path-length-shift-array section which the reference light and the object light enter, the optical-path-length-shift-array section including first optical-path-length-shifting regions and second optical-path-length-shifting regions, the polarizer-array section and the optical-path-length-shift-array section being provided between the object and the image pickup section, the optical-path-length-shift-array section (i) making (a) a phase of the reference light having entered the first-optical-path-length-shift regions different from (b) a phase of the reference light having entered the second-optical-path-length-shift regions, and also (ii) making (a) a phase of the object light having entered the first-optical-path-length-shift regions different from (b) a phase of the object light having entered the second-optical-path-length-shift regions.

In the above configuration, it is possible to simultaneously form, on one plane, four types of interference figures in regard to different optical path lengths from an object and different polarization directions. By capturing images of the four types of interference figures by an image pickup element, the four types of interference figures can be simultaneously obtained.

The polarization imaging apparatus may be configured such that: the reconstructed-image-producing section obtains (a) a first phase distribution of the object in regard to the first polarized-light component, from the first interference figure and the second interference figure associated with the first polarized-light components and (b) a second phase distribution of the object in regard to the second polarized-light component, from the third interference figure and the fourth interference figure associated with the second polarized-light components; and the polarized-light-image-calculating section obtains polarization states at respective positions in each of the reconstructed images of the object from the first and second phase distributions and the first and second reconstructed images.

In the above configuration, it is possible to obtain a detailed polarization state by calculating, for example, Stokes parameters, from the first and second reconstructed images and the first and second phase distributions of the object.

The polarization imaging apparatus may further include: a magnifying optical section for magnifying an image of the object, the magnifying optical section being provided between the object and the image pickup section; and a wave-front-transforming section for converting the reference light to a spherical or aspherical wave so that the reference light enters the image pickup section as a spherical or aspherical wave.

In the above configuration, the reference light is a spherical or aspherical wave. Accordingly, a difference in angle between the reference light and the object light can be made small when the reference light and the object light enter the image pickup section. This increases a distance between interference fringes. This makes it possible to perform image capturing without missing detailed information of an object present at interference fringes. Therefore, it becomes possible to accurately reproduce and observe detailed information of an object image that is magnified by the magnifying optical section.

The polarization imaging apparatus may be configured to further include: a plurality of light sources each being the light source supplying the reference light and the object light; and a wavelength selection filter, wherein: the plurality of light sources each supply reference light of a different wavelength and object light of a different wavelength; and the wavelength selection filter includes wavelength-selecting regions each transmitting light of a different wavelength, and each of the wavelength-selecting regions selectively transmits the reference light and the object light depending on wavelengths.

The above configuration makes it possible to obtain plural interference figures in regard to (i) different polarization directions, (ii) different phases of the reference light or different optical path lengths from an object, and (iii) different wavelengths. Accordingly, a reconstructed image and a polarization state can be obtained for each wavelength. Therefore, the above configuration makes it possible to simultaneously perform spectral imaging and polarization imaging.

Further, the first direction may be orthogonal to the second direction.

The above configuration makes it possible to obtain more accurate polarization state.

The present invention can be restated as follows.

A polarization imaging apparatus includes: a light source supplying reference light and object light; an image pickup section capturing images of interference figures each formed from the reference light and the object light that reaches the image pickup section through an object; a reconstructing section producing reconstructed images; and a polarization-state-calculating section obtaining polarization states, wherein: the object light and the reference light each include a first polarized-light component polarized in a first direction and a second polarized-light component polarized in a second direction that is different from the first direction, both of which object light and reference light enter the image pickup section; the image pickup section simultaneously captures four types of interference images in total including (i) two types of interference figures each formed by interference between the object light and the reference light with one of two different phases, in regard to the first polarized-light component, and (ii) two types of interference figures each formed by interference between the object light and the reference light with one of the two different phases, in regard to the second polarized-light component; the reconstructing section (I) produces a first reconstructed image of the object in regard to the first polarized-light component, from the two types of interference figures in regard to the first polarized-light component and (II) produces a second reconstructed image of the object in regard to the second polarized-light component, from the two types of interference figures in regard to the second polarized-light component; and the polarization-state-calculating section obtains the polarization states from the first reconstructed image and the second reconstructed image, the polarized-light images corresponding to respective positions in each of the reconstructed images of the object.

The present invention is not limited to the description of the embodiments above, but may be altered by a skilled person within the scope of the claims. An embodiment based on a proper combination of technical means disclosed in different embodiments is encompassed in the technical scope of the present invention.

INDUSTRIAL APPLICABILITY

The present invention is applicable to a polarization imaging apparatus. The present invention makes it possible to observe in real time various polarized-light images of, for example, (a) distortion of glass in production which glass is used for (i) windows for building structures such as buildings and general houses, (ii) thin displays, or the like, (b) distortion in molding and coating of car bodies of automobiles, (c) distortion in silicon wafers, (d) distortion in disks of extra-high-density disk memories, and the like. Further, the present invention is applicable to microscopes. The present invention makes it possible to observe polymers (proteins) constituting living bodies. Accordingly, it becomes possible to observe pathological tissues of cancer cells or the like by using polarized-light images. In addition, the present invention is applicable to endoscopic images. This makes it possible to obtain new information on different tissues, from polarized light information.

REFERENCE SIGNS LIST 1, 2, 3, 4, 5 polarization imaging apparatus
11 laser light source (light source)
12 image pickup element (image pickup section)
12a image pickup plane
13 computer
14 beam expander
15 collimator lens
16 beam splitter
17, 20, 44 mirror
18 object
19, 45, 46 beam-combining element
21, 47 phase-shift-array device (phase-shift-array section)
21a, 21b, 38a, 38b, 47a to 47f phase-shift region
22 image-forming optical section
23, 49 polarizer-array device (polarizer-array section)
23a, 23b, 49a, 49b polarizer (polarizer region)
24 reconstructing section (reconstructed-image-producing section)
25 polarization-state-calculating section (polarized-light-image-calculating section)
26, 28a to 28d, 29a to 29d, 50 interference pattern
27a to 27d, 31a, 31b, 51a to 511 pixel
30, 32a, 32b, 33a, 33b intensity distribution of reference light
34a, 34b complex amplitude distribution
35 polarized-light-image-generating section
36 ½ wave plate
37 first spatial light modulator (polarization-direction-changing-array section)
37a first-direction region
37b second-direction region
38, 40 second spatial light modulator (phase-shift-array section)
39a, 39b region
41 image-forming optical section (wavefront-transforming section)
42 spatial-filtering element
43 microscope objective lens (magnifying optical section)
48 wavelength selection filter
48a, 48b, 48c wavelength-selecting region
52 optical-path-length-shift-array device (optical-path-length-shift-array section)
52a, 52b optical-path-length-shifting region
53 spatial-carrier-phase-shifting region
54, 59 phase-shift-array device (phase-shift-array section)
55, 57, 60 polarizer-array device (polarizer-array section)

| Reference Signs List | |
|---|---|
| 1, 2, 3, 4, 5 | polarization imaging apparatus |
| 11 | laser light source (light source) |
| 12 | image pickup element (image pickup section) |
| 12a | image pickup plane |
| 13 | computer |
| 14 | beam expander |
| 15 | collimator lens |
| 16 | beam splitter |
| 17, 20, 44 | mirror |
| 18 | object |
| 19, 45, 46 | beam-combining element |
| 21, 47 | phase-shift-array device (phase-shift-array section) |
| 21a, 21b, 38a, 38b, 47a to 47f | phase-shift region |
| 22 | image-forming optical section |
| 23, 49 | polarizer-array device (polarizer-array section) |
| 23a, 23b, 49a, 49b | polarizer (polarizer region) |
| 24 | reconstructing section (reconstructed-image-producing section) |
| 25 | polarization-state-calculating section (polarized-light-image-calculating section) |
| 26, 28a to 28d, 29a to 29d, 50 | interference pattern |
| 27a to 27d, 31a, 31b, 51a to 51l | pixel |
| 30, 32a, 32b, 33a, 33b | intensity distribution of reference light |
| 34a, 34b | complex amplitude distribution |
| 35 | polarized-light-image-generating section |
| 36 | ½ wave plate |
| 37 | first spatial light modulator (polarization-direction-changing-arraysection) |
| 37a | first-direction region |
| 37b | second-direction region |
| 38, 40 | second spatial light modulator (phase-shift-array section) |
| 39a, 39b | region |
| 41 | image-forming optical section (wavefront-transforming section) |
| 42 | spatial-filtering element |
| 43 | microscope objective lens (magnifying optical section) |
| 48 | wavelength selection filter |
| 48a, 48b, 48c | wavelength-selecting region |
| 52 | optical-path-length-shift-array device (optical-path-length-shift-array section) |
| 52a, 52b | optical-path-length-shifting region |
| 53 | spatial-carrier-phase-shifting region |
| 54, 59 | phase-shift-array device (phase-shift-array section) |
| 55, 57, 60 | polarizer-array device (polarizer-array section) |
| 56a to 56h | hologram |
| 58a to 58d | hologram |
| 61 | hologram |

The invention claimed is:

1. An in-line type polarization imaging apparatus comprising:

at least one light source for supplying light including reference light and object light;

an image pickup section capturing images of interference figures each formed from the reference light and the object light that reaches the image pickup section through an object;

a reconstructed-image-producing section producing reconstructed images;

a polarized-light-image-calculating section obtaining polarized-light images;

a beam splitter splitting the light supplied from the light source into the reference light and the object light;

a phase-shift-array section including first phase-shift regions and second phase-shift regions, and making (a) a phase of the reference light having entered the first phase-shift regions different from (b) a phase of the reference light having entered the second phase-shift regions, the reference light being a divisional portion of the light split by the beam splitter; and a beam-combining element combining the object light with the reference light having passed through the phase-shift-array section, the object light reaching after having passed through the object, wherein:

the object light and the reference light each include a first polarized-light component polarized in a first direction and a second polarized-light component polarized in a second direction that is different from the first direction, both of which object light and reference light enter the image pickup section;

the image pickup section simultaneously captures an image of an interference pattern including (i) a first interference figure formed by interference between the object light which has the first polarized-light component and the reference light which has the first polarized-light component and a first phase, (ii) a second interference figure folioed by interference between the object light which has the first polarized-light component and the reference light which has the first polarized-light component and a second phase, (iii) a third interference figure formed by interference between the object light which has the second polarized-light component and the reference light which has the second polarized-light component and the first phase, and (iv) a fourth interference figure formed by interference between the object light which has the second light component and the reference light which has the second polarized-light component and the second phase;

the reconstructed-image-producing section (I) produces a first reconstructed image of the object in regard to the first polarized-light component, the first reconstructed image corresponding to the first interference figure and the second interference figure, after (a) extraction of pixels corresponding to the first interference figure and the second interference figure from the interference pattern and (b) pixel interpolation and (II) produces a second reconstructed image of the object in regard to the second polarized-light component, the second reconstructed image corresponding to the third interference figure and the fourth interference figure, after (a) extraction of pixels corresponding to the third interference figure and the fourth interference figure from the interference pattern and (b) pixel interpolation; and the polarized-light-image-calculating section obtains the polarized-light images from the first reconstructed image and the second reconstructed image, the polarized-light images corresponding to respective positions in each of the reconstructed images of the object, wherein the reconstructed-image-producing section (i) obtains two respective intensity distributions of the first polarized-light component and the second polarized-light component of only the reference light, (ii) calculates respective complex amplitude distributions of the first polarized-light component and the second polarized-light component from the first to fourth interference figures and the two intensity distributions of only the reference light, and (iii) obtains a first amplitude distribution and a first phase distribution each as the first reconstructed image in regard to the first polarized-light component and a second amplitude distribution and a second phase distribution each as the second reconstructed image in regard to the second polarized-light component, from the complex amplitude distributions, wherein the polarized-light-image-calculating section obtains the polarized-light images corresponding to respective positions in each of the reconstructed images of the object, from the first amplitude distribution and the first phase distribution of the object and the second amplitude distribution and the second phase distribution of the object.

2. The polarization imaging apparatus as set forth in claim 1, wherein:

the object light and the reference light each further include a third polarized-light component polarized in a third direction and a fourth polarized-light component polarized in a fourth direction;

the interference pattern further includes (v) a fifth interference figure formed by interference between the object light which has the third polarized-light component and the reference light which has the third polarized-light component and the first phase, (vi) a sixth interference figure formed by interference between the object light which has the third polarized-light component and the reference light which has the third polarized-light component and the second phase, (vii) a seventh interference figure formed by interference between the object light which has the fourth polarized-light component and the reference light which has the fourth polarized-light component and the first phase, and (viii) an eighth interference figure formed by interference between the object light which has the fourth polarized-light component and the reference light which has the fourth polarized-light component and the second phase;

the reconstructed-image-producing section (III) produces a third reconstructed image of the object in regard to the third polarized-light component, after (a) extraction of pixels corresponding to the fifth interference figure and the sixth interference figure from the interference pattern and (b) pixel interpolation and (IV) produces a fourth reconstructed image of the object in regard to the fourth polarized-light component, after (a) extraction of pixels corresponding to the seventh interference figure and the eighth interference figure from the interference pattern and (b) pixel interpolation; and the polarized-light-image-calculating section obtains the polarized-light images of the object from the first to fourth reconstructed images, the polarized-light images corresponding to respective positions in each of the reconstructed images of the object.

3. The polarization imaging apparatus as set forth in claim 1, wherein:

the interference pattern further includes (v) a fifth interference figure formed by interference between the object light which has the first polarized-light component and the reference light which has the first polarized-light component and a third phase, (vi) a sixth interference figure formed by interference between the object light which has the first polarized-light component and the reference light which has the first polarized-light component and a fourth phase, (vii) a seventh interference figure formed by interference between the object light which has the second polarized-light component and the reference light which has the second polarized-light component and the third phase, and (viii) an eighth interference figure formed by interference between the object light which has the second polarized-light component and the reference light which has the second polarized-light component and the fourth phase;

the reconstructed-image-producing section (III) produces a third reconstructed image of the object in regard to the first polarized-light component, after (a) extraction of pixels corresponding to the first interference figure, the second interference figure, the fifth interference figure and the sixth interference figure from the interference pattern and (b) pixel interpolation and (IV) produces a fourth reconstructed image of the object in regard to the second polarized-light component, after extraction of pixels corresponding to the third interference figure, the fourth interference figure, the seventh interference figure and the eighth interference figure from the interference pattern and (b) pixel interpolation; and the polarized-light-image-calculating section obtains the polarized-light images of the object from the third and fourth reconstructed images, the polarized-light images corresponding to respective positions in each of the reconstructed images of the object.

4. The polarization imaging apparatus as set forth in claim 1, wherein the light source is made of (a) two light sources supplying light of two wavelength types, (b) three light sources supplying light of three wavelength types, or (c) four light sources supplying light of four wavelength types.

5. The polarization imaging apparatus as set forth in claim 1, further comprising a polarization-direction-changing-array section including (a) first-direction regions converting the reference light having entered the first-direction regions into reference light polarized in the first direction and (b) second-direction regions converting the reference light having entered the second-direction regions into reference light polarized in the second direction.

6. The polarization imaging apparatus as set forth in claim 1, further comprising a polarizer-array section which the reference light and the object light enter, the polarizer-array section including (a) first polarizer regions allowing the first polarized-light components of the reference light and the object light to exit from the first polarizer regions, and (b) second polarizer regions allowing the second polarized-light components of the reference light and the object light to exit from the second polarizer regions.

7. The polarization imaging apparatus as set forth in claim 1, wherein:

the reconstructed-image-producing section obtains (a) a first phase distribution of the object in regard to the first polarized-light component, from the first interference figure and the second interference figure associated with the first polarized-light components and (b) the second amplitude distribution and a second phase distribution of the object in regard to the second polarized-light component, from the third interference figure and the fourth interference figure associated with the second polarized-light components; and the polarized-light-image-calculating section obtains polarization states at respective positions in each of the reconstructed images of the object from the first and second phase distributions and the first and second amplitude distributions.

8. The polarization imaging apparatus as set forth in claim 1 further comprising:

a magnifying optical section for magnifying an image of the object, the magnifying optical section being provided between the object and the image pickup section; and a wavefront-transforming section for converting the reference light to a spherical or aspherical wave so that the reference light enters the image pickup section as a spherical or aspherical wave.

9. The polarization imaging apparatus as set forth in claim 1, further comprising:
a plurality of light sources each being the light source supplying the reference light and the object light; and a wavelength selection filter, wherein:
the plurality of light sources each supply reference light of a different wavelength and object light of a different wavelength; and
the wavelength selection filter includes wavelength-selecting regions each transmitting light of a different wavelength, and each of the wavelength-selecting regions selectively transmits the reference light and the object light depending on wavelengths.

10. The polarization imaging apparatus as set forth in claim 1, wherein the first direction is orthogonal to the second direction.

11. An in-line type polarization imaging apparatus comprising:
a light source for supplying reference light and object light;
an image pickup section capturing images of interference figures each formed from the reference light and the object light that reaches the image pickup section through an object;
a reconstructed-image-producing section producing reconstructed images; and
a polarized-light-image-calculating section obtaining polarized-light images, wherein:
the light source supplies light of at least one wavelength type;
the object light and the reference light each include a first polarized-light component polarized in a first direction and a second polarized-light component polarized in a second direction that is different from the first direction, both of which object light and reference light enter the image pickup section;
the image pickup section simultaneously captures an image of an interference pattern including (i) a first interference figure formed by interference between the object light which has the first polarized-light component and a first optical path length and the reference light which has the first polarized-light component and the first optical path length, (ii) a second interference figure formed by interference between the object light which has the first polarized-light component and a second optical path length and the reference light which has the first polarized-light component and the second optical path length, (iii) a third interference figure formed by interference between the object light which has the second polarized-light component and the first optical path length and the reference light which has the second polarized-light component and the first optical path length, and (iv) a fourth interference figure formed by interference between the object light which has the second polarized-light component and the second optical path length and the reference light which has the second polarized-light component and the second optical path length;
the reconstructed-image-producing section (I) produces a first reconstructed image of the object in regard to the first polarized-light component, the first reconstructed image corresponding to the first interference figure and the second interference figure, after (a) extraction of pixels corresponding to the first interference figure and the second interference figure from the interference pattern and (b) pixel interpolation and (II) produces a second reconstructed image of the object in regard to the second polarized-light component, the second reconstructed image corresponding to the third interference figure and the fourth interference figure, after (a) extraction of pixels corresponding to the third interference figure and the fourth interference figure from the interference pattern and (b) pixel interpolation; and
the polarized-light-image-calculating section obtains the polarized-light images from the first reconstructed image and the second reconstructed image, the polarized-light images corresponding to respective positions in each of the reconstructed images of the object,
wherein the reconstructed-image-producing section (i) obtains two respective intensity distributions of the first polarized-light component and the second polarized-light component of only the reference light, (ii) calculates respective complex amplitude distributions of the first polarized-light component and the second polarized-light component from the first to fourth interference figures and the two intensity distributions of only the reference light, and (iii) obtains a first amplitude distribution and a first phase distribution each as the first reconstructed image in regard to the first polarized-light component and a second amplitude distribution and a second phase distribution each as the second reconstructed image in regard to the second polarized-light component, from the complex amplitude distributions,
wherein the polarized-light-image-calculating section obtains the polarized-light images corresponding to respective positions in each of the reconstructed images of the object, from the first amplitude distribution and the first phase distribution of the object and the second amplitude distribution and the second phase distribution of the object.

12. The polarization imaging apparatus as set forth in claim 11, further comprising:
a polarizer-array section which the reference light and the object light enter, the polarizer-array section including (a) first polarizer regions allowing the first polarized-light components of the reference light and the object light to exit from the first polarizer regions, and (b) second polarizer regions allowing the second polarized-light components of the reference light and the object light to exit from the second polarizer regions; and
an optical-path-length-shift-array section which the reference light and the object light enter, the optical-path-length-shift-array section including first optical-path-length-shifting regions and second optical-path-length-shifting regions,
the polarizer-array section and the optical-path-length-shift-array section being provided between the object and the image pickup section,
the optical-path-length-shift-array section (i) making (a) a phase of the reference light having entered the first-optical-path-length-shift regions different from (b) a phase of the reference light having entered the second-optical-path-length-shift regions, and also (ii) making (a) a phase of the object light having entered the first-optical-path-length-shift regions different from (b) a phase of the object light having entered the second-optical-path-length-shift regions.

13. The polarization imaging apparatus as set forth in claim 11, wherein:
the reconstructed-image-producing section obtains (a) a first phase distribution of the object in regard to the first polarized-light component, from the first interference figure and the second interference figure associated with the first polarized-light components and (b) the second amplitude distribution and a second phase distribution of the object in regard to the second polarized-light component, from the third interference figure and the fourth interference figure associated with the second polarized-light components; and the polarized-light-image-calculating section obtains polarization states at respective positions in each of the reconstructed images of the object from the first and second phase distributions and the first and second amplitude distributions.

14. The polarization imaging apparatus as set forth in claim 11 further comprising:

a magnifying optical section for magnifying an image of the object, the magnifying optical section being provided between the object and the image pickup section; and a wavefront-transforming section for converting the reference light to a spherical or aspherical wave so that the reference light enters the image pickup section as a spherical or aspherical wave.

15. The polarization imaging apparatus as set forth in claim 11, further comprising:

a plurality of light sources each being the light source supplying the reference light and the object light; and a wavelength selection filter, wherein:

the plurality of light sources each supply reference light of a different wavelength and object light of a different wavelength; and the wavelength selection filter includes wavelength-selecting regions each transmitting light of a different wavelength, and each of the wavelength-selecting regions selectively transmits the reference light and the object light depending on wavelengths.

16. The polarization imaging apparatus as set forth in claim 11, wherein the first direction is orthogonal to the second direction.

17. A method for polarization imaging in which a polarization state of object light is obtained by capturing images of interference figures each formed by reference light and the object light that reaches through an object, the method comprising the steps of:

(A) splitting light supplied from a light source into the reference light and the object light each including a first polarized-light component polarized in a first direction and a second polarized-light component polarized in a second direction that is different from the first direction;

(B) making (a) a phase of the reference light having entered the first phase-shift regions different from (b) a phase of the reference light having entered the second phase-shift regions, by use of a phase-shift-array section including first phase-shift regions and second phase-shift regions;

(C) combining the object light with the reference light having different phases, the object light reaching after having passed through the object;

(D) capturing, simultaneously, an image of an interference pattern including first to fourth interference figures formed from the object light and the reference light, the first interference figure being formed by interference between the object light which has the first polarized-light component and the reference light which has the first polarized-light component and a first phase, the second interference figure being formed by interference between the object light which has the first polarized-light component and the reference light which has the first polarized-light component and a second phase, the third interference figure being formed by interference between the object light which has the second polarized-light component and the reference light which has the second polarized-light component and the first phase, and the fourth interference figure being formed by interference between the object light which has the second polarized-light component and the reference light which has the second polarized-light component and the second phase;

(E) producing (I) a first reconstructed image of the object in regard to the first polarized-light component, the first reconstructed image corresponding to the first interference figure and the second interference figure, after (a) extraction of pixels corresponding to the first interference figure and the second interference figure from the interference pattern and (b) pixel interpolation and (II) a second reconstructed image of the object in regard to the second polarized-light component, the second reconstructed image corresponding to the third interference figure and the fourth interference figure, after (a) extraction of pixels corresponding to the third interference figure and the fourth interference figure from the interference pattern and (b) pixel interpolation; and (F) obtaining polarized-light images from the first reconstructed image and the second reconstructed image, the polarized-light images corresponding to respective positions in each of the reconstructed images of the object, the step (E) including the sub-steps of:

obtaining two respective intensity distributions of the first polarized-light component and the second polarized-light component of only the reference light;

calculating respective complex amplitude distributions of the first polarized-light component and the second polarized-light component from the first to fourth interference figures and the two intensity distributions of only the reference light; and obtaining a first amplitude distribution and a first phase distribution each as the first reconstructed image in regard to the first polarized-light component and a second amplitude distribution and a second phase distribution each as the second reconstructed image in regard to the second polarized-light component, from the complex amplitude distributions, the step (F) including the sub-step of obtaining the polarized-light images corresponding to respective positions in each of the reconstructed images of the object, from the first amplitude distribution and the first phase distribution of the object and the second amplitude distribution and the second phase distribution of the object.

18. A method for polarization imaging in which a polarization state of object light is obtained by capturing images of interference figures each formed by reference light and the object light that reaches through an object, the method comprising the steps of:

(A) capturing, simultaneously, an image of an interference pattern including first to fourth interference figures formed from the object light and the reference light, the object light and the reference light each including a first polarized-light component polarized in a first direction and a second polarized-light component polarized in a second direction that is different from the first direction, the first interference figure being formed by interference between the object light which has the first polarized-light component and a first optical path length and the reference light which has the first polarized-light component and the first optical path length, the second interference figure being formed by interference between the object light which has the first polarized-light component and a second optical path length and the reference light which has the first polarized-light component and the second optical path length, the third interference figure being formed by interference between the object light which has the second polarized-light component and the first optical path length and the reference light which has the second polarized-light component and the first optical path length, and the fourth interference figure being formed by interference between the object light which has the second polarized-light component and the second optical path length and the reference light which has the second polarized-light component and the second optical path length;

(B) producing (I) a first reconstructed image of the object in regard to the first polarized-light component, the first reconstructed image corresponding to the first interference figure and the second interference figure, after (a) extraction of pixels corresponding to the first interference figure and the second interference figure from the interference pattern and (b) pixel interpolation and (II) a second reconstructed image of the object in regard to the second polarized-light component, the second reconstructed image corresponding to the third interference figure and the fourth interference figure, after (a) extraction of pixels corresponding to the third interference figure and the fourth interference figure from the interference pattern and (b) pixel interpolation; and (C) obtaining a polarization state from the first reconstructed image and the second reconstructed image, the polarization state corresponding to each position in each of the reconstructed images of the object, the step (B) including the sub-steps of:

obtaining two respective intensity distributions of the first polarized-light component and the second polarized-light component of only the reference light;

calculating respective complex amplitude distributions of the first polarized-light component and the second polarized-light component from the first to fourth interference figures and the two intensity distributions of only the reference light; and obtaining a first amplitude distribution and a first phase distribution each as the first reconstructed image in regard to the first polarized-light component and a second amplitude distribution and a second phase distribution each as the second reconstructed image in regard to the second polarized-light component, from the complex amplitude distributions, the step (C) including the sub-step of obtaining the polarization state corresponding to each position in each of the reconstructed images of the object, from the first amplitude distribution and the first phase distribution of the object and the second amplitude distribution and the second phase distribution of the object.

19. An in-line type polarization imaging apparatus comprising:

at least one light source for supplying light including reference light and object light;

an image pickup section capturing images of interference figures each formed from the reference light and the object light that reaches the image pickup section through an object;

a reconstructed-image-producing section producing reconstructed images;

a polarized-light-image-calculating section obtaining polarized-light images;

a beam splitter splitting the light supplied from the light source into the reference light and the object light;

inclination means for inclining the reference light at an inclination angle based on a wavelength of the reference light and a distance between pixels of the image pickup section, the reference light being a divisional portion of the light split by the beam splitter; and a beam-combining element combining the object light with the reference light having been inclined by the inclination means, the object light reaching after having passed through the object, wherein:

the reference light enters the image pickup section, being inclined at the inclination angle relative to the object light;

the object light and the reference light each include a first polarized-light component polarized in a first direction and a second polarized-light component polarized in a second direction that is different from the first direction, both of which object light and reference light enter the image pickup section;

the image pickup section simultaneously captures an image of an interference pattern including (i) a first interference figure formed by interference between the object light which has the first polarized-light component and the reference light which has the first polarized-light component and a first phase, (ii) a second interference figure formed by interference between the object light which has the first polarized-light component and the reference light which has the first polarized-light component and a second phase, (iii) a third interference figure formed by interference between the object light which has the second polarized-light component and the reference light which has the second polarized-light component and the first phase, and (iv) a fourth interference figure formed by interference between the object light which has the second light component and the reference light which has the second polarized-light component and the second phase;

the reconstructed-image-producing section (I) produces a first reconstructed image of the object in regard to the first polarized-light component, the first reconstructed image corresponding to the first interference figure and the second interference figure, after (a) extraction of pixels corresponding to the first interference figure and the second interference figure from the interference pattern and (b) pixel interpolation and (II) produces a second reconstructed image of the object in regard to the second polarized-light component, the second reconstructed image corresponding to the third interference figure and the fourth interference figure, after (a) extraction of pixels corresponding to the third interference figure and the fourth interference figure from the interference pattern and (b) pixel interpolation; and the polarized-light-image-calculating section obtains the polarized-light images from the first reconstructed image and the second reconstructed image, the polarized-light images corresponding to respective positions in each of the reconstructed images of the object, wherein the reconstructed-image-producing section (i) obtains two respective intensity distributions of the first polarized-light component and the second polarized-light component of only the reference light, (ii) calculates respective complex amplitude distributions of the first polarized-light component and the second polarized-light component from the first to fourth interference figures and the two intensity distributions of only the reference light, and (iii) obtains a first amplitude distribution and a first phase distribution each as the first reconstructed image in regard to the first polarized-light component and a second amplitude distribution and a second phase distribution each as the second reconstructed image in regard to the second polarized-light component, from the complex amplitude distributions, wherein the polarized-light-image-calculating section obtains the polarized-light images corresponding to respective positions in each of the reconstructed images of the object, from the first amplitude distribution and the first phase distribution of the object and the second amplitude distribution and the second phase distribution of the object.

20. The polarization imaging apparatus as set forth in claim 19, wherein:

the reference light enters the image pickup section, being inclined, with respect to the object light, at an inclination angle obtained by:

$\sin^{-1}(\lambda/4\tau)$ where the wavelength of the reference light is $\lambda$ and the distance between pixels of the image pickup section is $\tau$.

21. The polarization imaging apparatus as set forth in claim 19, further comprising a spatial-carrier-phase-shifting region obtaining complex amplitude distributions of the object from interference figures of regions that are adjacent to each other along an inclination direction of the reference light.

22. An in-line type polarization imaging apparatus comprising:

at least one light source for supplying light including reference light and object light;

an image pickup section capturing images of interference figures each formed from the reference light and the object light that reaches the image pickup section through an object;

a reconstructed-image-producing section producing reconstructed images;

a polarized-light-image-calculating section obtaining polarized-light images;

a beam splitter splitting the light supplied from the light source into the reference light and the object light;

a phase-shift means for spatially shifting a phase of the reference light being a divisional portion of the light split by the beam splitter; and a beam-combining element combining the object light with the reference light having a phase shifted by the phase-shift means, the object light reaching after having passed through the object, wherein:

the object light and the reference light each include a first polarized-light component polarized in a first direction and a second polarized-light component polarized in a second direction that is different from the first direction, both of which object light and reference light enter the image pickup section;

the image pickup section simultaneously captures an image of an interference pattern including (i) a first interference figure formed by interference between the object light which has the first polarized-light component and the reference light which has the first polarized-light component and a first phase, (ii) a second interference figure formed by interference between the object light which has the first polarized-light component and the reference light which has the first polarized-light component and a second phase, (iii) a third interference figure formed by interference between the object light which has the second polarized-light component and the reference light which has the second polarized-light component and the first phase, and (iv) a fourth interference figure formed by interference between the object light which has the second light component and the reference light which has the second polarized-light component and the second phase;

the reconstructed-image-producing section (I) produces a first reconstructed image of the object in regard to the first polarized-light component, the first reconstructed image corresponding to the first interference figure and the second interference figure, after (a) extraction of pixels corresponding to the first interference figure and the second interference figure from the interference pattern and (b) pixel interpolation and (II) produces a second reconstructed image of the object in regard to the second polarized-light component, the second reconstructed image corresponding to the third interference figure and the fourth interference figure, after (a) extraction of pixels corresponding to the third interference figure and the fourth interference figure from the interference pattern and (b) pixel interpolation; and the polarized-light-image-calculating section obtains the polarized-light images from the first reconstructed image and the second reconstructed image, the polarized-light images corresponding to respective positions in each of the reconstructed images of the object, wherein the reconstructed-image-producing section (i) obtains two respective intensity distributions of the first polarized-light component and the second polarized-light component of only the reference light, (ii) calculates respective complex amplitude distributions of the first polarized-light component and the second polarized-light component from the first to fourth interference figures and the two intensity distributions of only the reference light, and (iii) obtains a first amplitude distribution and a first phase distribution each as the first reconstructed image in regard to the first polarized-light component and a second amplitude distribution and a second phase distribution each as the second reconstructed image in regard to the second polarized-light component, from the complex amplitude distributions, wherein the polarized-light-image-calculating section obtains the polarized-light images corresponding to respective positions in each of the reconstructed images of the object, from the first amplitude distribution and the first phase distribution of the object and the second amplitude distribution and the second phase distribution of the object.

23. A method for polarization imaging in which a polarization state of object light is obtained by capturing images of interference figures each formed by reference light and the object light that reaches through an object, the method comprising the steps of:

(A) splitting light supplied from a light source into the reference light and the object light each including a first polarized-light component polarized in a first direction and a second polarized-light component polarized in a second direction that is different from the first direction;

(B) inclining the reference light at an inclination angle based on a wavelength of the reference light and a distance between pixels of the image pickup section, the reference light being a divisional portion of the light split by the beam splitter;

(C) combining the object light with the reference light, the object light reaching after having passed through the object;

(D) making the reference light enter the image pickup section, the reference light being inclined at the inclination angle relative to the object light (E) capturing, simultaneously, an image of an interference pattern including first to fourth interference figures formed from the object light and the reference light, the first interference figure being formed by interference between the object light which has the first polarized-light component and the reference light which has the first polarized-light component and a first phase, the second interference figure being formed by interference between the object light which has the first polarized-light component and the reference light which has the first polarized-light component and a second phase, the third interference figure being formed by interference between the object light which has the second polarized-light component and the reference light which has the second polarized-light component and the first phase, and the fourth interference figure being formed by interference between the object light which has the second polarized-light component and the reference light which has the second polarized-light component and the second phase;

(F) producing (I) a first reconstructed image of the object in regard to the first polarized-light component, the first reconstructed image corresponding to the first interference figure and the second interference figure, after (a) extraction of pixels corresponding to the first interference figure and the second interference figure from the interference pattern and (b) pixel interpolation and (II) a second reconstructed image of the object in regard to the second polarized-light component, the second reconstructed image corresponding to the third interference figure and the fourth interference figure, after (a) extraction of pixels corresponding to the third interference figure and the fourth interference figure from the interference pattern and (b) pixel interpolation; and (G) obtaining polarized-light images from the first reconstructed image and the second reconstructed image, the polarized-light images corresponding to respective positions in each of the reconstructed images of the object, the step (F) including the sub-steps of:

obtaining two respective intensity distributions of the first polarized-light component and the second polarized-light component of only the reference light;

calculating respective complex amplitude distributions of the first polarized-light component and the second polarized-light component from the first to fourth interference figures and the two intensity distributions of only the reference light; and obtaining a first amplitude distribution and a first phase distribution each as the first reconstructed image in regard to the first polarized-light component and a second amplitude distribution and a second phase distribution each as the second reconstructed image in regard to the second polarized-light component, from the complex amplitude distributions, the step (G) including the sub-step of obtaining the polarized-light images corresponding to respective positions in each of the reconstructed images of the object, from the first amplitude distribution and the first phase distribution of the object and the second amplitude distribution and the second phase distribution of the object.

24. A method for polarization imaging in which a polarization state of object light is obtained by capturing images of interference figures each formed by reference light and the object light that reaches through an object, the method comprising the steps of:

(A) splitting light supplied from a light source into the reference light and the object light each including a first polarized-light component polarized in a first direction and a second polarized-light component polarized in a second direction that is different from the first direction;

(B) spatially shifting a phase of the reference light being a divisional portion of the light split;

(C) combining the object light with the reference light whose phase has been shifted, the object light reaching after having passed through the object;

(D) capturing, simultaneously, an image of an interference pattern including first to fourth interference figures formed from the object light and the reference light, the first interference figure being formed by interference between the object light which has the first polarized-light component and the reference light which has the first polarized-light component and a first phase, the second interference figure being formed by interference between the object light which has the first polarized-light component and the reference light which has the first polarized-light component and a second phase, the third interference figure being formed by interference between the object light which has the second polarized-light component and the reference light which has the second polarized-light component and the first phase, and the fourth interference figure being formed by interference between the object light which has the second polarized-light component and the reference light which has the second polarized-light component and the second phase;

(E) producing (I) a first reconstructed image of the object in regard to the first polarized-light component, the first reconstructed image corresponding to the first interference figure and the second interference figure, after (a) extraction of pixels corresponding to the first interference figure and the second interference figure from the interference pattern and (b) pixel interpolation and (II) a second reconstructed image of the object in regard to the second polarized-light component, the second reconstructed image corresponding to the third interference figure and the fourth interference figure, after (a) extraction of pixels corresponding to the third interference figure and the fourth interference figure from the interference pattern and (b) pixel interpolation; and (F) obtaining polarized-light images from the first reconstructed image and the second reconstructed image, the polarized-light images corresponding to respective positions in each of the reconstructed images of the object, the step (E) including the sub-steps of:

obtaining two respective intensity distributions of the first polarized-light component and the second polarized-light component of only the reference light;

calculating respective complex amplitude distributions of the first polarized-light component and the second polarized-light component from the first to fourth interference figures and the two intensity distributions of only the reference light; and obtaining a first amplitude distribution and a first phase distribution each as the first reconstructed image in regard to the first polarized-light component and a second amplitude distribution and a second phase distribution each as the second reconstructed image in regard to the second polarized-light component, from the complex amplitude distributions, the step (F) including the sub-step of obtaining the polarized-light images corresponding to respective positions in each of the reconstructed images of the object, from the first amplitude distribution and the first phase distribution of the object and the second amplitude distribution and the second phase distribution of the object.

* * * * *